(12) United States Patent
    Khanna

(10) Patent No.: US 12,605,488 B2
(45) Date of Patent: Apr. 21, 2026

(54) SURFACE TREATMENT METHODS FOR CEMENTLESS IMPLANTABLE MEDICAL DEVICES

(71) Applicant: Durahip, LLC, San Antonio, TX (US)

(72) Inventor: Rohit Khanna, San Antonio, TX (US)

(73) Assignee: Durahip, LLC, San Antonio, TX (US)

( * ) Notice: Subject to any disclaimer, the term of this patent is extended or adjusted under 35 U.S.C. 154(b) by 0 days.

(21) Appl. No.: 18/543,587

(22) Filed: Dec. 18, 2023

(65) Prior Publication Data

US 2024/0207482 A1     Jun. 27, 2024

Related U.S. Application Data

(60) Provisional application No. 63/387,933, filed on Dec. 16, 2022.

(51) Int. Cl.
    *C25D 9/06*          (2006.01)
    *A61L 27/06*         (2006.01)
    (Continued)

(52) U.S. Cl.
    CPC .............. *A61L 27/32* (2013.01); *A61L 27/06* (2013.01); *A61L 27/54* (2013.01); *A61L 27/56* (2013.01);
    (Continued)

(58) Field of Classification Search
    CPC ....... C23C 18/1653; C25D 9/04; C25D 11/04; C25D 11/26; C25D 9/06
    (Continued)

(56) References Cited

U.S. PATENT DOCUMENTS

| | | | |
|---|---|---|---|
| 5,211,833 A | 5/1993 | Shirkhanzadeh | |
| 9,839,720 B2 | 12/2017 | Gan et al. | |

(Continued)

FOREIGN PATENT DOCUMENTS

| | | | | |
|---|---|---|---|---|
| CN | 1986003 A | * | 6/2007 | ............. A61L 27/32 |
| CN | 101122025 A | * | 2/2008 | ................ C23F 1/04 |

(Continued)

OTHER PUBLICATIONS

Nakashima et al., "Hydroxyapatite-Coating on Titanium Arc Sprayed Titanium Implants," Journal of Biomedical Materials Research: An Official Journal of The Society for Biomaterials and The Japanese Society for Biomaterials (Jun. 5, 1997), vol. 35, No. 3, pp. 287-298. (Year: 1997).*

(Continued)

*Primary Examiner* — Edna Wong

(57)          ABSTRACT

A method of producing a bioactive surface on a medical device configured for cementless implantation is disclosed. The method can include treating a titanium metal or titanium alloy medical device, optionally having a titanium metal or titanium alloy porous coating, with a series of steps to obtain the bioactive surface having a nanofibrous network of titanate overlaid with hydroxyapatite particles or film. The steps can include treating the medical device with an acidic solution to obtain an activated surface; oxidizing the activated surface using plasma electrolytic oxidation to obtain an oxide layer having bioactive elements, compounds, or phases; treating the oxide layer with an alkaline solution to obtain the bioactive surface; and treating the bioactive surface with an iodine containing compound to obtain an antibacterial and bioactive surface.

21 Claims, 20 Drawing Sheets

(51) Int. Cl.

| | | |
|---|---|---|
| *A61L 27/32* | (2006.01) | |
| *A61L 27/54* | (2006.01) | |
| *A61L 27/56* | (2006.01) | |
| *B33Y 70/00* | (2020.01) | |
| *B33Y 80/00* | (2015.01) | |
| *C25D 11/02* | (2006.01) | |
| *C25D 11/26* | (2006.01) | |
| B82Y 5/00 | (2011.01) | |
| C23C 4/08 | (2016.01) | |
| C23C 4/134 | (2016.01) | |
| C23C 24/08 | (2006.01) | |

(52) U.S. Cl.
CPC .............. *B33Y 70/00* (2014.12); *B33Y 80/00* (2014.12); *C25D 11/024* (2013.01); *C25D 11/026* (2013.01); *C25D 11/26* (2013.01); *A61L 2300/412* (2013.01); *A61L 2400/12* (2013.01); *A61L 2420/02* (2013.01); *A61L 2420/04* (2013.01); *A61L 2430/02* (2013.01); *B82Y 5/00* (2013.01); *C23C 4/08* (2013.01); *C23C 4/134* (2016.01); *C23C 24/087* (2013.01)

(58) Field of Classification Search
USPC ........ 205/189, 198, 200, 212, 199, 210, 220
See application file for complete search history.

(56) References Cited

U.S. PATENT DOCUMENTS

| | | | | |
|---|---|---|---|---|
| 9,889,231 | B2 | 2/2018 | Tsuchiya et al. | |
| 10,893,944 | B2 | 1/2021 | Gorhe et al. | |
| 10,940,234 | B2 | 3/2021 | Tsuchiya | |
| 11,141,244 | B2 | 10/2021 | Kumar et al. | |
| 11,285,241 | B2 | 3/2022 | Tyber et al. | |
| 11,395,740 | B2 | 7/2022 | Gorhe et al. | |
| 2011/0218643 | A1* | 9/2011 | Yerokhin | C25D 11/26 427/2.27 |
| 2021/0001004 | A1 | 1/2021 | Yamaguchi et al. | |
| 2022/0331115 | A1 | 10/2022 | Gorhe et al. | |

FOREIGN PATENT DOCUMENTS

| | | | | | |
|---|---|---|---|---|---|
| CN | 102039408 | A | * | 5/2011 | ............. A61L 27/30 |
| CN | 102677126 | A | * | 9/2012 | ............. A61L 27/30 |
| CN | 102851674 | A | * | 1/2013 | ............. C23C 22/34 |
| CN | 104947107 | A | * | 9/2015 | ............. C25C 10/22 |
| CN | 105543934 | A | * | 5/2016 | ............. C25D 11/26 |
| CN | 106435691 | A | * | 2/2017 | ............... C23G 1/10 |
| CN | 106560530 | A | * | 4/2017 | ............. C23G 1/106 |
| CN | 105543934 | B | * | 7/2018 | ............. C25D 11/26 |
| CN | 109913815 | A | * | 6/2019 | ............. C23C 14/02 |
| CN | 110200727 | A | * | 9/2019 | ............... A61F 2/28 |
| CN | 2371398 | B1 | * | 6/2020 | ............. A61L 27/06 |
| CN | 111218706 | A | * | 6/2020 | ............. A61L 27/06 |
| CN | 111481738 | A | * | 8/2020 | ........... A61L 27/047 |
| CN | 111228568 | A | | 11/2021 | |
| EP | 2371398 | A1 | | 10/2011 | |
| EP | 2371398 | B1 | * | 5/2013 | ............. A61L 27/04 |
| EP | 102039408 | A | * | 5/2013 | ............. A61L 27/04 |
| TR | 201812337 | A2 | * | 9/2018 | ........... A61C 8/0013 |
| WO | WO-2020157743 | A1 | * | 8/2020 | ........... A61F 2/3094 |

OTHER PUBLICATIONS

Wang et al., "Study of Process Affected by Electrolyte Concentration through Microarc Oxidation on the TC4 Alloy Surface," Open Access Library Journal (Jan. 1, 2015), vol. 2, No. 1, pp. 1-7. (Year: 2015).*

Qin et al., "Micro-and Nano-Structured 3D Printed Titanium Implants with a Hydroxyapatite Coating for Improved Osseointegration," Journal of Materials Chemistry B (2018), vol. 6, No. 19, pp. 3136-3144. (Year: 2018).*

Ni et al., "Effect of Micro-Arc Oxidation Surface Modification of 3D-Printed Porous Titanium Alloys on Biological Properties," Annals of Translational Medicine (Jun. 2022), vol. 10, No. 12, pp. 1-11. (Year: 2022).*

Zhang et al., "Effect of Ti—OH Groups on Microstructure and Bioactivity of TiO2 Coating Prepared by Micro-Arc Oxidation," Applied Surface Science (Mar. 1, 2013), vol. 268, pp. 381-386. (Year: 2013).*

Sefer et al., "Chemical Milling of Cast Ti—6Al—4V and Ti—6Al—2Sn—4Zr—2Mo Alloys in Hydrofluoric-Nitric Acid Solutions," Corrosion (Apr. 1, 2017), vol. 73, No. 4, pp. 394-407. (Year: 2017).*

Huang et al., "Comparative Study on 3D Printed Ti6Al4V Scaffolds with Surface Modifications Using Hydrothermal Treatment and Microarc Oxidation to Enhance Osteogenic Activity," ACS Omega (Jan. 7, 2021), vol. 6, No. 2, pp. 1465-1476. (Year: 2021).*

Yu et al., "Enhanced Bioactivity and Interfacial Bonding Strength of Ti3Zr2Sn3Mo25Nb Alloy Through Graded Porosity and Surface Bioactivation," Journal of Materials Science & Technology (Feb. 20, 2022), vol. 100, pp. 137-149. (Year: 2022).*

Liu et al., "Formation of Hydroxyapatite on Ti—6Al—4V Alloy by Microarc Oxidation and Hydrothermal Treatment," Surface and Coatings Technology (Sep. 22, 2005), vol. 199, Nos. 2-3, pp. 220-224. (Year: 2005).*

Wysocki et al., "Post Processing and Biological Evaluation of the Titanium Scaffolds for Bone Tissue Engineering," Materials (Mar. 15, 2016), vol. 9, No. 3, pp. 1-19. (Year: 2016).*

Kearney, "Metal Cleaning and Its Improvement by the Use of Ultrasonics,", Transactions of the IRE Professional Group on Ultrasonic Engineering (Dec. 5, 2005), pp. 43-47. (Year: 2005).*

Budei et al., "The Effect of Ultrasonic Cleaning on Medical Grade Anodized Titanium Used for Dental Implants," Bulletin of Romanian Chemical Engineering Society (2017), vol. 4, No. 2, pp. 24-32. (Year: 2017).*

Yamaguchi et al., "Iodine-Loaded Calcium Titanate for Bone Repair with Sustainable Antibacterial Activity Prepared by Solution and Heat Treatment," Nanomaterials (Aug. 26, 2021), vol. 11, No. 9, pp. 1-20. (Year: 2021).*

Rafieerad, A.R., et al., Surface characterization and corrosion behavior of calcium phosphate-base composite layer on titanium and its alloys via plasma electrolytic oxidation: A review paper; Materials Science and Engineering, 2015, C57, 397-413.

Ni, R., et al., Effect of micro-arc oxidation surface modification of 3D-printed porous titanium alloys on biological properties; Annals of Translational Medicine, 2022, 10(12) (11 pages).

Shi, X., et al., Effects of electrolytic concentration on properties of micro-arc film on Ti6Al4V alloy; Mining Science and Technology, 2009, 19, 220-224.

Han Y., et al., UV-enhanced bioactivity and cell response of micro-arc oxidized titania coatings; Acta Biomaterialia, 2008, 4, 1518-1529.

Han, Y., et al., Synthesis of nanocrystalline titania films by micro-arc oxidation; Materials Letters, 2002, 56, 744-747.

Wei, D., et al., Structure and apatite formation of microarc oxidized TiO2-based films before and after alkali-treatment by various alkali concentrations; Surface & Coatings Technology, 2008, 202, 5012-5019.

Aliofkhazraei, M., et al., Review of plasma electrolytic oxidation of titanium substrates: Mechanism, properties, applications and limitations; Applied Surface Science Advances 2021, 5, 100121 (67 pages).

Lee, U., et al., Osseointegration of 3D-printed titanium implants with surface and structure modifications; Dental Materials, 2022, 38, 1648-1660.

Wei, D., et al., Characteristic and microstructure of the micoarc oxidized TiO2-based film containing P before and after chemical- and heat treatment; Applied Surface Science, 2009, 255, 7851-7857.

Liu, F., et al., Hydroxyapatite formation on oxide films containing Ca and P by hydrothermal treatment; Ceramics International, 2006, 36, 527-531.

Zhang, P., et al., Effect of Ti—OH groups on microstructure and bioactivity of TiO2 coating prepared by micro-arc oxidation; Applied Surface Science, 2013, 268, 381-386.

(56)        References Cited

OTHER PUBLICATIONS

Ikeda, N., et al., Bioactivity and antibacterial activity of iodine-containing calcium titanate against implant-associated infection; Biomaterials Advances, 2022, 138, 212952 (16 pages).

Gallo, Jiri, et al., Antibacterial Surface Treatment for Orthopaedic Implants; International Journal of Molecular Sciences, 2014, 15, 13849-13880.

Cao, H., et al., Activating titanium oxide coatings for orthopedic implants; Surface & Coatings Technology, 2013, 233, 57-64.

Minter, J., et al., Characterization of a New Rougher Porous Coating for Revision Reconstructive Surgery; 54th Annual Meeting of the Orthpaedic Research Society, 2016 (2 pages).

Rivard, K., et al., Qualification of Hot Isostatic Pressing Processes; ResearchGate, 2011 (6 pages).

Dzhurinskiy, D., et al., Characterization and corrosion evaluation of TiO2:n-HA coatings on titanium alloy formed by plasma electrolytic oxidation; Surface & Coatings Technology, 2015, 269, 258-265.

Durdu, S., et al., Characterization and formation of hydroxyapatite on Ti6Al4V coated by plasma electrolytic oxidation; Journal of Alloys and Compounds, 2013, 551, 422-429.

Abbasi, S., et al., Effect of electrolyte concentration on microstructure and properties of micro arc oxidized hydroxyapatite/titania nanostructured composite; Materials Science and Engineering, 2013, C33, 2555-2561.

Yang, Y., et al., Enhancing Osseointegration Using Surface-Modified Titanium Implants; JOM, 2006, 71-76.

Han, Y., et al., Formation mechanism of HA-based coatings by micro-arc oxidation; Electrochemistry Communications, 2008, 10, 510-513.

Chen, K., et al., Effects of Micro-Arc Oxidation Discharge Parameters on Formation and Biomedical Properties of Hydroxyapatite-Containing Flower-like Structure Coatings; Materials, 2023, 16, 57 (19 pages).

Lugovskoy, A., Production of hydroxyapatite layers on the plasma electrolytically oxidized surface of titanium alloys; Materials Science and Engineering, 2014, C43, 527-532.

* cited by examiner

100

105 — PROVIDING A METAL MEDICAL DEVICE

110 — DEGREASING THE DEVICE SURFACE

115 — ACTIVATING THE DEVICE SURFACE

120 — WASHING THE ACTIVATED DEVICE

125 — TREATING THE ACTIVATED DEVICE WITH PEO TO FORM AN OXIDE LAYER

130 — WASHING THE OXIDIZED DEVICE

135 — ACTIVATING THE OXIDIZED DEVICE

140 — TREATING THE ACTIVATED OXIDIZED SURFACE WITH ANTIBACTERIAL

145 — WASHING AND DRYING THE DEVICE

SURFACE TREATMENT METHODS FOR CEMENTLESS IMPLANTABLE MEDICAL DEVICES

CROSS-REFERENCE TO RELATED APPLICATIONS

This application claims the benefit of priority under 35 U.S.C. § 119(e) of U.S. Provisional Application Ser. No. 63/387,933, filed on Dec. 16, 2022, the content of which is relied upon and incorporated herein by reference in its entirety.

FIELD

This disclosure relates to cementless implantable medical devices, and more particularly to methods of treating the surfaces of the cementless implantable medical devices to produce one or more surface layers having improved biofunctionality and properties, including enhanced osseointegration, bone in-growth, bone regeneration, antibacterial activities, or a combination of two or more of the properties.

BACKGROUND

There are hundreds of thousands of hip and knee arthroplasties performed each year in the United States, and that number is expected to increase due to the rising population of people suffering from obesity and people aged between 40 and 60. Despite recent technological advances, there remains a need for durable, long lasting cementless implantable medical devices (e.g., artificial joints, dental screws, spinal implants such as pedicle screws, lumber interbody cages, metal coated polymers, 3D printed implants) with improved surface properties that facilitate bone in-growth and on-growth and which reduce the risks of implant failure due to infection, loosening, dislocation, fracture, and/or corrosion.

SUMMARY

In various embodiments, a method of producing a bioactive surface on a medical device configured for cementless implantation is provided. In some embodiments, the medical device is comprised of a commercially pure titanium metal or a titanium alloy. The method can include: treating the medical device with an acidic solution, at a temperature between 20° C. and 70° C., to obtain an activated surface on the medical device; treating the activated surface using plasma electrolytic oxidation, in an electrolyte solution comprising calcium and phosphate salts, at a temperature between 15° C. and 50° C., to obtain an oxidized surface on the medical device comprising a microporous oxide layer having bioactive elements, compounds, or phases; and treating the oxidized surface of the medical device with an alkaline solution comprising hydroxide in a concentration range of 0.01M to 5.0M, at a temperature between 20° C. and 90° C., to obtain a bioactive surface on the medical device comprising a nanofibrous network, a composite of the nanofibrous network and hydroxyapatite particles, or a film comprising hydroxyapatite over the composite of the nanofibrous network and hydroxyapatite particles.

In some embodiments, the acidic solution comprises nitric acid, hydrofluoric acid, and water; and wherein the nitric acid has a molar concentration in a range of 0.1M to 12M and the hydrofluoric acid has a molar concentration in a range of 0.01M to 1M.

In some embodiments, the surface of the medical device comprises a porous commercially pure titanium coating obtained by a sintering or plasma spraying of one or more titanium powder compositions.

In some embodiments, the medical device is obtained by a 3D printing of one or more titanium alloy powder compositions.

In some embodiments, the oxidized surface of the medical device comprises calcium and phosphorus in a calcium to phosphorus ratio in a range from 0.5 to 1.2. In some embodiments, the oxidized surface or bioactive surface comprises calcium and phosphorus in a calcium to phosphorus ratio in a range from 1.4 to 2.2.

In some embodiments, the bioactive surface comprises calcium titanate, sodium titanate, sodium hydrogen titanate, a titanate having a bioactive or antibacterial element, hydroxyapatite, hydroxyapatite having a bioactive or antibacterial element, or a combination thereof.

In some embodiments, the alkaline solution is in a concentration range of 0.1M to 1.0M. In some embodiments, the hydroxide is sodium hydroxide or potassium hydroxide.

In some embodiments, the plasma electrolytic oxidation comprises a mean voltage in a range of 150V to 800V; a frequency of pulses in a range from 10 Hz to 1500 Hz; a duty cycle in a range of 3% to 30%, and a treatment time of less than 60 minutes.

In some embodiments, the mean voltage is in a range of 200V to 500V, and the frequency of pulses is in a range of 400 Hz to 1000 Hz.

In some embodiments, the method further comprises, prior to treating the medical device with an acidic solution, degreasing the medical device in a solution comprising water, an organic solvent, or a combination thereof, for 5 to 60 minutes, to remove impurities from the surface.

In some embodiments, the method further comprises, after treating the medical device with an acidic solution, washing the activated surface on the medical device in water for 5-30 minutes at a temperature in a range of 40° C. to 60° C., to remove residual acidic solution.

In some embodiments, the method further comprises, after treating the medical device using plasma electrolytic oxidation, washing the medical device in water for 5 to 60 minutes, to remove residual salts from the electrolyte that are physically adsorbed onto the medical device.

In some embodiments, the method further comprises, after treating the oxidized medical device with the alkaline solution to obtain a bioactive surface, washing the medical device to remove the physically adsorbed ions from the surface of the medical device.

In some embodiments, the method further comprises heat treating the medical device at a temperature in a range of 400 to 700° C. in an air atmosphere.

In some embodiments, the method further comprises, treating the medical device with an iodine source to obtain an antibacterial surface. In some embodiments, the iodine is impregnated on the surface by submerging the medical device in an iodine-containing solution at room temperature to 60° C.

In various embodiments, the method comprises: treating the medical device with an acidic solution, at a temperature between 20° C. and 70° C., to obtain an activated surface on the medical device; treating the activated surface using plasma electrolytic oxidation, in an electrolyte solution comprising calcium and phosphate salts, at a temperature between 15° C. and 50° C., to obtain an oxidized surface on the medical device comprising a microporous oxide layer having bioactive elements, compounds, or phases; and treating the oxidized surface of the medical device with an alkaline solution comprising sodium hydroxide in a concentration range of 0.01M to 5.0M, at a temperature between 20° C. and 90° C., to obtain a bioactive surface on the medical device comprising a nanofibrous network, a composite of the nanofibrous network and hydroxyapatite particles, or a film comprising hydroxyapatite over the composite of the nanofibrous network and hydroxyapatite particles; wherein the bioactive surface comprises calcium and phosphorus in a calcium to phosphate ratio of about 1.67.

In various embodiments, the method comprises: treating the medical device with an acidic solution, at a temperature between 20° C. and 70° C., to obtain an activated surface on the medical device; washing the activated surface on the medical device in water for 5-30 minutes at a temperature in a range of 40° C. to 60° C., to remove residual acidic solution, if present; treating the medical device using plasma electrolytic oxidation, in an electrolyte solution comprising calcium and phosphate salts, at a temperature between 15° C. and 50° C., to obtain an oxidized surface on the medical device comprising a microporous oxide layer having bioactive elements, compounds, or phases; washing the medical device in water for 5 to 60 minutes, to remove residual salts from the electrolyte that are physically adsorbed onto the medical device; and treating the oxidized surface of the medical device with an alkaline solution comprising sodium hydroxide in a concentration range of 0.01M to 5.0M, at a temperature between 20° C. and 90° C., to obtain a bioactive surface on the medical device comprising a nanofibrous network, a composite of the nanofibrous network and hydroxyapatite particles, or a film comprising hydroxyapatite over the composite of the nanofibrous network and hydroxyapatite particles; washing the medical device to remove the physically adsorbed ions from the surface of the medical device.

It is to be understood that both the foregoing general description and the following detailed description describe various embodiments and are intended to provide an overview or framework for understanding the nature and character of the claimed subject matter. The accompanying drawings are included to provide a further understanding of the various embodiments and are incorporated into and constitute a part of this specification. The drawings illustrate the various embodiments described herein and, together with the description, explain the principles and operations of the claimed subject matter.

BRIEF DESCRIPTION OF THE DRAWINGS

A complete understanding of the present embodiments and the advantages and features thereof will be more readily understood by reference to the following detailed description, appended claims, and accompanying drawings, wherein:

Figure 1:
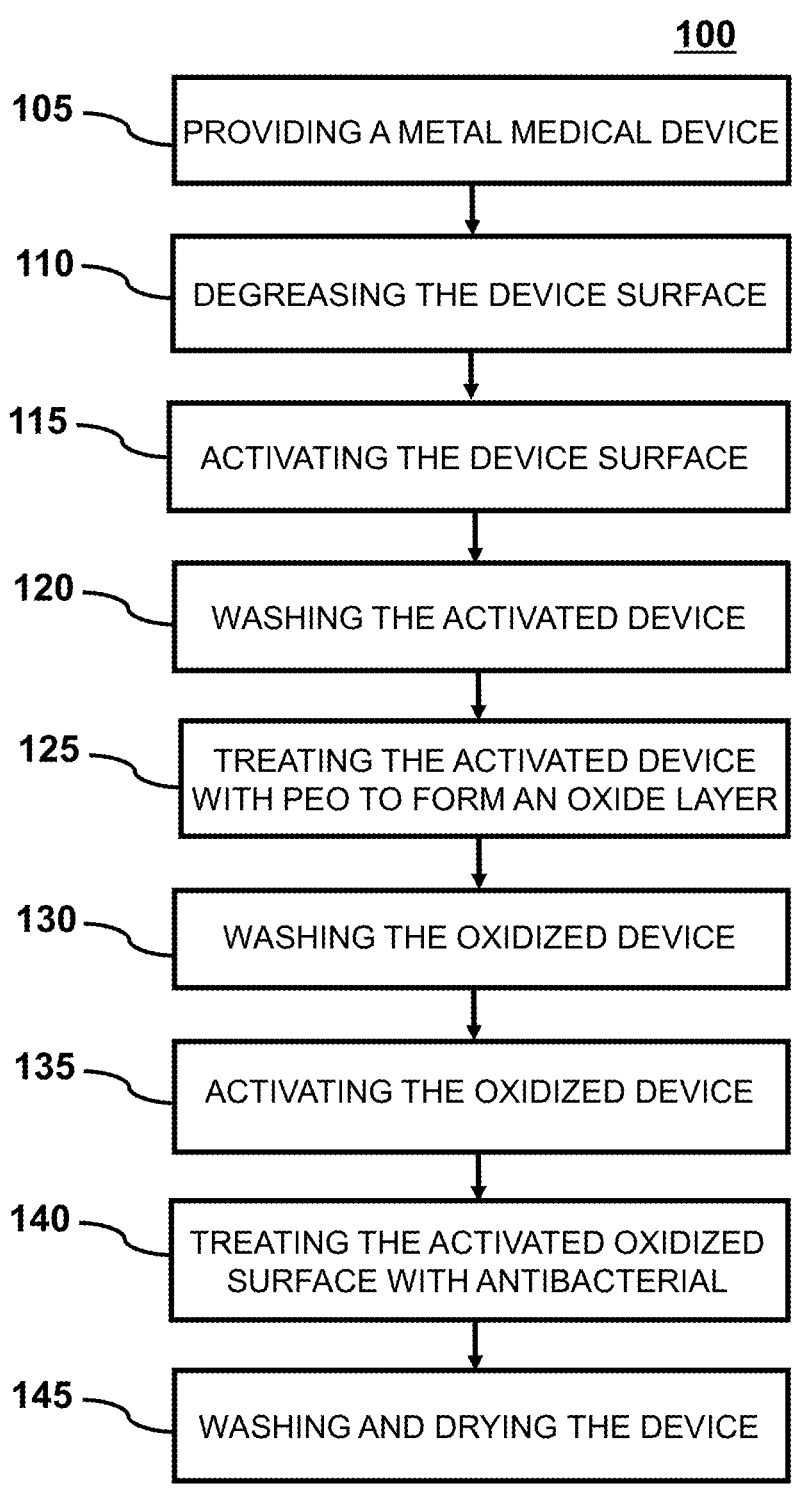
FIG. 1 provides a flowchart showing various steps of the methods of producing bioactive and antibacterial medical devices, in accordance with embodiments described herein.

The drawings are not necessarily to scale, and certain features and certain views of the drawings may be shown exaggerated in scale or in schematic in the interest of clarity and conciseness.

DETAILED DESCRIPTION

Reference will now be made in detail to the exemplary embodiment(s), examples of which is/are illustrated in the present disclosure. An embodiment refers to a particular feature or characteristic used in connection with a product or method step described herein. References to an "embodiment" appear throughout the disclosure, and such references are not necessarily referring to the same embodiment or to separate, mutually exclusive embodiment. Generally, the embodiments reside in combinations of components, subcomponents, and/or procedures related to a surface treatment of metal medical devices. Accordingly, the product and method components have been represented where appropriate, showing only those specific details that are pertinent to understanding the embodiments of the present disclosure so as not to obscure the disclosure with details that will be readily apparent to those of ordinary skill in the art having the benefit of the description herein. The specific details of the various embodiments described herein are used for demonstration purposes only, and no unnecessary limitation or inferences are to be understood therefrom.

In various embodiments, as shown in FIGS. 1-16B, a system and method of treating one or more surfaces of a medical device are provided. In some embodiments, the medical device is comprised of a metal (pure, elemental) or a metal alloy. In some embodiments, the medical device is comprised porous CpTi metal coating applied onto a Ti alloy or thermoplastic polymer. In some embodiments, the medical device is a metallic scaffold. In some embodiments, the medical device is obtained by 3D printing (additive manufacturing).

In some embodiments, the medical device is an implant, such as a prosthetic implant (e.g., hip stems, hip cups, elbows, knee tibia, knee femoral, foot and ankle, spine, shoulders, ankles, wrists, interbody spinal cage, and craniofacial, oral, and maxillofacial implants). In some embodiments, the medical device is configured as a cementless implant. Unlike a traditional prosthetic, which is held in place with bone cement that bonds the prosthetic to the subject's natural bone, a cementless implant is not cemented into place with bone cement. In some embodiments, the medical device is hardware (e.g., dental screws, orthopedic screws, pedicle screws, fracture plates, tibial nails).

In some embodiments, the medical device is comprised of commercially pure (Cp) titanium (Ti) (CpTi), a titanium alloy, tantalum (Ta) metal, a tantalum alloy, or a combination thereof. In some embodiments, the titanium alloy is Ti-6Al-4V, Ti-6Al-7Nb, Ti-13Nb-13Zr, Ti-5Zr-3Mo-15Nb, or Ti-15Mo-5Zr-3Al. In some embodiments, the titanium alloy is Ti-6Al-4V ELI alloy (ASTM F136) (ELI stands for extra low interstitials).

In some embodiments, the surface of the medical device comprises a coating. In some embodiments, the coating is a porous coating. In some embodiments, the medical device does not have a coating and has a non-porous surface (a "dense" implant). In some embodiments, the medical device comprises one or more porous coated regions and one or more dense regions. As used herein, the term "substrate" refers to a medical device that does not have a coating. In some embodiments, the medical device is a cementless implant comprising a textured, porous surface coating configured to encourage bone in-growth and on-growth. In such embodiments, the coating provides the adequate roughness and porosity for promoting bone in-growth, on-growth, and early-stage device fixation. In some embodiments, the device comprises a porous CpTi or Ti-6Al-4V coating on a substrate comprising CpTi or Ti-6Al-4V alloy (e.g., CpTi coating on Ti-6Al-4V substrate; CpTi coating on CpTi substrate; Ti-6Al-4V coating on Ti-6Al-4V substrate, CpTi coating on thermoplastic polymers (e.g., polyether ether ketone (PEEK), polyether ketone ketone (PEKK)).

In some embodiments, the coating is obtained by a process involving the sintering of one or more titanium powder compositions (e.g., CpTi or titanium alloys) to the surface of the substrate. In some embodiments, a porous coating of CpTi or titanium alloy is applied by sintering a titanium powder (in the form of beads, e.g., asymmetrical beads, spherical beads, or a combination thereof) to a titanium alloy substrate. In some embodiments, a CpTi or titanium alloy coating is plasma sprayed onto the surface of the metal or thermoplastic polymer substrate. In some embodiments, the porous coating or surface can be formed by sandblasting or by a chemical treatment. The chemical treatment can include, e.g., an alkali treatment or acid etching of a device comprised of CpTi metal, a titanium alloy, or a combination thereof.

In some embodiments, the coating comprises one or more thin layers (30-50 μm thick) of plasma sprayed hydroxyapatite (HA) applied over a porous CpTi, a titanium alloy coated, or a titanium alloy 3D scaffold medical device. In some embodiments, the coating comprises one or more plasma sprayed hydroxyapatite coatings applied directly on the substrate device without the porous CpTi or a titanium alloy coating. In some embodiments, the porous coating can be formed by a single method or a combination of methods, including sintered beads of CpTi, titanium plasma spray (TPS) CpTi coating, additive manufacturing (3D printing) of titanium alloy powders, or by the pressing or welding of metallic fibers. In various embodiments described herein, a porous coated CpTi or titanium alloy medical device can be modified according to the methods described herein.

In various embodiments, the porosity of the porous coated surface on the medical device ranges from about 40% to about 90%, and the pore size ranges from about 100 microns to about 1500 microns. In some embodiments, the shape of the pores in the porous coating may be one or more of a cubic structure, diamond lattice structure, irregular pore structure, stochastic lattice structure, spherical shape, a combination of irregular and spherical shape, or structures formed by titanium wire sintering.

In some embodiments, the porous coating or three-dimensional scaffold is comprised of a metal or metallic alloy that is capable of being oxidized by anodic spark deposition (also known as plasma electrolytic oxidation) to form a microporous oxide layer on the porous coating. The microporous surface layer of oxide on the porous coating can incorporate (e.g., doped) bioactive elements, antibacterial elements, compounds, phases, or combinations thereof. The bioactive elements can include, e.g., calcium (Ca), phosphorous (P), strontium (Sr), silicon (Si), magnesium (Mg), lithium (Li), gallium (Ga), or zinc (Zn). The antibacterial elements can include silver (Ag), copper (Cu), iodine (I), etc. The bioactive compounds can include, e.g., proteins, peptides, growth factors, osteogenic compounds, titanates, hydroxyapatite, calcium phosphates or combinations thereof. The antimicrobial compounds can include, e.g., antibiotics, antimicrobial metal ions or particles, antimicrobial peptides, iodine, that can resist microbial adhesion and growth over a long period of time. The bioactive phases include a nanofibrous network, nano-to-micro sized particles, or a composite of the microstructures of the nanofibrous network and nano-to-micro sized particles, wherein the phases comprise hydroxyapatite, anatase, rutile, sodium titanate, calcium titanate, titanate containing bioactive or antibacterial elements, hydroxyapatite containing bioactive or antibacterial elements, and/or combinations thereof. In various embodiments, the surface treatments on a porous coated medical device can increase the surface area of the porous surface, improve the surface tension, or wettability, of the porous surface, promote bone in-growth and on-growth, promote osseointegration and bone regeneration, and/or develop oxygen rich compounds for effective overlaying of the bioactive and antibacterial elements, compounds, phases, or combinations thereof.

During use, the porous coating on the medical device may be in contact with the bone of a subject. In some embodiments, the oxide layer of a porous metal coating can be a supporting surface for osteoconductive and/or osteoinductive compounds and phases, including, for example, simulated body fluid, bone morphogenetic proteins, and/or antimicrobial compounds. In some embodiments, a metal coating is overlayed on the surface of the porous coated medical device. In some embodiments, the metal coating is tantalum metal, tantalum alloy particles, or tantalum oxide particles, which are deposited on the porous coated medical device to enhance its bioactivity due to the good osteoconductivity properties of tantalum. In some embodiments, a porous titanium scaffold structure obtained by additive manufacturing methods is modified by anodization treatment to form a surface oxide layer comprising nanotubes. In some embodiments, the anodization treatment includes a fluoride-based electrolyte.

In various embodiments, a method of treating the surfaces of a porous coated CpTi device, titanium alloy device, 3D printed porous titanium alloy device, or a non-porous (dense) titanium alloy medical device is provided. In some embodiments, as shown in FIG. 1, the method 100 comprises a plurality of steps, including one or more surface treatment steps.

Figure 2A:
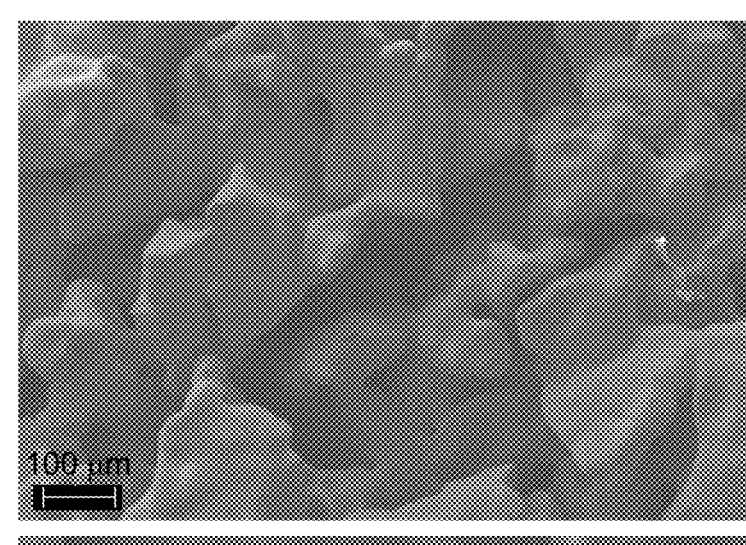
FIG. 2A and FIG. 2B are scanning electron microscope (SEM) images of the surface of a porous ABS CpTi coated titanium alloy coupon, as received from the manufacturer.

In various embodiments, the method 100 comprises the step 105 of providing a metal medical device. In some embodiments, the step 105 comprises providing a titanium alloy substrate having a porous CpTi metal or titanium alloy coating. In some embodiments, the porous coating is comprised of powder particles ("beads") of CpTi or a Ti alloy that are irregular in shape and capable of being fused together by sintering methods. This type of coating is referred to as an asymmetric bead sintered (ABS) CpTi or titanium alloy porous coating. FIG. 2A (100×) and FIG. 2B (250×) are images obtained from a scanning electron microscope (SEM) of the surface of a porous coated coupon (sample received from a manufacturer) comprised of a titanium alloy (Ti-6Al-4V) substrate with an ABS CpTi surface coating. The thickness of the ABS CpTi coating can range from about 0.8 mm to about 1.5 mm. The individual size of a bead ranges from about 170 μm to about 500 μm. The mean porosity of the ABS CpTi coating is about 60% and the mean pore size is about 250 μm.

Figure 2B:
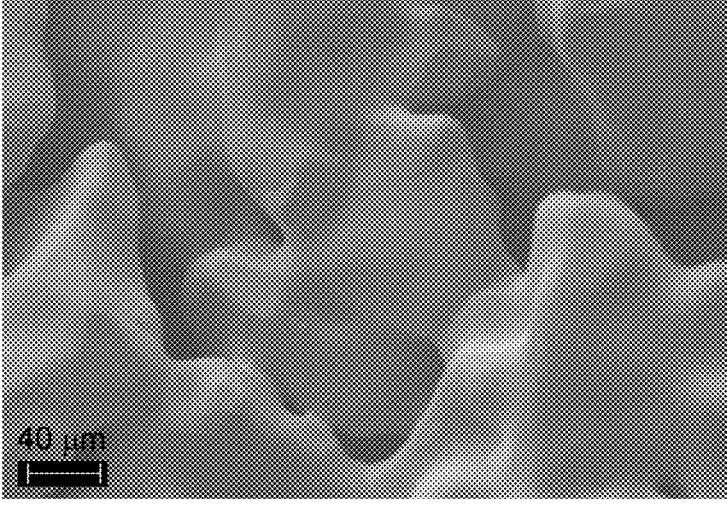
Figure 2C:
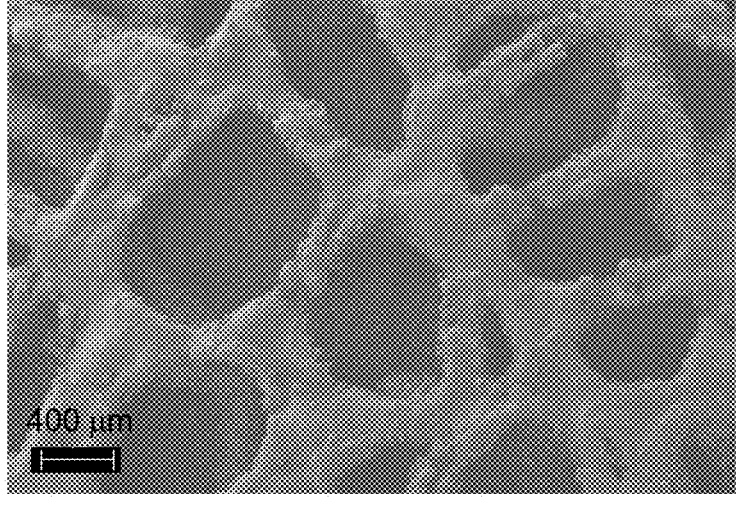
FIG. 2C is an SEM image of the surface of a 3D printed Ti-6Al-4V coupon produced by a selective laser melting method, as received from the manufacturer.
Figure 2D:
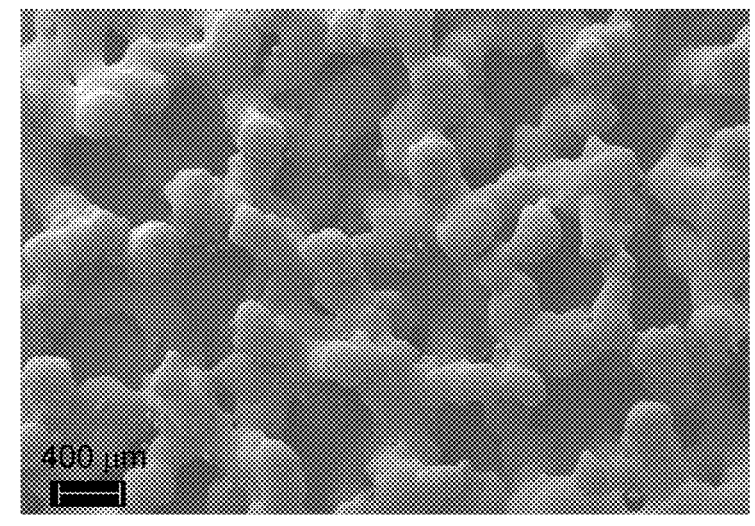
FIG. 2D is an SEM image of the surface of a 3D printed Ti-6Al-4V coupon produced by an electron beam melting method, as received from the manufacturer.

In some embodiments, the step 105 comprises providing a 3D printed device comprised of titanium alloy. FIG. 2C is an SEM image at 25× magnification of the surface of a porous coated 3D printed coupon (sample received from a manufacturer) made of a Ti-6Al-4V substrate with a Ti-6Al-4V coating by selective laser melting method. The lattice structure of the coating is that of a stochastic or random structure that is applied on the surface of a Ti alloy medical device or scaffold for orthopedic applications. The thickness of the 3D printed porous coating is about 1 mm. The mean porosity of the 3D printed Ti alloy coating is about 60% and the mean pore size is about 600 μm and varies in the range of 300 to 900 μm. FIG. 2D is an SEM image at 23× magnification of the surface of a porous coated 3D printed coupon (sample received from a manufacturer) made of a Ti-6Al-4V substrate with a Ti-6Al-4V coating by electron beam melting method. The lattice structure of the coating is that of a random structure applied on the surface of a Ti alloy medical device to mimic the structure of bone. The mean porosity of the 3D printed Ti alloy coating is about 60% and the mean pore size is about 500 μm. In some embodiments, the step 105 comprises providing a dense medical device comprised of CpTi metal or titanium alloys, such as Ti-6Al-4V.

In some embodiments, the method 100 comprises the degreasing step 110. In some embodiments, the step 110 comprises degreasing a porous coated device or porous device. The degreasing step removes impurities (e.g., oils, dirt, greases, or any loose surface contaminants) from the surface of the substrate. Suitable solutions for the degreasing step 110 include aqueous, organic, or a mixture of both. In some embodiments, for example, the solution comprises, acetone, 2-propanol, water (e.g., distilled, pure water), and mixtures or combinations thereof. In some embodiments, the degreasing of ABS CpTi porous coated devices is performed sequentially. For example, the degreasing sub-steps may include separate washings with acetone, 2-propanol, and water, for at least 30 minutes by ultrasonication method. In some embodiments, the solution is warmed to a temperature in the range of from 40° C. to 60° C.

In some embodiments, the step 110 comprises degreasing a 3D printed device. The removal of contamination and residual powders from a 3D printed device is not addressed by existing blasting methods involving hard abrasives, which can get trapped inside the complex lattice structures of the 3D printed porous device. In some embodiments, the 3D printed porous medical device is sonicated sequentially in propanol and water, each in the range of 40° C. to 60° C., until the residual powders are removed from the 3D printed device. In some embodiments, the total ultrasonication time for the removal of the residual powders on the 3D printed device is in the range of about 1 to 5 hours, or about 2 to 3 hours. In some embodiments, commercial detergents are used to reduce the duration of ultrasonication (e.g., to about 1 to 2 hours). In some embodiments, the 3D printed device is subjected to an additional degreasing step to remove any residual organic compounds. In such embodiments, the additional degreasing step includes ultrasonication in deionized water for at least 30 minutes.

In some embodiments, the method 100 comprises the surface activating step 115. In this context, "activating" or "activation" refers to exposing the native metal surface, which occurs after the removal of any surface impurities, including oxide scales that can be present on metal surfaces. In some embodiments, the substrate has a porous coating. In other embodiments, the substrate does not have a porous coating. In some embodiments, a 3D printed porous device is treated with the activating step 115. In some embodiments, the substrate has a porous coating, and the step 115 comprises activating the surfaces of the porous coated substrate to enhance wettability and reduce the surface tension of the surfaces, with minimal etching.

In some embodiments, the activating step 115 comprises treating the substrate with an acidic solution. In this context, the acid treatment can include soaking a device in a bath under controlled temperature and atmosphere conditions. In this context, "acidic" refers to the components and/or pH of the solution. In some embodiments, the acidic solution comprises nitric acid, hydrofluoric acid, hydrochloric acid, water, or combinations thereof. In some embodiments, for example, the acidic solution comprises a mixture of water and nitric acid (70% $HNO_3$) in a molar concentration ranging from about 0.1M to about 12M, from about 0.4M to about 10M, from about 0.6M to about 9M, etc. In some embodiments, for example, the acid solution comprises a mixture of water and hydrofluoric acid (HF) in a molar concentration ranging from about 0.01M to about 2M, from about 0.01M to about 1M, from about 0.1M to about 1M, from about 0.5M to about 1M, from about 0.5M to about 0.75M, from about 0.75M to about 1M, etc. In some embodiments, the acid solution comprises a mixture of nitric acid, hydrofluoric acid, and water. In such embodiments, the nitric acid and hydrofluoric acid are provided in a molar ratio ranging from about 0:1 to about 15:1, from about 0:1 to about 10:1, etc. (the molar ratio of $HNO_3$:HF). In some embodiments, each of the nitric acid and hydrofluoric acid are provided in a molar ratio of 0:1, 1:0, 1.5:1, 3:1, 5:1, 6:1, 7:1, 8: 1, 9:1, 10:1, 11:1, etc. (the molar ratio of $HNO_3$:HF). In some embodiments, the activating step 115 comprises Kroll's reagent (2% HF, 10% $HNO_3$, and 88% water). Other acids and acid solutions are contemplated, including, e.g., a mixture of water and hydrochloric acid in a molar concentration from about 0.005 M to about 1M, from about 0.5M to about 1M, from about 0.005M to about 0.01M, from about 0.01M to about 0.1M, from about 0.05M to about 0.1M. In some embodiments, the acidic treatment of a 3D printed device forms sub-micron surface features indicative of fine surface roughness, which can be useful for promoting biological functions e.g., cell adhesion, proliferation, differentiation or osseointegration.

In some embodiments, the activating step 115 comprises treating the surface of a porous metal coated or porous metal device for about 10 minutes to about 180 minutes with low acid concentrations in pure water, e.g., 0.01-0.1M HF, or mixed acid solutions with molar ratios of $HNO_3$:HF of, e.g., 0-0.09 M $HNO_3$ to 0.01M HF or 0-0.9 M $HNO_3$ to 0.1M HF; and for about 1 minute to about 60 minutes for high acid concentrations in water, e.g., 0.1-1M HF, or mixed acid solutions with molar ratios of about 0-10M $HNO_3$ to 0.1-1M HF.

In some embodiments, the activating step 115 comprises treating the surface of the porous coated medical device or the porous 3D printed device in low acid concentrations (e.g., 0.01-0.1M HF; mixed acid solution with molar ratios of $HNO_3$:HF; e.g., 0-0.09M $HNO_3$: 0.01M HF; 0-0.9M $HNO_3$: 0.1M HF) at about 20° C. to about 60° C. for about 10 minutes to about 180 minutes; or in high acid concentrations (e.g., 0.1-1M HF; mixed acid solutions with molar ratios of about 0 to 10M $HNO_3$: 0.1-1M HF) at about 40° C. to about 80° C. for about 2 to about 60 minutes, at about 40° C. to about 50° C. for about 20 minutes to about 50 minutes for acid concentrations (e.g., 0.1-9M $HNO_3$: 0.1-1M HF; 0.1-9M $HNO_3$; 0.01-1M HF).

In some embodiments, the activating step 115 enables the formation of a uniform oxide layer on the surface of the porous metal coating or porous metal device after a subsequent PEO treatment step 125. In some embodiments, the percent of uniformity of the oxide layer relative to the total surface area treated is 99% or greater, 95% or greater, 90% or greater, 85% or greater. In some embodiments, the percent of uniformity of the oxide layer relative to the total surface area treated is in a range of 65% to 100%, or 70% to 95%, or 75% to 90%, or 80% to 95%, or 85% to 90%. In some embodiments, the activating step 115 does not cause significant etching (i.e., removal of material) of the porous coating. Etching can reduce the thickness and surface area of the porous coating and can roughen the surface of a medical implant in an uncontrolled fashion. In some embodiments, the activating step 115 prevents, reduces the occurrence of, or minimizes the etching of the porous coating on the substrate. In some embodiments, the percent of etching of the coating relative to the total surface area treated is 5% or less, or 10% or less, or 15% or less. In some embodiments, the amount of etching to the coating relative to the total surface area treated is in a range of 1% to 5%, or 2% to 10%, or 3% to 15%.

In some embodiments, the method 100 comprises the washing step 120. In such embodiments, the washing step 120 comprises treating the activated porous coated device surface to remove any residual acid remaining from the activating step 115. In some embodiments, the washing step 120 comprises the use of an ultrasonic cleaning device. In some embodiments, the washing step 120 comprises water, including forms of purified water such as deionized (DI) water. In some embodiments, the washing step 120 comprises washing the activated porous coated device with water in an ultrasonic device for about 15 minutes to 60 minutes, or from about 20 minutes to about 30 minutes, etc. In some embodiments, the washing step 120 comprises washing the activated porous coated device in an ultrasonic device using water at a temperature ranging from 30° to 60° C. In some embodiments, the device is not dried after the activating step 115 and the washing step 120, or before the subsequent treatment steps. In some instances, drying the device allows the activated surface to react with the atmosphere, which can result in the formation of a non-uniform oxide scale on the surface, especially when drying for long periods of 3 hours or more.

In some embodiments, the method 100 comprises the electrical treatment step 125. In some embodiments, the electrical treatment step 125 comprises plasma electrolytic oxidation (PEO), a process also referred to as micro-arc oxidation or anodic spark deposition. PEO treatment combines electrochemical and spark treatment in a dilute alkaline electrolyte solution to form an adherent, microporous oxide layer on the surface of metals, including titanium and titanium alloys. The oxide layer is formed by the conversion of the substrate metal into its oxide form, which grows inward and outward from the original metal surface, typically to a thickness in a range of about 0.1 to about 20 μm. In some embodiments, the oxide layer formed on titanium and titanium alloys has a thickness in a range of 0.1 to 20 μm, 0.5 to 18 μm, 2 to 17 μm, 2 to 10 μm, 5 to 15 μm, etc. The typical microstructure of an oxide layer formed on titanium or titanium alloys can include micropores and micro-cracks. In some embodiments, the micropores on the oxide layer have a pore diameter in a range of 0.1 to 5 μm, 0.2 to 4 μm, 0.4 to 3 μm, 0.5 to 2.5 μm, or 0.6 to 2 μm. The resulting oxide layer can have favorable properties, including good biocompatibility, high hardness, wear resistance, and corrosion resistance, however, the specific properties are dependent on the type of the substrate, the electrolyte composition, and the electrical parameters used in the PEO treatment (e.g., the power supply mode: alternating current (AC), direct current (DC), unipolar, or bipolar pulse DC; voltage; current; pulse frequency; duty cycle; treatment time). For example, the potential applied between the electrodes of the electrochemical cell may be pulsed or continuous DC, or in some cases applied as AC.

In various embodiments, the electrical treatment step 125 includes a PEO treatment in an alkaline electrolytic solution. In some embodiments, the step 125 comprises immersing a medical device in the alkaline electrolyte solution and applying an electric current in unipolar pulse direct current (DC) mode to reach the breakdown voltage necessary to create micro-arcs that promote the formation of an oxide layer on the surface of a porous coated, dense, or 3D printed metal medical device. The power supply can be applied to the medical device in a DC, such as a unipolar or bipolar pulse DC mode, after submerging the medical device in the electrolytic solution. In some embodiments, the PEO treatment employs a constant voltage or constant current mode using unipolar or bipolar pulse DC mode. In some embodiments, the electric signal can be in the shape of a sine wave, rectangular wave, pulsed wave, or square wave. As an example, the waveform can be a pulsed square waveform. The electrolytic solution can be maintained at a desired temperature using an external chiller attached with a plate heat exchanger configured to receive heat generated from spark discharges in the electrolytic solution to cool the electrolytic solution and produce a uniform and reproducible oxide layer on the surface of a medical device. In some embodiments, the temperature of the electrolyte is continuously monitored by a wire thermocouple.

In various embodiments, the treatment step 125 comprises a PEO treatment on a porous coated CpTi or titanium alloy device or portion thereof, a dense device or portion thereof, or a 3D printed titanium alloy medical device (e.g., implant) or portion thereof. In some embodiments, the treatment step 125 comprises a PEO treatment on an ABS CpTi porous coated titanium alloy medical device. In some embodiments, the PEO treatment imparts improved bioactivity and osseointegration potential to the medical device (e.g., a porous coated ABS CpTi or dense titanium alloy device, or 3D printed titanium alloy medical device).

In some embodiments, the PEO treatment comprises a bath of electrolyte. In some embodiments, the electrolyte comprises, consists of, or consists essentially of one or more salts. The electrolyte can comprise, consist of, or consist essentially of calcium compounds, including, e.g., calcium acetate, calcium chloride, calcium citrate, calcium oxide, or calcium nitrate. The electrolyte can comprise, consist of, or consist essentially of phosphate compounds or a source of phosphate anion. In some embodiments, the phosphate compound or source of the phosphate is sodium hydrogen phosphate, beta-glycerophosphate, calcium glycerophosphate, calcium hydrogen phosphate, phosphoric acid or potassium hydrogen phosphate. In some embodiments, the electrolyte comprises one or more complexing agents, including, e.g., disodium ethylenediaminetetraacetic acid (2Na-EDTA). The complexing agent can eliminate or minimize the precipitation of calcium phosphate in an electrolyte containing calcium and phosphate compounds. In some embodiments, the electrolyte comprises, consists of, or consists essentially of a combination of calcium, phosphate, and sodium hydroxide or potassium hydroxide compounds; calcium hydroxide and sodium hydroxide or potassium hydroxide compounds; phosphate and sodium hydroxide or potassium hydroxide compounds; or calcium, 2Na-EDTA, phosphate, and sodium hydroxide or potassium hydroxide compounds. In some embodiments, sodium hydroxide or potassium hydroxide is added to adjust the pH of the electrolyte to a value between 7 and 12. In some embodiments, the PEO treatment transforms the surface of the porous CpTi or porous titanium alloy coated on a titanium alloy medical device, the dense metal medical device, or the porous 3D printed metal medical device into an adherent, bioactive oxide layer having, for example, calcium and/or phosphate ions contained in electrolytes utilized in the bath.

In some embodiments, a sequence of adding compounds to prepare the electrolyte comprises: adding a calcium compound to deionized water and allowing the compound to dissolve completely; followed by adding 2Na-EDTA and allowing the complex to dissolve completely. In some embodiments, the sequence further comprises adding a phosphate compound to the solution containing the calcium compound and 2Na-EDTA and allowing the compounds to dissolve completely. In some embodiments, the sequence further comprises adding sodium hydroxide or potassium hydroxide to one of the above solutions.

In various embodiments, the concentration of compounds used for the PEO treatment is about 0.010M to about 0.4M, about 0.050M to about 0.4 M, about 0.050M to about 0.3M, or about 0.050M to about 0.13M for calcium acetate; about 0.010M to about 0.4M, about 0.050M to about 0.3M, or about 0.050M to about 0.13M for Na-EDTA; about 0.01M to about 0.2M, about 0.03 to about 0.2M, or about 0.03M to about 0.06 M for sodium hydrogen phosphate $(NaH_2PO_4 \cdot 2H_2O)$; and about 0.1M to about 1M, or about 0.2M to about 0.5M for potassium hydroxide.

In various embodiments, the PEO treatment is configured to generate spark discharges over time and is categorized by an initial stage and a main electrolysis stage. In some embodiments, the initial stage is comprised of one or more pre-plasma processes, including, e.g., bubble formation, followed by a series of anodization stages with increasing voltage from zero volts to the breakdown voltage. In various embodiments, the breakdown voltage measured for the PEO treatment for a porous sintered bead coated device is in a range of about 250V to about 280V, for a dense medical device in a range of about 150V to about 200V, and for a 3D printed device is in a range of about 150V to about 200V. The formation of micro-arcs and/or spark discharge is necessary to form an oxide layer that is feasible above the breakdown voltage. Below the breakdown voltage, plasma discharge does not occur, and a thin anodic type of oxide layer may be formed on the surface of titanium metal or alloy.

In some embodiments, the mean voltage in the main electrolysis stage is, for example, from about 150V to about 800V, about 200V to about 500V, about 300V to about 600V, about 400V to about 500V, or about 200V to about 350V. In some embodiments, the mean voltage in the main electrolysis stage is, for example, about 150V, about 200V, about 260V, about 300V, about 320V, about 350V, about 380V, about 450V, about 500V, or about 600V. The mean voltage used for the electrolysis can be important depending on the chemical composition of the substrate or the architecture of the porous coating or porous medical device. At certain voltages, for example, the substrate or coating on the substrate may crack.

In various embodiments of the step 125, the time duration of the pre-plasma electrolytic oxidation processes (initial stage) for a metal medical device after surface activation treatment (step 115) may be from about 10 seconds to about 2 minutes, about 35 seconds to about 2 minutes, about 40 seconds to about 1 minute, about 1 minute to about 2 minutes, etc. The treatment time in the main plasma electrolysis of porous coated device can be from about 3 minutes to about 30 minutes, about 3 minutes to 5 minutes, about 5 minutes to about 8 minutes, about 10 minutes to about 30 minutes, about 20 minutes to about 30 minutes, about 10 minutes to about 20 minutes, about 8 minutes to about 15 minutes, etc. In some embodiments, the PEO treatment time for a porous coated medical device should not be too short because a non-uniform coverage of the oxide layer may be obtained and/or the oxide layer thickness may be insufficient. In some embodiments, the treatment time for the main plasma electrolysis depends upon the surface area of the metal medical device. For example, a large device with a porous coating or a porous device have a relatively high surface area compared to a smaller porous coated, porous device, or dense implant and therefore may need a longer treatment time.

In some embodiments, the PEO treatment of the medical device is performed at a duty cycle of about 3% to about 30%, about 10% to about 30%, about 20% to about 30%, or about 15-20%. A PEO treatment performed at a higher duty cycle may be detrimental to the porous coating due to the large power in a single cycle of the higher duty cycle.

In various embodiments, the temperature of the electrolytic solution used for the PEO treatment of the medical device is maintained at a predetermined value by external chiller attached with a plate heat exchanger. The temperature, for example, may be in the range of about 15° C. to about 70° C., about 15° C. to about 60° C., about 15° C. to about 50° C., about 20° C. to about 30° C., or below 35° C.

In some embodiments, the PEO treatment of the medical device is performed using unipolar pulse direct current (DC). In such embodiments, the frequency of the pulses is in a range from about 5 Hz to about 5000 Hz, from about 5 Hz to about 50 Hz, from about 100 Hz to about 700 Hz, from about 250 Hz to about 500 Hz, from about 250 Hz to about 400 Hz, from about 400 Hz to about 1000 Hz, from about 500 Hz to about 1500 Hz, from about 650 Hz to about 3000 Hz, from about 2000 Hz to about 3000 Hz, from about 3000 Hz to about 5000 Hz, etc.

In some embodiments, the electrical signal for the PEO treatment is applied to the medical device for a period lasting between about 0.1 milliseconds to about 40 milliseconds. For example, the electrical signal may be applied to the medical device at a frequency of 500 Hz for 0.4 milliseconds or at a frequency of 650 Hz for 0.32 milliseconds.

In some embodiments, the method 100 comprises the washing step 130, which comprises washing the oxidized surface of the medical device to remove any ions that may have been physically adsorbed on the surface during the treatment step 125. In some embodiments, the washing step 130 comprises washing the oxidized surface of the medical device with water (e.g., DI water) for a period lasting from about 5 minutes to about 240 minutes, about 10 minutes to about 180 minutes, about 20 minutes to about 120 minutes, about 30 minutes to about 60 minutes, etc., using an ultrasonic cleaning device. For the porous coated and porous medical devices oxidized in lower concentration electrolytes (e.g., in 0.01 to 0.1M calcium acetate, 0.01 to 0.05M sodium hydrogen phosphate, and 0.01 to 0.1M 2Na-EDTA), the duration of the washing step of the oxidized medical device is in a range of from about 3 minutes to about 60 minutes. For the porous coated or porous medical devices oxidized in a solution of high concentration electrolytes (e.g., 0.1 to 0.4M calcium acetate, 0.031 to 0.2M sodium hydrogen phosphate, and 0.1 to 0.4M 2Na-EDTA), the duration of the washing step of the oxidized medical device is in a range of from about 15 minutes to about 180 minutes. In some embodiments, the washing step 130 comprises heating the water to a temperature of 30° C. to 50° C., for about 5 to 20 minutes, inside an orbital shaker with a shaking speed of about 40 rpm to about 180 rpm. In such embodiments, the conditions provide an efficient washing step to remove water soluble salts that may have been physically adsorbed on the medical device after the PEO treatment step 125.

In some embodiments, the method 100 comprises the activation step 135. In some embodiments, the activation step 135 comprises treating the oxidized medical device (e.g., porous coated device) to provide and/or increase the concentration of surface hydroxyl groups. In some embodiments, the activation step crystallizes the surface of the oxide layer to form bioactive compounds that can facilitate bone regeneration. In some embodiments, the hydroxyl groups facilitate the ionic interactions between the surface of the treated device and antimicrobial or bioactive compounds, including, e.g., calcium phosphates, hydroxyapatite, sodium titanates, and/or calcium titanates. In some embodiments, the hydroxyl groups facilitate an effective deposit of proteins, growth factors, peptides, compounds, and/or metal ions. Hydroxyapatite is useful as a coating component to enhance the initial implant fixation of medical implants (e.g., joint replacements, pedicle screws) because it is chemically similar to the mineral component of bone. In some embodiments, the sub-micron sized hydroxyapatite increases osteoblast adhesion and bone regeneration.

In some embodiments, the activation step 135 comprises a treatment of the oxidized porous coated, dense, or 3D printed medical device with an alkaline, or basic, solution to obtain a bioactive surface. In this context, "basic" refers to the components and/or pH of the solution. In some embodiments, the activation step 135 includes submerging the oxidized medical device in a bath of the alkaline solution. In some embodiments, the alkaline solution comprises sodium hydroxide (NaOH), potassium hydroxide (KOH), or ammonium hydroxide ($NH_4OH$). In some embodiments, the activation step 135 comprises a treatment of the oxidized and washed medical device with one or more solutions comprising sodium hydroxide (NaOH), potassium hydroxide (KOH), ammonium hydroxide ($NH_4OH$), hydrochloric acid (HCl), water, or a sequential treatment of the medial device with a NaOH or KOH solution followed by a HCl solution, or with a NaOH solution followed by a water solution. In some embodiments, the solutions are warmed prior to their use in the activation step 135. In some embodiments, the treatment of the oxidized surface with an NaOH solution can activate the oxide layer comprising bioactive elements or phases to enhance the crystallinity of bioactive phases and/or form nanoscale and/or microscale structures on the surface that enhance the biological activity of the medical device and therefore promote osseointegration and bone formation in a subject.

In some embodiments, the activation step 135 comprises submerging the oxidized medical device in a NaOH solution at a concentration of about 0.01M, 0.05M, 0.1M, 0.25M, 0.5M, 0.75M, 1M, 2M, 3M, 4M, or 5M. In some embodiments, the activation step 135 comprises submerging the oxidized medical device in a HCl solution at a concentration of about 0.005M, 0.01M, 0.1M, 0.5M, or 1M. In some embodiments, the activating solution in step 135 includes a hot water treatment at a temperature in the range of from about 40° C. to about 80° C.

In some embodiments, the thickness of the bioactive surface on the microporous oxide layer formed by activation step 135 can be in the range of 0.1 μm to 2 μm.

In some embodiments, the bioactivity and bone regeneration capability of the medical device can be enhanced by a subsequent treatment after the activation step 135. In some embodiments, the bioactivity and bone regeneration capability of the medical device can be enhanced by mixing one or more bioactive compounds comprising calcium, phosphorous, zinc, strontium, silicon, gallium, magnesium, lithium, or combinations thereof with the basic solution used in the activation step 135. In some embodiments, a subsequent treatment after the activation step 135 involves soaking the activated device with the bioactive compounds at varying concentration to obtain improved bioactivity via ionic exchange mechanisms.

In some embodiments, the microstructure of the bioactive surface comprising bioactive phases on the surface of the oxidized medical device is in the form of a nanofibrous network, nano-to-micro sized particles, a composite of the microstructures of the nanofibrous network and nano-to-micro sized particles, or a film of hydroxyapatite and composite of nanofibrous network and nano-to-micro sized particles. The microstructures, independent of one another, can have varying dimensions and spatial distribution. In some embodiments, the composition of the nanofibrous network comprises sodium titanate, calcium titanate, and/or other bioactive elements or phases containing a composition having strontium, zinc, gallium, magnesium, lithium, or combinations thereof. In some embodiments, the nano-to-micro sized particles or plate structures comprise calcium phosphates, amorphous hydroxyapatite, or having hydroxyapatite with varying crystallinity. In some embodiments, the nanostructures can be doped or incorporated with antibacterial elements or compounds such as iodine, silver, copper, or zinc. The formation of nanostructures on the medical device can increase the surface area, which in turn will increase the interaction of proteins, cells, and growth factors with the surface of treated medical device. In such embodiments, the modified microstructures provide improved surface properties for enhancing bone healing and early osseointegration.

In various embodiments, an alkaline (e.g., NaOH) treatment of the surface of a porous coated ABS CpTi, plasma sprayed CpTi or 3D printed Ti alloy medical device in the activation step 135, after step 125 when the surface incorporates calcium phosphates (CaP) or hydroxyapatite, results in the formation of composite microstructure of nanofibers and hydroxyapatite crystals on the surface of nanofibrous network and within the micro-porous oxide layer with varying crystallinity, as shown, for example, in FIGS. 7A-7F and FIGS. 8A-8D. In some embodiments, the nanofibers are sodium titanate, formed into calcium titanate by ion exchange mechanism, or a combination of sodium and calcium titanates. In some embodiments, the titanates are formed by a chemical reaction between $TiO_2$ with $OH^-$ ions from the NaOH solution. Without being bound by a particular scientific theory, the $TiO_2$ is attacked by $OH^-$ ions in the NaOH solution to form hydrogen titanate $(HTiO_3)^-$ as shown below in Equation 1.

$$TiO_2 + OH^- \square (HTiO_3)^- \qquad \text{(Equation 1)}$$

In some embodiments, the negatively charge hydrogen titanate interacts with $Ca^{2+}$ or $Na^+$ ions in the solution to form sodium or calcium titanates per the Equations 2 and 3 below.

$$2n\,Na^+ + n(HTiO_3)^- + n\,OH^- \square [Na_2-Ti-O_3]_n \cdot n\,H_2O \qquad \text{(Equation 2)}$$

$$m\,Ca^{2+} + m(HTiO_3)^- + m\,OH^- \square [Ca-Ti-O_3]_m \cdot m\,H_2O \qquad \text{(Equation 3)}$$

In some embodiments, the titanate nanofibers on the surface interact with phosphate and hydroxyl ions in the solution or on the surface of the treated medical device to nucleate calcium phosphate (e.g., hydroxyapatite) crystals on the nanofibers. In such embodiments, the nanostructures can enhance the surface area of a medical device and can provide enhanced bioactivity that can facilitate better bone in-growth and bone on-growth characteristics for the porous device. In some embodiments, treatment with a NaOH solution will result in the formation of OH groups on the surface of the oxide layer along with other structures, including calcium phosphate or hydroxyapatite with varying crystallinity that can be a supporting substrate for the immobilization of antibacterial compounds such as iodine. In some embodiments, the oxygen rich structures are favorable for the adsorption, cell adhesion, proliferation, and/or differentiation, of proteins and other biological compounds that can stimulate bone regeneration.

In some embodiments, the activation step 135 comprises submerging the oxidized medical device in a solution described above in a static condition or a condition of agitating the solution (using, e.g., an orbital shaker at speeds in the range of about 40 rpm to about 180 rpm) to ensure uniform activation of the surface of complex 3D porous medical device.

In some embodiments, the activation step 135 comprises submerging the oxidized medical device in a solution described above at a temperature in the range of about 30° C. to about 60° C., about 50° C. to about 60° C., about 60° C. to about 80° C., about 60° C. to about 70° C., about 70° C. to about 95° C., or at a temperature of about 60° C., about 65° C., about 70° C., about 75° C., or about 80° C.

In some embodiments, the activation step 135 comprises submerging the oxidized medical device in the solution for a period of time in the range of about 30 seconds to about 48 hours, about 30 seconds to about 10 minutes, about 10 minutes to about 24 hours, about 10 minutes to about 12 hours, about 30 minutes to about 24 hours, about 30 minutes to about 12 hours, about 30 minutes to about 6 hours, about 30 minutes to about 1 hour, etc.

In some embodiments, the method 100 comprises a heat treatment step. In some embodiments, the heat treatment step is after the treatment step 125. In some embodiments, the heat treatment step is after the activation step 135. In some embodiments, the heat treatment step is after the activation step 135 and a subsequent bioactivation treatment step. In some embodiments, the heat treatment is carried out in air or under vacuum. In some embodiments, the heat treatment facilitates the crystallization of particles, or the conversion of amorphous particles into crystalline particles, or an increase in the hardness of the medical device (making it more resistant to wear or scratches). An ordered nature of the crystal structures can enhance the biological activity of the medical devices. In some embodiments, the temperature for the heat treatment is in a range of about 250° C. to about 800° C., about 250° C. to about 500° C., about 300° C. to about 700° C., about 400° C. to about 700° C., about 450° C. to about 600° C., or about 600° C. to about 800° C. In some embodiments, the duration of heat treatment is in the range of about 1 minute to about 24 hours, including, for example, about 10 minutes, about 30 minutes, about 1 hour, about 2 hours, about 3 hours, about 4 hours, about 6 hours, or about 12 hours.

In some embodiments, the method 100 comprises the treatment step 140. In some embodiments, the treatment step 140 is after the treatment step 125. In some embodiments, the treatment step 140 is after the activation step 135. In some embodiments, the treatment step 140 is an iodine treatment, which comprises impregnating the porous surface of the medical device with iodine (I$_2$), an iodine containing compound, or an iodide containing compound (i.e., a positive or negative iodide ion), (collectively referred to herein as "iodine"). Iodine, and various forms thereof, have antimicrobial properties. For example, povidone iodine is commonly applied to a patient's skin before surgery. In the iodine treatment step 140, impregnating iodine on the surface of the device provides an antibacterial device configured to resist the formation of a bacterial colony and/or infections caused by the bacteria.

In various embodiments, the iodine may be derived from an inorganic iodine compound or an organic iodine compound. Inorganic iodine compounds include, for example, silver iodide, copper iodide, potassium iodide, nickel iodide, iron iodide, tin iodide, iodine chloride, and copper iodide. Organic iodide compounds include, for example, saturated hydrocarbons and their derivatives, such as methyl iodide, ethyl iodide, propyl iodide, butyl iodide, and isopropyl iodide; unsaturated hydrocarbons and their derivatives, such as vinyl iodide, allyl iodide, crotyl iodide, propargyl iodide, and phenylacetylene iodide; aromatic hydrocarbons and their derivatives, such as iodobenzene, benzyl iodide, benzoyl iodide, phenacyl iodide, xylylene iodide, phthalein iodide, hydroquinone iodide, and cyclodextrin-iodine inclusion compounds; heterocompounds, such as trimethylsulfonium iodide and tri phenyl-sulfonium iodide; and polymers derived from heterocompounds, such as polyvinyl pyrrolidone iodine (Povidone Iodine) and polyvinylphthalimide iodine. In some embodiments, the iodine compound is biocompatible and safe to use with human subjects.

In some embodiments, an aqueous solution of the iodine compound is used (e.g., a solution comprising povidone iodine). In some embodiments, the iodine solution comprises iodine in a range of 0.01% to 10%, 0.04% to 0.5%, 1% to 5%, 1% to 10%, 2% to 8%, 3% to 8%, 4% to 9%, 5% to 8%, 6% to 10%, etc. In some embodiments, the medical device is submerged in a bath containing the aqueous iodine solution. In such embodiments, the soaking temperature is in a range of about 25° C. to about 80° C., about 25° C. to about 60° C., about 25° C. to about 40° C., or any specific temperature within a range, including, for example, about 25° C., about 40° C., about 50° C., about 60° C., etc. In some embodiments, the medical device is a dense, porous coated device, or a 3D printed device, and the device is submerged in an iodine solution for about 30 seconds to about 24 hours.

In some embodiments, an amount of iodine on a PEO-treated medical device can be increased by forming thick oxide layers on the surface of medical devices that have a higher concentration of hydroxyl groups compared to thin oxide layers with a lower concentration of hydroxyl groups. In some embodiments, thick oxide layers can be formed by PEO treatment of medical devices in electrolytes containing 0.1-0.4M calcium acetate, 0.1-0.4M 2Na-EDTA and 0.01-0.2M sodium hydrogen phosphate. In some embodiments, the iodine treatment is performed after the PEO treatment 125. In some embodiments, the iodine treatment is performed after the alkaline activation step 135. In some embodiments, the iodine treatment is performed after the alkaline activation step and a subsequent heat treatment. Heat treatment of a medical device comprising crystalline and nanostructured phases or compounds can control the release rate of antibacterial compounds. In some embodiments, antibacterial compounds can react with bioactive elements, phases, or compounds to form compounds containing both bioactive and antibacterial elements or phases that can be beneficial for maintaining bone growth and preventing infection and for controlling the release of ions.

In some embodiments, the medical device is submitted to electrodeposition conditions comprising submerging the medical device or treated medical device according to one or more steps of FIG. 1, in the aqueous iodine solution and applying a voltage in the range of 100-200V for about 3 to 60 minutes at room temperature to 40° C.

In some embodiments, the method 100 comprises the washing step 145. In some embodiments, the washing step 145 comprises a washing substep and a drying substep. In such embodiments, washing the iodine-impregnated device removes excess iodine, any iodine that had not adhered to the device, and/or shows discoloration. The washing substep can utilize any suitable washing solution. In some embodiments, for example, the washing solution comprises water, such as deionized (DI) water. The washing method comprises submerging the iodine impregnated device in DI water. The iodine-impregnated device can be washed for any suitable amount of time. In this context, the suitability depends on the amount of excess iodine present on the device. For example, the device can be washed from about 1 second to about 120 seconds, from about 5 seconds to about 90 seconds, from about 1 minute to about 20 minutes, or from about 1 minute to about 5 minutes, about 1 minute to about 3 minutes, etc. In some embodiments, excess iodine can be removed effectively by submerging the iodine impregnated device in a DI water bath maintained at about 30° C. to 50° C. In some embodiments, following the washing substep, the iodine-impregnated device can be dried so it is ready for use or storage. The washed iodine-impregnated device can be dried in any suitable conditions, including, for example, an oven, an inert room temperature atmosphere, and/or in darkness. In some embodiments, the washed iodine-impregnated device is dried in an oven. In such embodiments, the oven is warmed to a temperature in the range of from about 25° C. to about 75° C., from about 25° C. to about 65° C., from about 25° C. to about 50° C., etc. In some embodiments, the washed iodine-impregnated device is dried for a period ranging from about 5 minutes to about three hours.

EXAMPLES

Various aspects of the processes described above are illustrated through the following examples. The examples should not be read to limit the scope of the claims. In the examples below, various aspects of the acid activation treatment, plasma electrolytic oxidation treatment, alkaline bioactivation treatment, and iodine treatment are presented.

Example 1.1. Commercial ABS (Asymmetric Bead Sintered) CpTi coated on Ti-6Al-4V alloy substrate coupons (substrate size: 25.4 mm in diameter, 6.35 mm in thickness; ABS CpTi coating thickness: about 1 mm) from an implant manufacturer were used as test coupons. FIG. 2A and FIG. 2B show low (100×) and high magnification (250×) SEM images of the surface of an ABS CpTi coupon as received from the manufacturer. The coating comprises irregularly shaped particles fused together to form inter-particle bonds through a sintering process. The ABS CpTi porous coating has a mean pore size of about 250-300 μm with about 60% porosity. An investigation was carried out to determine conditions that can effectively improve the bioactivity of the porous coated medical device comprised of the CpTi coating on a Ti-6Al-4V alloy substrate. The conditions and results of the various experiments are provided in Table 1A and Table 1B below, with reference to the figures.

PEO treatments were performed on the coupons in unipolar pulse DC mode at a constant voltage of 320V, pulse frequencies in the range of 5-5000 Hz, a duty cycle of 20%, for 10 minutes (or 15 or 20 minutes), in an alkaline electrolyte containing 0.06M calcium acetate (CaAc), 0.06M Na-EDTA, 0.03M sodium hydrogen phosphate ("NaP") and 0.2M potassium hydroxide (KOH). The PEO treatments resulted in the formation of a titanium dioxide layer having bioactive elements, phases, and/or compounds present in the electrolyte. The test coupon was connected to the anode and a stainless-steel plate was connected to the cathode. The electrolyte was continuously stirred to allow a uniform reaction around test coupons during the treatment. The electrolyte was cooled using an external chiller connected to a plate heat exchanger. The mean voltage and current readings were taken from an external oscilloscope attached to the anode.

TABLE 1A

Examples for activating step 115 and PEO step 125.

| | | | | | PEO Treatment Electrolyte: 0.06M CaAc, 0.06M EDTA, 0.03M NaP, 0.2M KOH; $V_m$ = 320 V; Duty = 20% | | | Mean Current Measured (A) | |
| | Surface Activation Treatment | | | | | | | | |
| No. | Activating Agent | Temp (° C.) | Time (min) | f (Hz) | Time (min) | Pulse on time (ms) | | Start time | End time |
|---|---|---|---|---|---|---|---|---|---|
| CE1 | none | N/A | N/A | 650 | 10 | 0.4 | | 9 | 8 |
| CE2 | 3M HNO₃ | 60 | 20 | 500 | 20 | 0.4 | | 9 | 5 |
| E1 | 1.5M HNO₃ & 0.5M HF (3:1) | 40 | 20 | 500 | 20 | 0.4 | | 5 | 0.8 |
| E2 | 2.5M HNO₃ & 0.5M HF (5:1) | 40 | 20 | 500 | 20 | 0.4 | | 5 | 0.8 |
| E3 | 3M HNO₃ & 0.5M HF (6:1) | 40 | 20 | 500 | 20 | 0.4 | | 4 | 0.8 |
| E4 | 6.0M HNO₃ & 0.75M HF (8:1) | 40 | 20 | 5 | 10 | 40 | | 2.5 | 1.5 |
| E5 | 6.0M HNO₃ & 0.75M HF (8:1) | 40 | 20 | 10 | 10 | 20 | | 3 | 0.15 |
| E6 | 6.0M HNO₃ & 0.75M HF (8:1) | 40 | 20 | 50 | 10 | 4 | | 3 | 0.15 |
| E7 | 6.0M HNO₃ & 0.75M HF (8:1) | 40 | 20 | 250 | 10 | 0.8 | | 3.5 | 0.2 |
| E8 | 6.0M HNO₃ & 0.75M HF (8:1) | 40 | 20 | 500 | 10 | 0.4 | | 4 | 0.6 |
| E9 | 6.0M HNO₃ & 0.75M HF (8:1) | 40 | 20 | 650 | 10 | 0.32 | | 5 | 0.6 |
| E10 | 6.0M HNO₃ & 0.75M HF (8:1) | 40 | 20 | 800 | 10 | 0.24 | | 5 | 0.8 |
| E11 | 6.0M HNO₃ & 0.75M HF (8:1) | 40 | 20 | 1200 | 10 | 0.2 | | 5 | 1.5 |
| E12 | 6.0M HNO₃ & 0.75M HF (8:1) | 40 | 20 | 1500 | 10 | 0.12 | | 5 | 3 |
| E13 | 9.0M HNO₃ & 1M HF (9:1) | 40 | 15 | 500 | 15 | 0.4 | | 4 | 0.6 |

N/A = not applicable; M = molarity; $V_m$ = mean voltage; f = pulse frequency; Duty = duty cycle.

TABLE 1B

Summary of results for select entries in Table 1A.

Figure 3:
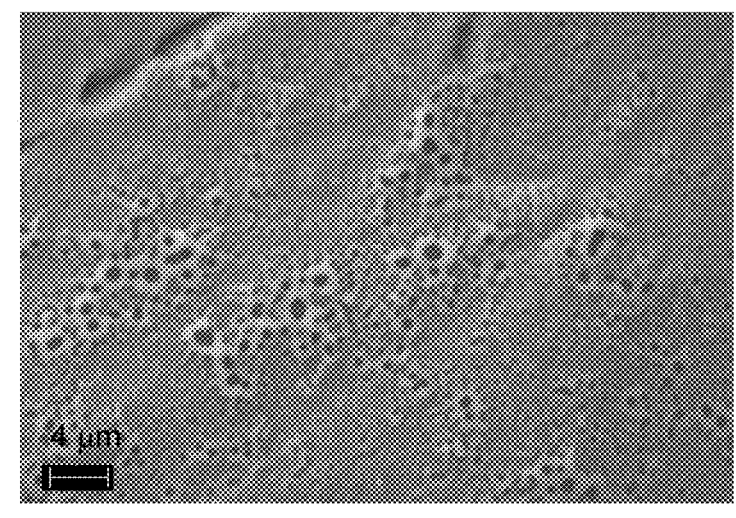
FIG. 3 is an SEM image of the surface of a porous ABS CpTi coated titanium alloy coupon after a plasma electrolytic oxidation (PEO) treatment without a prior acid activation treatment, in Comparative Example 1 (CE1)
Figure 5A:
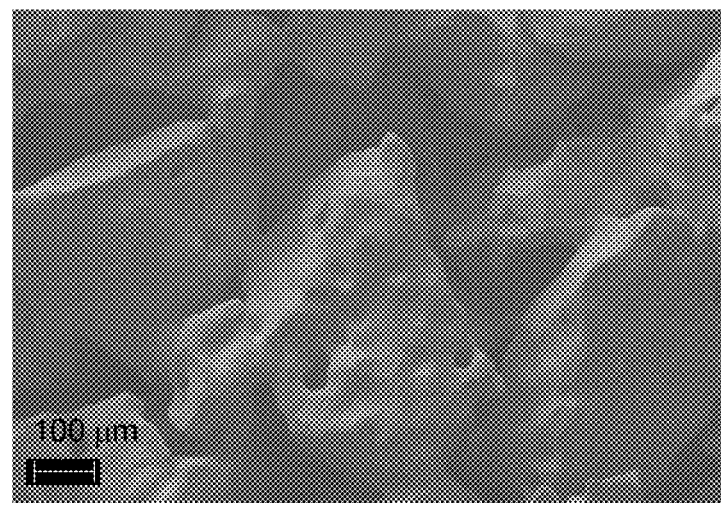
FIG. 5A and FIG. 5B are SEM images of the activated surface of the porous coated ABS CpTi medical device in Example 1.1 processed according to one or more steps of the method of FIG. 1, in accordance with embodiments described herein.

| | Results | |
| No. | Porous Coating After Surface Activation Treatment | Oxide Layer After PEO Treatment |
|---|---|---|
| CE1 | N/A | non-uniform oxide surface FIG. 3 (500X) |
| CE2 | significant etching | rough microstructure with non-uniform oxide layer in some discrete regions |
| E1 | some etching of porous coating | uniform oxide surface |
| E2 | some etching of porous coating | uniform oxide surface |
| E3 | some etching of porous coating FIG. 5A (100X) | uniform oxide surface |

TABLE 1B-continued

Summary of results for select entries in Table 1A.

Results

Figure 5B:
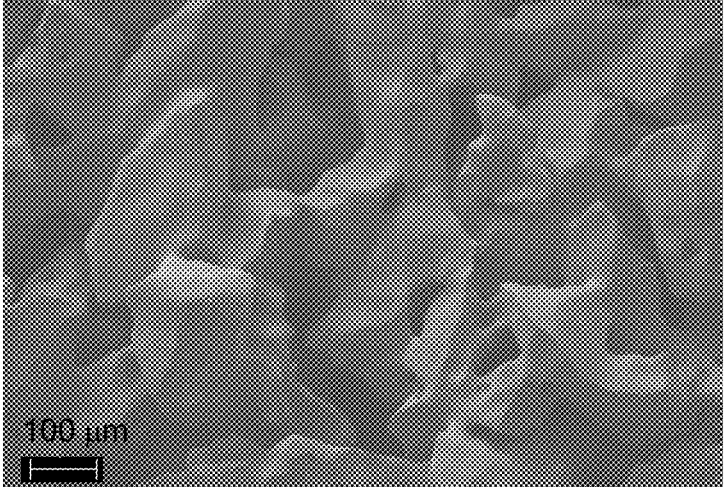
Figures 6A, 6B, 6C:
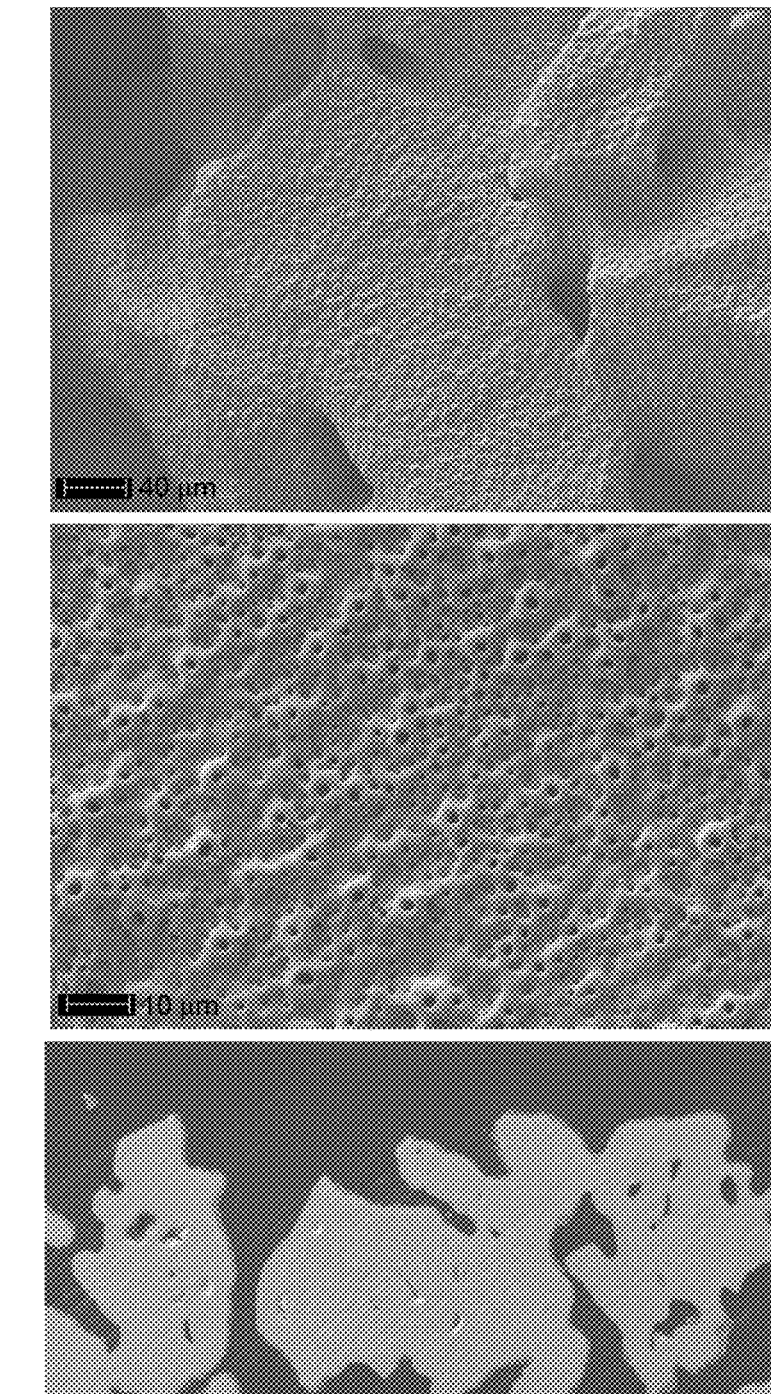
FIG. 6A and FIG. 6B are SEM images of the surface of an oxidized porous ABS CpTi coated medical device in Example 1.1 processed according to one or more steps of the method of FIG. 1, in accordance with embodiments described herein.
FIG. 6C and FIG. 6D are SEM images of a cross-section of the oxidized surface of the porous ABS CpTi coated medical device in FIGS. 6A and 6B.

| No. | Porous Coating After Surface Activation Treatment | Oxide Layer After PEO Treatment |
|---|---|---|
| E8 | significant activation and minimal etching FIG. 5B (100X) | uniform oxide surface FIG. 6A (250X), FIG. 6B (1000X) |
| E13 | minimal etching | uniform oxide surface |

In Table 1A, Comparative example 1 (Entry No. CE1) is the electrical data recorded for a porous coated ABS CpTi coupon after the PEO treatment at a pulse frequency of 650 Hz, duty cycle of 20% for a treatment time of 10 minutes according to step 125, without a prior activating step 115. During the PEO treatment, the electric current across the coated substrate was recorded at the initial time (t=0 min) after reaching a constant voltage of 320V that was maintained until the end of the treatment time. Oxide layer growth was indicated by a decrease in current due to the resistance developed by the insulating oxide layer. For CE1, a high mean current of 9A was measured at the initial time, which decreased only slightly to about 8A throughout the treatment duration. The SEM image in FIG. 3 (magnification 500×) shows regions having minimal and/or non-uniform oxidation. In addition, the measured electrolyte temperature was about 40° C. by end of the treatment (t=10min) due to severe bubbling caused by the high surface tension of the porous coated ABS CpTi coupon. As indicated in Table 1B, the SEM image in FIG. 3 shows the effect of the PEO treatment on the surface of the CE1 specimen, which is a non-uniform oxide layer in terms of the microstructural features. FIG. 3 shows unreacted and minimally reacted regions on the surface of the oxide layer. The reacted regions are shown by irregularly shaped tiny micropores, and the unreacted regions do not show any pores; the combination of which being indicative of non-uniformity of the oxide layer.

High surface tension and/or poor wettability restrict the uniform electrolyte flow inside a porous structure and can result in non-uniform current flow during an electrochemical treatment, therefore leading to non-uniform oxidation within the porous coating. The data for CE1 indicates a relatively large amount of power is required to initiate the PEO treatment, which may be due to the high surface tension and/or poor wettability associated with the three-dimensional network of the porous coated device. A further investigation was carried out to determine conditions that effectively enhance the wettability of the porous ABS CpTi coating with minimal etching of the porous regions.

The acid treatment step 115 was used to address the problem with non-uniformity of oxidized surfaces after a PEO treatment and to activate the porous coated surface by improving the wettability and/or reducing the surface tension. Comparative example 2 (CE2) provides the data for an ABS CpTi coupon activated according to step 115, followed by washing step 120 to remove residual acid on the treated coupon, and a subsequent PEO treatment step 125. For CE2, the acid treatment conditions were 3M HNO₃ in DI water maintained at 60° C. for 20 minutes. As indicated in Table 1B, the acid composition for CE2 resulted in some significant, undesirable etching of the ABS CpTi coating. The measured mean current decreased from 9A at t=0 to about 5A at t=20 minutes, which indicates an incomplete oxidation treatment inside the ABS CpTi porous coating. Each coupon in examples E1-E12 was treated with acid for 20 minutes at 40° C., except for example E13, which was treated in a solution of 9M HNO₃ and 1M HF in a 9:1 molar ratio at 40° C. for 15 minutes.

The activation conditions for the acid treatment step 115 in examples 1-13 (Entry Nos. E1-E13) provided improved results with respect to forming a uniform oxide layer after the PEO treatment step 125. But certain acid solutions were found to be too harsh for the surface of ABS CpTi porous coated device and resulted in undesirable etching of the porous coating. In E1, the activating solution contained 1.5M HNO₃ and 0.5M HF, in a 3 to 1 molar ratio. In E2, the activating solution contained 2.5M HNO₃ and 0.5M HF, in a 5 to 1 molar ratio. In E3, the activating solution contained 3M HNO₃ and 0.5M HF, in a 6 to 1 molar ratio. For E1, E2, and E3, the activating conditions resulted in significant change to both the initial and final currents recorded during the PEO treatment. The initial current was measured at 5A, 5A, and 4A, respectively, which gradually decreased to reach the final current at 0.8A in each example. As indicated in Table 1B, each of the conditions in E1-E3 caused some etching of the ABS CpTi porous coating. Surprisingly, it was discovered that the relative amount of etching decreased as the molarity of HNO₃ was increased from 1.5 M in E1 to 3M in E3 (the molarity of HF being fixed at 0.5M). FIG. 5A is an SEM image of E3 taken after the activating step 115. FIG. 5A shows bigger particles with dimples that are revealed after etching of smaller particles that were observed on the surface of the coupon prior to the acid activation step (FIG. 2A), demonstrating an undesired amount of etching and a decrease in volume of the porous coating.

Figure 4:
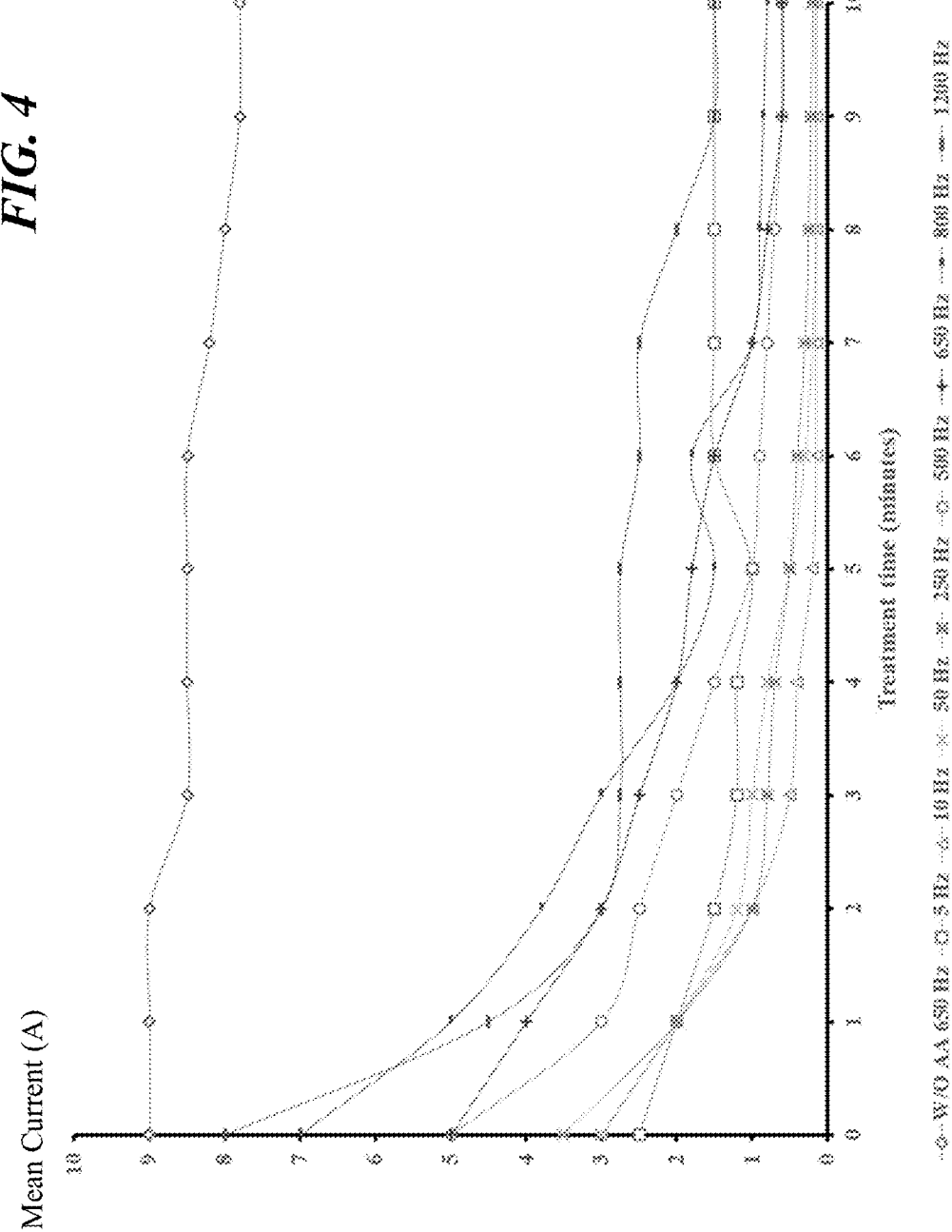
FIG. 4 is a diagram showing the variation in mean current measured during a PEO treatment of a porous ABS CpTi coated titanium alloy medical device at different pulse frequencies, in accordance with embodiments described herein.

To retain adequate roughness of the ABS CpTi coated surface for initial implant fixation with bone, minimal etching is needed. To this end, various molar ratios of HNO₃ and HF solutions were examined (Table 1A). In E8, the activating solution contained 6M HNO₃ and 0.75M HF, in an 8 to 1 molar ratio. FIG. 5B is an SEM image of the microstructure of the coupon after acid activation step 115 in example E8. The SEM image shows the coupon experienced minimal etching by the acid activation treatment since the irregular shape and porous structures of the original, as received ABS CpTi particles were retained. In E13, the activating solution contained 9M HNO₃ and IM HF, in a molar ratio of 9 to 1, and a treatment time of 15 minutes. For E8 and E13, the initial and final currents were recorded during the PEO treatment. The conditions for E13 (Table 1A) resulted in minimal etching and a uniform oxide layer on the surface of porous coating after the subsequent PEO treatment. The initial currents were measured at 4A for each and gradually decreased over time to a final current of 0.6A. FIG. 4 shows the mean current measured over the PEO treatment time of 10 minutes at varying pulse frequencies. The current stabilized to about 0.6A after five minutes and remained unchanged until the end of the treatment time (t=10 min) indicating almost completion of the oxidation reaction.

In examples, for ABS CpTi coupons treated with acid composition of 6M $HNO_3$, 0.75M HF in E4 or 9M $HNO_3$ 1.0M HF in E13, the temperature of electrolyte at the end of subsequent PEO treatment was about 19-20° C., compared with about 35-40° C. in CE1 and about 25° C. in E2 at the end of PEO treatment (t=20 min). High measured currents (about 8-9A) throughout PEO treatment in CE1 resulted in severe bubbling at the surface of ABS CpTi coupon that increased the temperature of the electrolyte, mainly due to high surface tension of porous coupon. Acid treatment step in E8 and E13 seems to reduce the surface tension and subsequent PEO treatment showed a gradual decrease in electric current over time (FIG. 4) with a small rise in temperature of electrolyte from 17° C. at t=0 to about 20° C. measured at t=10 minutes. It was determined that a longer PEO treatment time (e.g., t=20 min) is unnecessary for these preferred acid compositions in E8 and E13 for forming uniform oxide layer in subsequent PEO step 125.

For examples E4-E12, the activating solution contained 6M $HNO_3$ and 0.75M HF, in an 8 to 1 molar ratio; and the PEO treatment included pulse frequencies of 5 Hz, 10 Hz, 50 Hz, 250 Hz, 500 Hz, 650 Hz, 800 Hz, 1200 Hz, and 1500 Hz at a constant voltage of 320V, a duty cycle of 20%, and a treatment time of 10 minutes, as summarized in Table 1A. In E5, E6, E7, E8, E9, and E10, the PEO treatments utilized a frequency of 10 Hz, 50 Hz, 250 Hz, 500 Hz, 650 Hz, and 800 Hz, respectively, and a pulse ON time of 20 ms, 4 ms, 0.8 ms, 0.4 ms, 0.32 ms, and 0.24 ms, respectively. As shown in FIG. 4, the current decreased gradually over time, by about 85-95%, in each of E5 to E10. The gradual decrease in current, or a significant decrease in current, is indicative of a complete or near complete oxidation of the surface of ABS CpTi coating. For E11 and E12, the current was reduced by about 70% at 1200 Hz and about 40% at 1500 Hz, respectively, which is likely due to a shorter time for oxidation resulting from lower pulse ON time of 0.2 ms at 1200 Hz and 0.12 ms at 1500 Hz. In E4, the current was reduced by 40% at 5 Hz, which is indicative of a non-uniform and/or insufficient oxidation of the coating due to a pulse ON time of 40 ms that is too high. The pulse frequencies of 5 Hz or lower and 1500 Hz or higher demonstrated an insignificant reduction in current, which is indicative of a non-uniform oxidation, and therefore are not suitable parameters for commercial application. The gradual decrease in current, or significant decrease in current, at frequencies 10 Hz to 1200 Hz can be beneficial for forming uniform oxide layers on medical devices.

In example E8, the SEM images at low magnification (250×) in FIG. 6A and at high magnification (1000×) in FIG. 6B show the surface of ABS CpTi coupon after the acid treatment in a solution comprising 6M $HNO_3$ and 0.75M HF, at 40° C., for 20 minutes, followed by a PEO treatment at 320V, 500 Hz pulse frequency, 20% duty cycle, for 10 minutes. A uniform microporous titanium dioxide layer with micropores in the range of about 0.1 μm to about 3 μm, with a mean pore size of 1.5 μm, was formed over the surface of ABS CpTi porous coated coupon. Elemental composition data obtained by energy dispersive spectroscopy (EDS) showed bioactive elements having about 5 at. % Ca and 4.3 at. % P, in addition to Ti, O, and about 1 at. % Na. A uniform oxide layer with a mean thickness of about 6 μm having bioactive elements was formed in E8.

During use, bone in-growth can be promoted if a uniform bioactive layer can be formed within the porous medical device. To investigate the uniformity of the oxide layer within a porous ABS CpTi coated coupon, a cross-section of the PEO treated coupon at 650 Hz in E9 was obtained by embedding the oxidized coupon in resin followed by sectioning in a perpendicular direction by a slow speed saw machine with a diamond blade. The sectioned oxidized coupon was grounded sequentially using 400, 800, 1000, 2500, and 4000 grit papers, and then polished sequentially using an alumina solution with grit sizes of 1 μm, 0.3 μm, and 0.05 μm. Each grinding and polishing condition was carried out for 5 minutes using an automatic grinding machine under running tap water to obtain a mirror polished cross-section of a PEO treated ABS CpTi test coupon.

FIG. 6C shows an SEM image of the cross-section of resin embedded ABS CpTi porous coated coupon after the acid activation and subsequent PEO treatment in E9. An oxide layer thickness in the range of about 5 μm to 7.5 μm, with a mean layer thickness of 6 μm, is observed to be uniformly formed on the surface of the ABS CpTi coupon. Due to the irregular shape of ABS CpTi particles, it was possible to observe the microporous oxide layer within the ABS CpTi porous coating, which was not sectioned by the diamond blade.

Figure 6D:
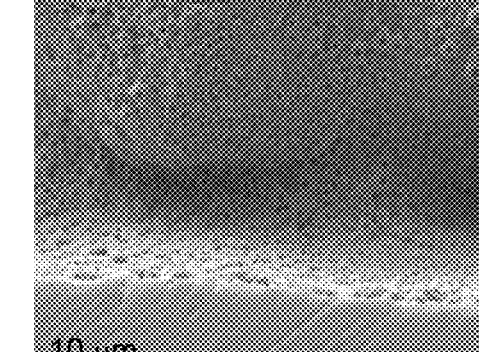

FIG. 6D shows an SEM image of the surface of a microporous oxide layer on the surface of an irregular ABS particle on the surface of a Ti alloy substrate. The thickness of the oxide layer on the surface of Ti alloy device beneath the oxidized ABS CpTi coating was about 3 μm. The top surface and cross-sectional SEM analyses indicate a uniform bioactive oxide layer throughout ABS CpTi porous coated medical device can be obtained after the acid activation step 115 and subsequent PEO step 125. The formation of a uniform oxide layer having bioactive elements or phases within a porous medical device is desired because it will encourage a superior bone in-growth and early osseointegration—objectives that are typically missing in commercial ABS CpTi medical devices due to the bio-inertness of titanium and due to a lack of existing coating methods of plasma spraying or any other surface treatment methods.

Example 1.2. ABS CpTi coupons were subjected to alkaline treatments after sequential acid activation and PEO treatments to determine the effect of alkaline treatment on the microstructure and chemical composition of the surface of the coupons. Each coupon was degreased for 30 minutes using a three-step wash, according to step 110, activated with an acid solution of 6.0M $HNO_3$, 0.75M HF, and DI water at 40° C. for 20 minutes inside an orbital shaker with a speed of 80 rpm, according to step 115, washed in an ultrasonic device for 15 minutes to remove any residual acid, and subjected to PEO treatment, according to step 125. Each PEO-treated coupon was washed in pure water according to step 130 in an ultrasonic device for 15 minutes to remove any adsorbed salts of electrolytic solution. The oxidized surfaces of the coupons were then activated according to step 135 using an alkaline solution. Each coupon was then rinsed with deionized water for 1 minute and dried in an electric oven maintained at 65° C., according to step 145. SEM images and the elemental composition of each coupon were obtained by field emission-SEM microscope at an accelerating voltage of 10 kV.

In CE3, the coupon was subjected to the PEO treatment without a subsequent alkaline solution treatment and used as a control. The other coupons in the series were subjected to the PEO treatment and a treatment with a sodium hydroxide (NaOH) solution (E14, E15, E16). The elemental composition of carbon, titanium, oxygen, calcium, sodium, and phosphorus was determined for each coupon using energy-dispersive x-ray spectroscopy (EDS). The ratio between the calcium and phosphorus (based on atomic percent) was relied on to indicate the effectiveness of the treatments with respect to forming calcium phosphates with varying crystallinity. As a point of reference, hydroxyapatite ($Ca_{10}(PO_4)_6(OH)_2$) is a crystalline form of calcium phosphate that is present in human bone and has a calcium to phosphorus ratio of 1.67. Notably, the Ca/P ratio in the oxide layer is an important criterion for the prediction of bioactivity of the implant surface. When the Ca/P ratio is very high, for example 2 or more, the mechanical strength is poor, and when the Ca/P ratio is less than 1.5, the bioactivity is lower.

Figure 7A:
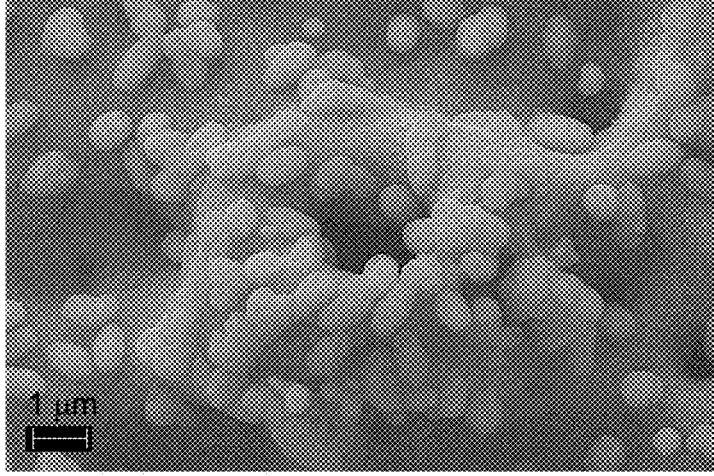
FIG. 7A, FIG. 7B, FIG. 7C, FIG. 7D, FIG. 7E, and FIG. 7F are SEM images of the activated surface of the porous ABS CpTi coated medical device in Example 1.2 processed according to one or more steps of the method of FIG. 1, in accordance with embodiments described herein.
Figure 7B:
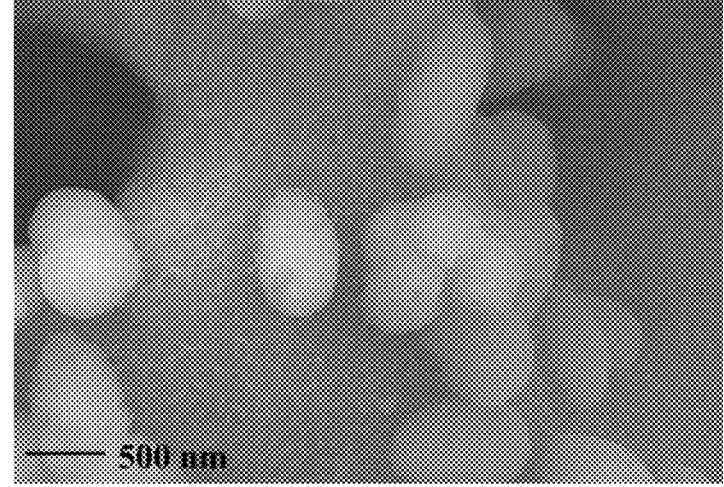

The PEO treatment parameters included a voltage of 320 volts, a pulse frequency of 10 Hz, 50 Hz, 500 Hz, 650 Hz, or 1500 Hz, a duty cycle of 20%, a treatment time of 10 minutes, and an alkaline electrolyte of 0.06M CaAc, 0.06M Na-EDTA, 0.03M NaP, and 0.2M KOH maintained at 16-20° C. The alkaline treatment conditions included a NaOH solution comprising 30 mL of 0.5M NaOH heated at 60° C. for 1, 12, or 24 hours. The elemental composition of the surface was determined for C, Ti, O, Ca, P and Na at five random locations and range of Ca/P ratios were determined. The experimental conditions and SEM/EDS results are shown in Table 2, with reference to the relevant figures.

the PEO treatment (500 Hz) resulted in microstructural inhomogeneity, as indicated by the non-uniform distribution of embedded HA particles shown in the SEM image in FIG. 7A (10,000×) and FIG. 7B (25,000×). The PEO treatment (650 Hz) and alkaline treatment in E15 resulted in the formation of a nanofibrous network overlaid with a uniform distribution of embedded HA particles sized about three times smaller (FIG. 7C at 10,000× and FIG. 7D at 25,000×) than the HA particle sizes provided in example E14. Extending the alkaline (NaOH) treatment to 24 hours in E16 resulted in the production of even smaller HA particles: most particles were around 130 to 160 nm; most particles were observed to be round. The round particles in E16 seem to form a film that was observed in discrete regions, as seen in the SEM image in FIG. 7E (10,000×) and FIG. 7F (25,000×). The combination of the SEM microstructures and Ca/P ratios in examples E14 and E15 revealed the non-uniform microstructures led to a wide range in crystallinity in E14 when a prior PEO step was performed at 500 Hz and the uniform microstructures lead to uniform crystallinity in E15 when a prior PEO step was performed at 650 Hz. PEO treatments at 10 Hz, 50 Hz, and 1500 Hz, followed by 12-hour NaOH treatments yielded a non-uniform micro-

TABLE 2

| | | |
|---|---|---|
| Experiments for the alkaline treatment step 135. | | |
| No. | PEO and Alkaline Treatment Conditions | Results |
| CE3 | PEO treatment (500 Hz, 650 Hz) No alkaline treatment | Ca/P = 1.04-1.14; Na 1.00 at. % |
| E14 | PEO treatment (500 Hz) Alkaline treatment (0.5M NaOH, 12 hours) | Ca/P = 1.50-1.68; Na 3.34 at. % Nanofibers: 25-40 nm HA particles: mixed plate and round in shape, mean length: 700 nm, mean width: 400 nm (FIG. 7A and FIG. 7B) |
| E15 | PEO treatment (650 Hz) Alkaline treatment (0.5M NaOH, 12 hours) | Ca/P = 1.53-1.55; Na 2.23 at. % Nanofibers: 20-30 nm thick HA particles: mixed plate and round in shape mean length: 240 nm, mean width: 150 nm (FIG. 7C and FIG. 7D) |
| E16 | PEO treatment (650 Hz) Alkaline treatment (0.5M NaOH, 24 hours) | Ca/P = 1.62-1.74; Na 3.04 at. % 25-40 nm thick nanofibers, HA particles: mostly round in shape mean length: 170 nm, mean width: 130 nm film formation (FIG. 7E and FIG. 7F) |

The composition of the surface of the coupon of each of CE3 and examples E14 to E16 was analyzed by EDS at 2000×. As shown in Table 2, the ratio of calcium to phosphorus (Ca/P) was measured as 1.04-1.14 for CE3 after a PEO treatment at 500 Hz or 650 Hz with no alkaline treatment. The Ca/P ratio increased significantly in each of examples E14-E16, which were subjected to the PEO treatment and then a 12 or 24-hour alkaline treatment. A wide range of Ca/P ratios was recorded in E14 (500 Hz)—revealing non-uniform crystallinity over the microstructure. By contrast, a narrow Ca/P ratio range of 1.53-1.55 was recorded for example E15 (650 Hz) after a 12-hour alkaline treatment—indicating uniformity in the composition of the treated ABS CpTi coupon. After extending the alkaline treatment from 12 to 24 hours, the range of Ca/P ratio increased to 1.62-1.74 in E17. In each of E14 to E16, a nanofibrous network overlaid with HA particles was observed. In Example E14, the alkaline treatment following structural distribution of HA particles. The development of a bioactive surface comprising a nanofibrous network, composite nanofibrous network overlaid with HA particles, and a HA film over the composite nanofibrous network and HA particles occurred after soaking the PEO treated ABS CpTi in hot NaOH solution. EDS analysis revealed about 2-4 at. % sodium (Na) on the surface of ABS CpTi coupons after the PEO and NaOH treatments, which is believed to be due to sodium titanate.

Example 1.3. ABS CpTi coupons were subjected to the same processes used in Example 1.2, except the PEO treatment was performed at 320V and 650 Hz for each of CE4 and E17 to E19, and the alkaline treatments for E17, E18, and E19 lasted 1 hour, while the concentration of the sodium hydroxide (NaOH) was varied. The conditions and results are shown in Table 3, with reference to the relevant figures.

TABLE 3

| | Experiments and results for the alkaline treatment step 135. | |
|---|---|---|
| No. | Alkaline Treatment Conditions | Results |
| CE4 | No alkaline treatment | Ca/P = 1.22, Na 0.9 at. % |
| E17 | 0.1M NaOH solution, 1 hour | Ca/P = 1.14, Na 1.1 at. % (FIG. 8A)<br>Nanofibers: 10-30 nm thick<br>Particles: mostly plate shaped<br>mean length: 130 nm<br>mean width: 84 nm |
| E18 | 0.5M NaOH solution, 1 hour | Ca/P = 1.10, Na 2.37 at. % (FIG. 8B)<br>Nanofibers: 20-30 nm thick<br>Particles: mostly plate-like and round<br>mean length: 230 nm<br>mean width: 120 nm |
| E19 | 5.0M NaOH solution, 1 hour | Ca/P = 2.21, Na 4.00 at. % (FIG. 8C)<br>Nanofibers: 40-70 nm thick<br>Particles: round, mean diameter: 265 nm<br>Films formed about 100-200 nm thick |

Figure 8C:
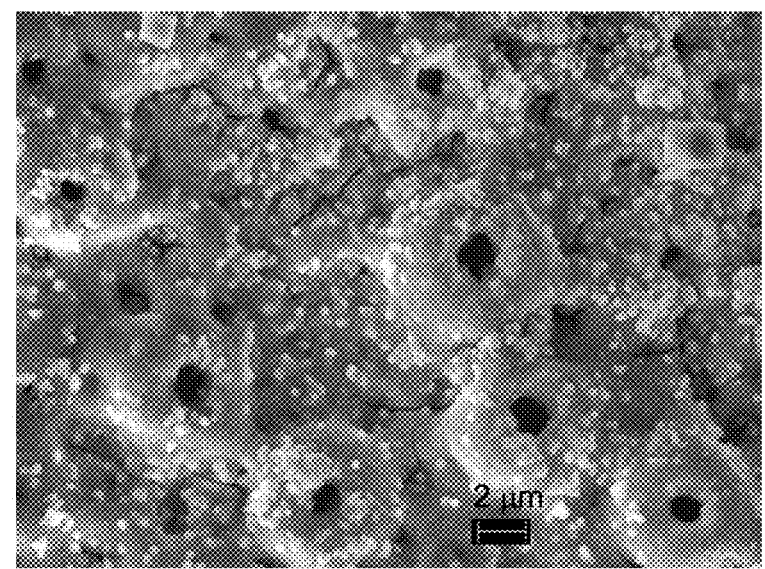
Figure 8D:
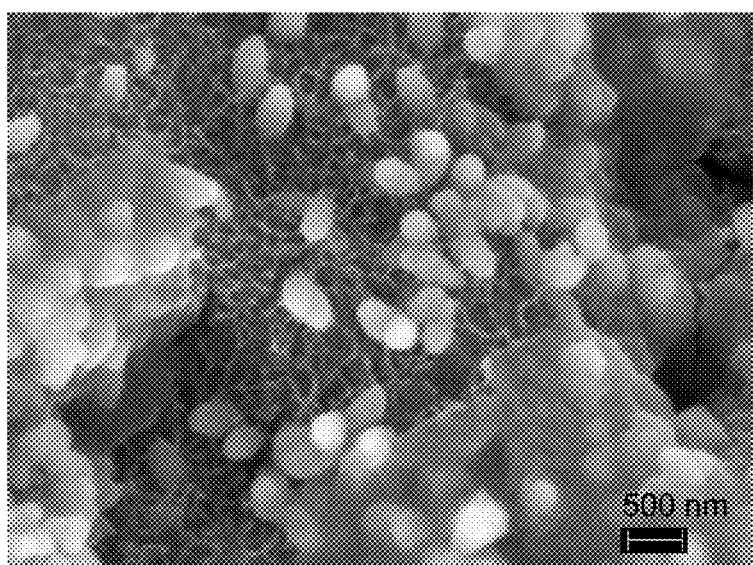

As shown in Table 3, with the selected PEO treatment conditions, the ratio of calcium to phosphorus did not change much when the concentration of sodium hydroxide was increased from 0.1M NaOH for entry E18 (1.14) to 0.5M NaOH for entry E19 (1.10)—indicating poor crystallinity of the treated ABS CpTi. But an increase in the concentration to 5.0M NaOH for entry E20 demonstrated a significant increase in the ratio of calcium to phosphorus (2.21). High magnification (50,000×) SEM images of the surfaces revealed a change in the surface of the microporous oxide layer from a clean microporous layer in FIG. 6B to crystalline structures of nanofibrous network and plate shaped calcium phosphate particles on the microporous oxide layer after NaOH treatments in examples E17 (FIG. 8A), E18 (FIG. 8B) and E19 (FIG. 8C). After alkaline treatment at low concentration (0.1M for E17), thin nanofibers and plate shaped particles were formed with an increase in size when the alkaline concentration was increased to 0.5M in E18. After the alkaline treatment in 5M concentration for 1 hour, the microstructural features in FIG. 8C at 10,000× and FIG. 8D at 50,000× show several deposits of round particles having a mean diameter of 265 nm on the surfaces of both the nanofibrous network and the films. Several cracks were observed within the films revealing poor hardness of the surface of the treated coupon. Cracks are not desirable for commercial applications. Overall, films formed along with thicker nanofibers (in the range of about 40-70 nm) and a higher amount of Na detected in E19 compared to E17 and E18 indicate aggressive reaction rates of local corrosive attacks by concentrated NaOH solution as per equations 1-3, resulting in the formation of structures comprising thicker nanofibrous networks and extensive deposits of particles after 5M alkaline treatment for 1 hour. Thus, poor mechanical reliability or a higher Ca/P ratio of 2.2 are not favorable for maintaining bone growth despite the formation of a nanofibrous network and HA particles. Overall, the alkaline treatment of the surfaces comprising a titanium dioxide layer having bioactive elements or phases changes the composition and microstructures of the surfaces, as provided by examples E14 to E19.

As shown in Tables 2 and 3, the elemental composition and microstructures of the surface of oxidized coupons are influenced by the concentration of the alkaline solution (NaOH) and the treatment time. After extensive testing, the conditions for the PEO treatment and subsequent NaOH treatment were modified to result in a calcium to phosphorus ratio of 1.68 to 1.72, which is nearly identical to the calcium to phosphorus ratio in hydroxyapatite in human bone (1.67) (Table 2).

Example 1.5. Porous coated ABS CpTi coupons subjected to certain treatment conditions described herein were tested to determine the respective ability of their surfaces to facilitate and encourage cell growth. Each specimen was tested in triplicate for its osteogenic and proliferation ability using human mesenchymal stem cells (hMSCs) seeded at a density of $2 \times 10^4$ cells/cm$^2$ in complete media (containing alpha minimum essential medium (MEM), 10% fetal bovine serum, and 1% antibiotic) and cultured for 10 days inside an incubator at 37° C. and 5% $CO_2$. Osteoblast differentiation media was added after 3 days of culturing in the complete media to evaluate the osteogenic differentiation ability of hMSCs on the treated and untreated specimens. Alkaline phosphatase activity (ALP) was evaluated quantitatively after 7 days of culturing in differentiating media using a commercially available buffer media and para-nitrophenyl phosphate (pNPP). The reaction was stopped by adding NaOH and the absorbance was read at 405 nm using a spectrophotometer every minute for 15 minutes. Cell quantification was performed after 10 days of culturing by cell counting reagent (CyQUANT, Thermofisher Scientific, USA). The comparative data obtained for the treated and untreated devices is provided in the bar diagrams shown in FIG. 9A (Alkaline Phosphatase activity per unit time) and FIG. 9B (cell growth after 10 days of incubation). Mean values of absorbance for each specimen are included in the diagrams.

Specimen 1 is an untreated porous coated ABS CpTi coupon utilized as a control or reference (labeled "untreated"). The reference coupon demonstrated an ALP activity (405 nm) of less than 0.01 and less than 40,000 cells are attached on the surface.

Specimen 2 is a porous coated ABS CpTi coupon that was subjected to step 115 (acid activation) and step 125 (PEO treatment, Voltage of 320V, Frequency of 650 Hz, Duty cycle of 20%, time of 10 minutes). Specimen 2 demonstrated an ALP activity (405 nm) of less than 0.01. Cell growth on the surface of Specimen 2 was about 100,000.

Specimen 3 is a porous coated ABS CpTi coupon that was subjected to same steps 115 and 125 used on Specimen 2 and further subjected to step 135 (0.5M NaOH, temperature of 60° C., time of 1 hour). Specimen 3 demonstrated an ALP activity (405 nm) with a mean value of 0.025. Cell growth tests on Specimen 3 resulted in about 250,000 cells (over 6-fold improvement) attached on the surface.

Specimen 4 is a porous coated ABS CpTi coupon that was subjected to same steps 115 and 125 used for Specimens 2 and 3 and further subjected to step 135 (0.5M NaOH, temperature of 60° C., time of 12 hours). Specimen 4 demonstrated an ALP activity (405 nm) with a mean value of 0.045, which is a 24-fold improvement over untreated Specimen 1. Cell growth tests on Specimen 4 resulted in about 250,000 cells attached on the surface, which is over an 8-fold improvement compared to the untreated Specimen 1.

Figure 9A:
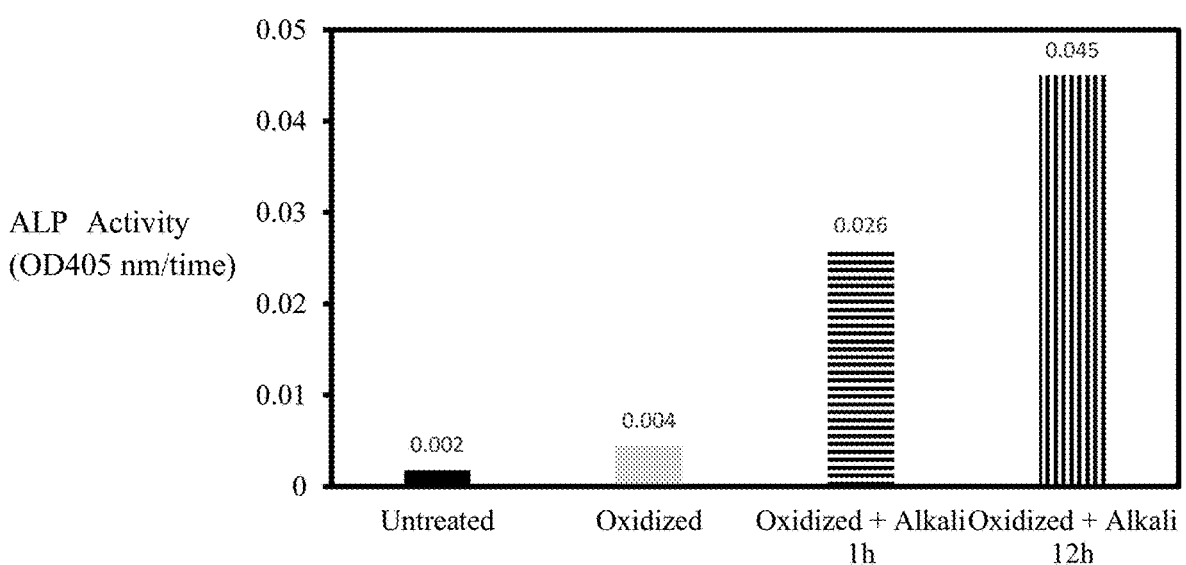
FIG. 9A and FIG. 9B are bar diagrams showing the alkaline phosphatase (ALP) activity and bone cell growth results, respectively, for a surface of the porous coated medical device in Example 1.4 processed according to one or more steps of the method of FIG. 1, in accordance with embodiments described herein.
Figure 9B:
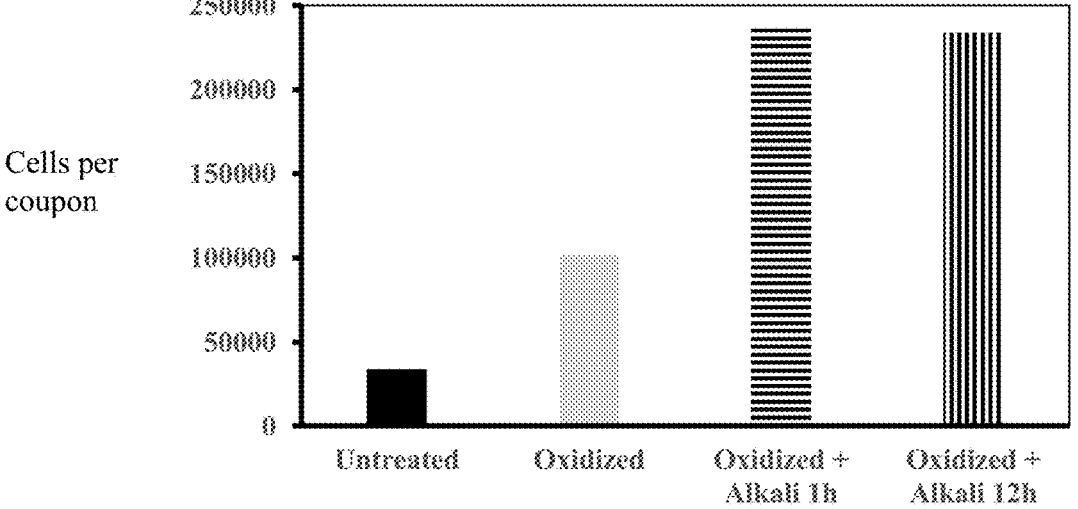

Referring to FIG. 9A, ALP activity is a measure of alkaline phosphatase (ALP), an indicator of early-stage differentiation of mesenchymal stem cells to osteoblasts. Alkaline phosphatase is produced by osteoblasts during the early stages of bone formation. Elevated alkaline phosphatase activity is often associated with bone formation and mineralization, which is indicative of an effective healing process around the implant. Specimens 3 and 4, which were subjected to a PEO treatment and an alkaline treatment, demonstrated significant improvement in ALP activity compared to untreated Specimen 1 and Specimen 2, which was subjected to the PEO treatment only. Referring to FIG. 9B, Specimens 3 and 4, which were subjected to a PEO treatment and an alkaline treatment also demonstrated an improved ability to facilitate cell growth compared to Specimens 1 and 2. These results demonstrate (i) the improved osteogenic properties for the medical devices treated according to step 115 (acid activation) and step 125 (PEO treatment); and (ii) an improvement of about 2400% for the osteogenic properties for the medical devices treated according to step 115 (acid activation), step 125 (PEO treatment), and step 135 (alkaline activation) relative to the untreated commercial specimen.

Figures 7C, 7D, 7E:
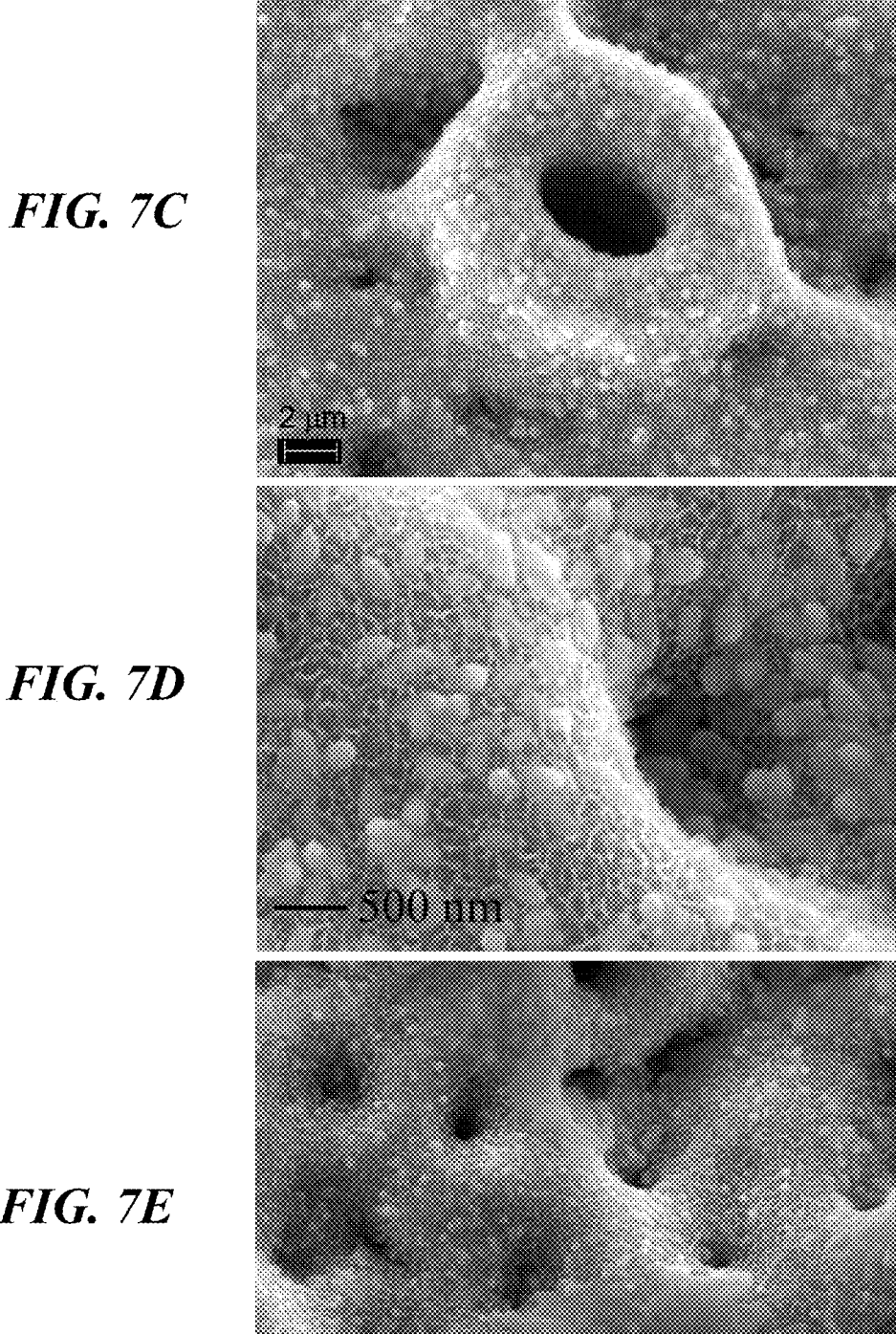
Figures 7F, 8A, 8B:
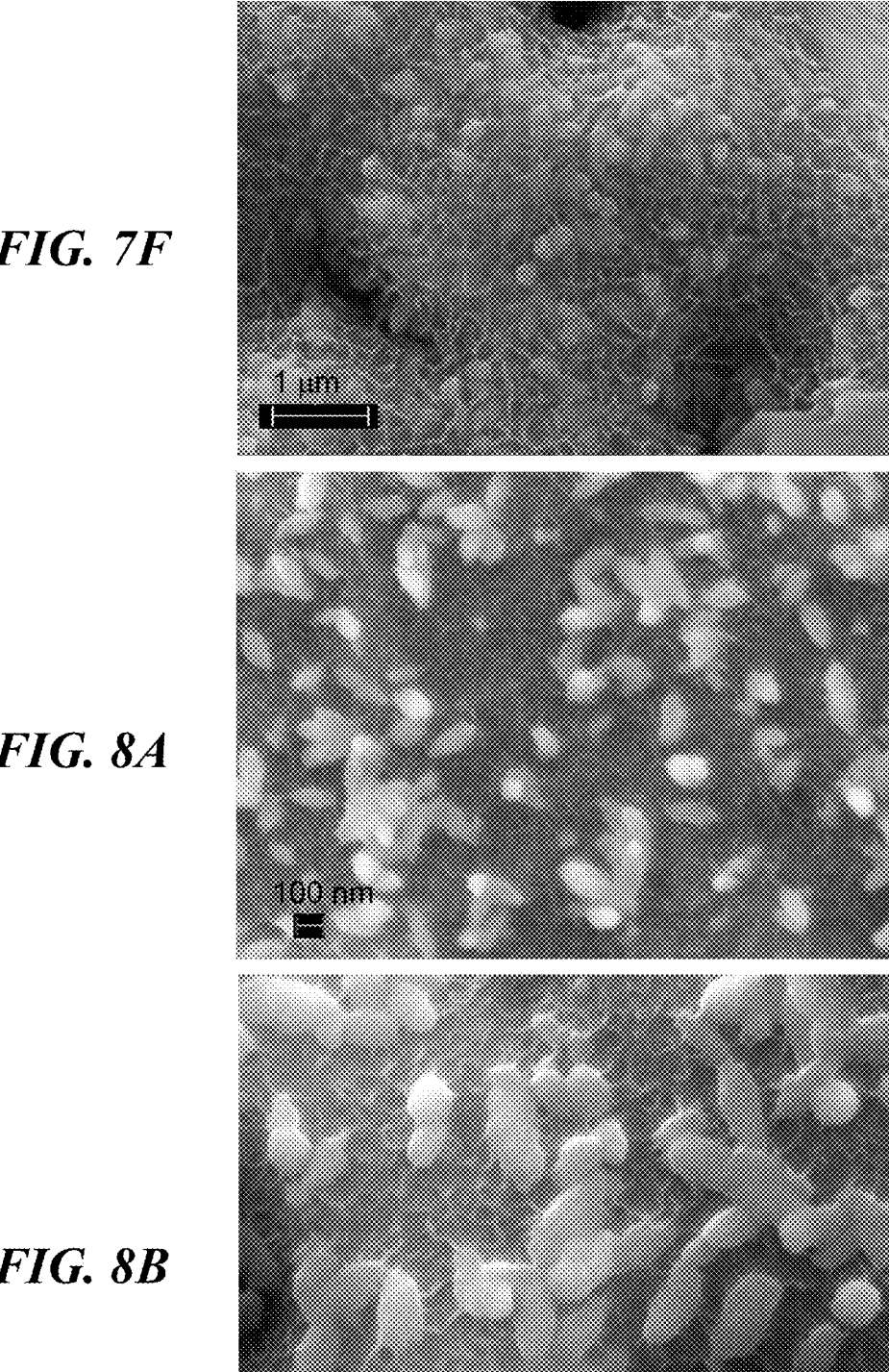
FIG. 8A, FIG. 8B, FIG. 8C, and FIG. 8D are SEM images of the activated surface of the porous coated medical device in Example 1.3 processed according to one or more steps of the method of FIG. 1, in accordance with embodiments described herein.

Example 1.6. The steps 105-145 of the method 100 were carried out in sequence to validate the key steps of the process. In the experiment, a porous coated ABS CpTi coupon was degreased for 30 minutes using a three-step wash, according to step 110. Next, the coupon was activated with an acid solution of 6.0M $HNO_3$ and 0.75M HF (8:1) at 40° C. for 20 minutes, according to step 115. The activated coupon was then washed in an ultrasonic device for 15 minutes to remove any residual acid according to step 120. Next, the activated coupon was subjected to PEO treatment for 10 minutes, according to step 125. The treated coupon was washed in an ultrasonic device for 15 minutes to remove any physically adsorbed salt from electrolytic solution after PEO treatment, according to step 130. Next, the treated coupon was activated using an alkaline solution, according to step 135. Finally, the activated coupon was washed. At the end of these steps, SEM images of the surface of the PEO treated ABS CpTi porous coated coupon were obtained. As shown in FIGS. 7C and 7D, the method provided a uniform bioactive modification to the surface of the porous coated ABS CpTi coupon due to presence of bioactive elements and crystalline apatite, including, e.g., calcium and phosphorous incorporated in the oxide layer, and a bioactive surface comprising a nanofibrous network overlaid with hydroxyapatite particles that are structurally similar to human bone. The micropores obtained in the microporous oxide layer were generally uniform in morphology and distribution with sizes in the range of 0.1-5 μm that can serve as anchoring sites for cellular adhesion and/or proliferation. FIGS. 7 and 8 demonstrate that nanofibers and hydroxyapatite particles grow inside the micropores, which can retain bioactive ions and compounds that can be released over time to facilitate bone in-growth and on-growth on a medical device that is implanted into a patient's body.

Example 2.1. Dense Ti-6Al-4V flat coupons (without a porous coating) from an implant manufacturer were used as test specimens to determine conditions for improving the bioactivity of the surfaces. The coupons were discs with a diameter of 25.4 mm and a height of 6.35 mm. The bioactivity can be improved by forming an oxide layer having calcium and phosphate in a Ca/P ratio of about 1.67 and/or by forming nanofibrous titanate or nanofibrous titanate-hydroxyapatite microstructures on the surface of the oxide layer to mimic the Ca/P ratio in human bone.

Solid implants without a porous metal surface or coatings have lower surface areas and generally require a lower input power during a PEO treatment to obtain an oxide layer or oxide layer having bioactive elements or antibacterial elements. A PEO treatment was performed on a series of dense coupons with a voltage of 200 volts, pulse frequency of 650 Hz, duty cycle of 10%, and treatment time of 8 minutes. Different electrolyte solutions were tested to evaluate the role of electrolyte concentration in improving the bioactivity (i.e., Ca/P close to 1.67) of the surface. The first electrolyte solution comprised 0.06M CaAc, 0.06M Na-EDTA, 0.03M NaP, and 0.2 KOH. The second electrolyte solution comprised 0.13M CaAc, 0.13M Na-EDTA, 0.13M NaP, and 0.35 KOH. The subsequent alkaline treatment was performed in a 0.5M NaOH solution at 60° C. for 1 hour, 12 hours or 24 hours. The elemental composition of the treated surfaces was measured by Energy Dispersive Spectroscopy (EDS) at 5 random locations on the surface and the average atomic percentage (at.%) of the elements Ti, O, Ca, P and Na was determined. The average values of elemental concentration for Ca, P and Na are shown in Table 4.

TABLE 4

Examples for the PEO step 125 and post-PEO treatments applied to a dense Ti-6Al-4V alloy disc substrate.

| No. | PEO treatment | Heat Treated 600° C., 1 h | NaOH Treatment | | | Elemental composition | | | |
|-----|---------------|-----------|------|------|------|------|------|------|------|
| | | | Conc (M) | Temp (° C.) | Time (hours) | Ca at. % | P at. % | Na at. % | Ca/P |
| CE5 | (0.06M CaAc, 0.06M Na-EDTA, | Not treated | Not treated | | | 4.57 | 6.17 | 0.53 | 0.74 |
| CE6 | 0.03M NaP, 0.2M | Treated | Not treated | | | 4.36 | 6.10 | 0.30 | 0.72 |
| CE7 | KOH); | Treated | 0.5 | 60 | 1 | 3.86 | 4.57 | 0.53 | 0.84 |
| E20 | $V_m$ 200 V; f 650 Hz; | Not treated | 0.5 | 60 | 12 | 1.83 | 3.27 | 0.3 | 0.56 |

TABLE 4-continued

Examples for the PEO step 125 and post-PEO treatments
applied to a dense Ti-6Al-4V alloy disc substrate.

| E21 | Duty 10%;<br>Time 8 min. | Not<br>treated | 0.5 | 60 | 24 | 3.83 | 2.80 | 1.43 | 1.36 |
|---|---|---|---|---|---|---|---|---|---|

| | | NaOH treatment | | | Elemental composition | | | |
|---|---|---|---|---|---|---|---|---|
| | PEO treatment | Conc.<br>(M) | Temp.<br>(° C.) | Time<br>(hours) | Ca<br>at. % | P<br>at. % | Na<br>at. % | Ca/P |
| E22 | (0.13M CaAc, | Not treated | | | 6.6 | 6.3 | 0.8 | 1.05 |
| E23 | 0.13M Na-EDTA, | 0.5 | 60 | 12 | 5.5 | 3.6 | 0.85 | 1.53 |
| E24 | 0.06M NaP);<br>$V_m$ 200 V;<br>f 650 Hz;<br>Duty 10%;<br>Time 8 min. | 0.5 | 60 | 24 | 5.1 | 3.0 | 1.6 | 1.7 |

M = molarity; $V_m$ = mean voltage; f = pulse frequency; Duty = duty cycle.

Figure 10A:
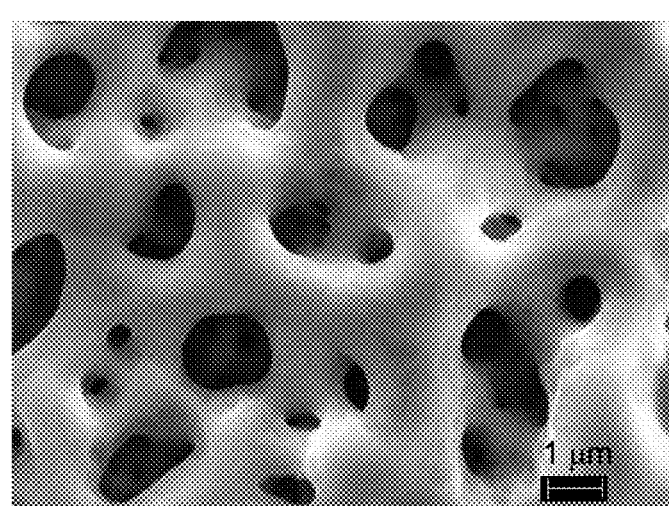
FIG. 10A, FIG. 10B, FIG. 10C, FIG. 10D, and FIG. 10E are SEM images of the surfaces of a dense medical device in Example 2.1 processed according to one or more steps of the method of FIG. 1, in accordance with embodiments described herein.
Figure 10B:
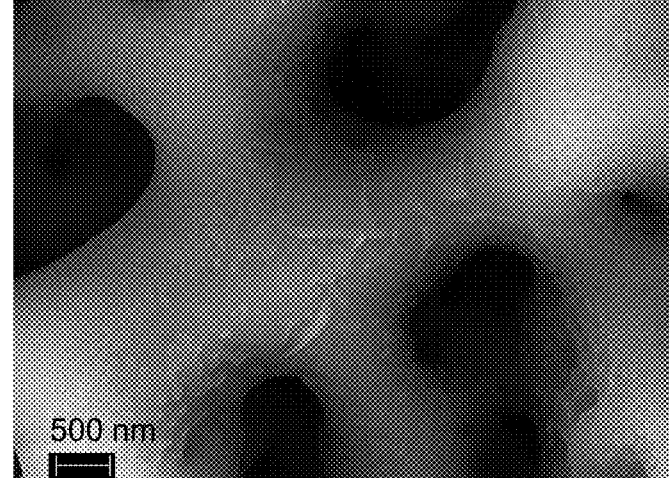
Figure 10C:
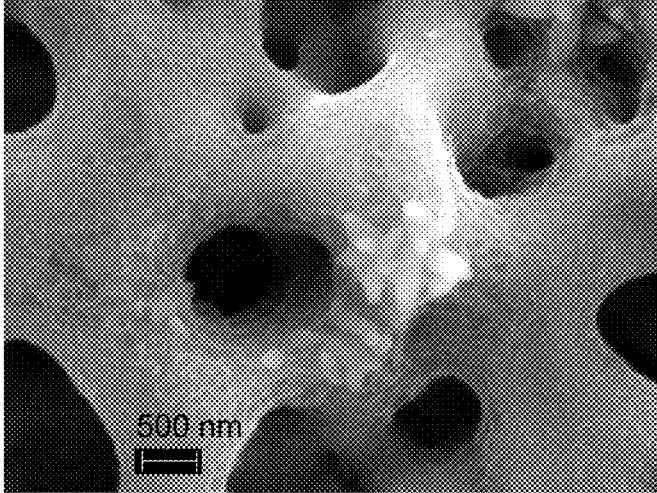

During the PEO treatment, the electric current across the substrate was recorded at the initial time (t=0 minutes) and the end time (t=8 minutes). For each PEO treatment, a current of 0.1A was measured at the end time. The thickness of the oxide layer ranged from 1.3 to 2.8 μm. In CE5, the PEO treatment resulted in a microporous oxide layer having bioactive elements with a Ca/P ratio of 0.74, a mean pore size of about 0.5 μm, and a surface porosity of about 24% as observed with unexpectly high Vickers hardness of about 1100 HV. An SEM image (25000× magnification) of the coupon after the PEO treatment shown in FIG. 10A revealed the absence of any micro-cracks that are often present in existing PEO treatments. In CE6, the PEO treatment was followed by a heat treatment at 600° C. for 1 hour in air atmosphere. The heat treatment of CE5 resulted in a diffusion of incorporated calcium phosphate from within the microporous Ti-oxide layer to the surface as shown by nanocrystalline round particles without much change in the Ca/P ratio and demonstrated a higher Vicker hardness of about 1300 HV. An SEM image (50,000×) of the coupon after the PEO treatment and heat treatment is shown in FIG. 10B. In example CE7, a sequential PEO treatment, heat treatment, and an alkaline treatment in 0.5M NaOH solution at 60° C. for 1 hour were performed to obtain a microporous Ti-oxide layer overlayed with nanofibers and discrete crystals of calcium phosphate. The treated surface revealed some improvement in the Ca/P ratio from 0.72 in CE6 to 0.84 in CE7, a mean pore size of about 0.8 μm, layer thickness of about 2.5-3 μm, and surface porosity of about 21%. An SEM image (50000× magnification) of the coupon of the treated surface in example CE7 is shown in FIG. 10C. In CE7, the amount of Ca and P on the surface of treated Ti alloy device slightly decreased after the NaOH treatment of CE6 (Table 4) indicating ionic dissolution.

Figure 10D:
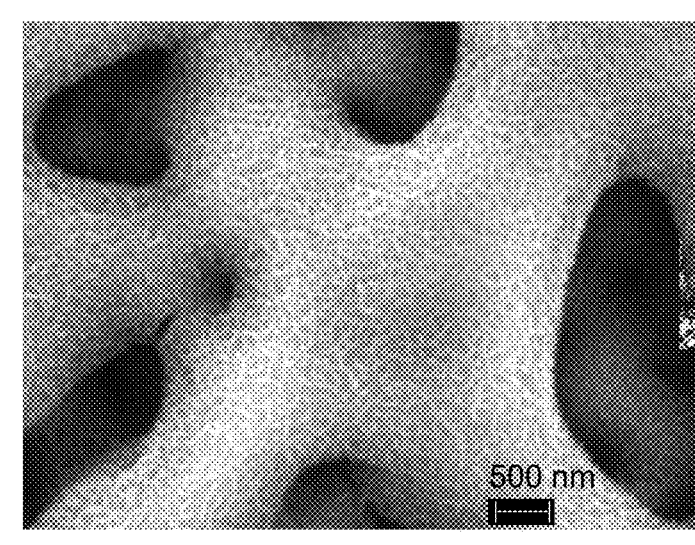

In E20 and E21, the PEO treatments were followed by alkaline treatments in a 0.5M NaOH solution at 60° C. for 12 and 24 hours, respectively. FIG. 10D is an SEM image (50000×) of a microporous Ti-oxide layer overlaid with a microstructure comprising a network of nanofibers having a thickness of about 20 nm, which was formed after the PEO treatment and a subsequent treatment with 0.5M NaOH solution at 60° C. for 12 hours (E20).

Per equation 1, $TiO_2$ is attacked by $OH^-$ ions in the NaOH solution to form hydrogen titanate ($HTiO_3$)$^-$ and resulted in an increase in mean pore size to 0.9 μm, surface porosity to 25%, and a significant dissolution of Ca and P ions as indicated by the decrease in the amounts of Ca and P from 4.57 at. % Ca and 6.17 at. % P, with Ca/P ratio of 0.74 in the Ti-oxide layer in CE5 to 1.83 at. % Ca and 3.27 at. % P with Ca/P ratio of 0.56 in 12 hours NaOH treated oxide layer in E20 indicating significant ionic dissolution (Table 4).

Figure 10E:
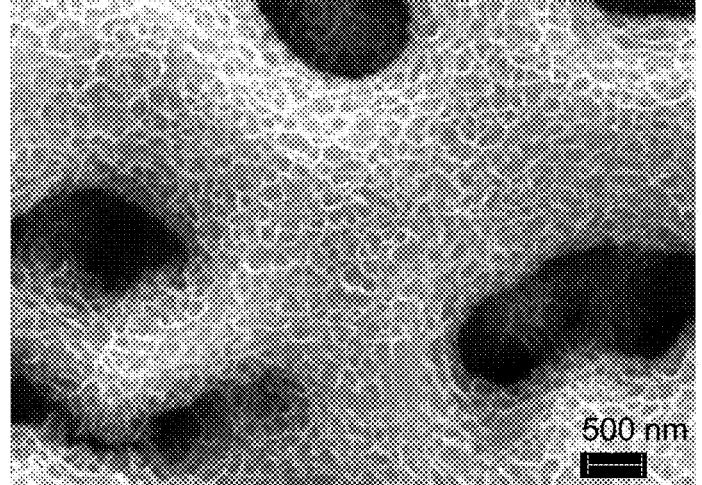

FIG. 10E (50000×) is an SEM image of a microporous Ti-oxide layer overlaid with a microstructure comprising a network of thicker nanofibers having a thickness of about 28 nm was formed after the PEO treatment and alkaline treatment with 0.5M NaOH solution for longer soaking time of 24 hours at 60° C. in example, E21. Elemental analysis by EDS revealed an increased elemental concentration of 3.83 at. % Ca and 2.80 at. % P, with an improved Ca/P ratio of 1.36 (Table 5). The signifcant increase in sodium content from 0.53 at. % in CE5 (PEO treated Ti) to about 1.43 at. % after a 24-hour NaOH treatment of a PEO treated Ti indicates the formation of a crystalline phase, which is likely sodium titanate or calcium titanate according to the theoretical equation 2 (the reaction of $TiO_2$ and NaOH to form sodium titanate or sodium hydrogen titanate) or equation 3.

In examples E22 to E24, the PEO treatment of the dense Ti alloy coupon was performed under the same conditions in Table 4 except using an electrolyte comprising a higher concentration of salts (i.e., 0.13M CaAc, 0.13M Na-EDTA, 0.06M NaP, and 0.35M KOH). Increasing the electrolyte conconcentration enriched the surface of oxide layer with a higher amount of bioactive elements and an improved Ca/P ratio of 1.08 in example E22. In example E23, the PEO treatment was performed under the same conditions used for E22 except a subsequent alkaline treatment for 12 hours, resulting in a microporous oxide layer overlaid with a composite bioactive surface comprising nanofibrous network and nano-to-micro sized plate shaped crystals of calcium phosphate having a surface elemental composition of 5.5 at. % Ca, 3.6 at. % P, and a Ca/P ratio of 1.53. X-ray diffraction analysis revealed the observed nano-micro plates of calcium phosphate are comprised of hydroxyapatite and a nanofibrous network of sodium titanate or sodium hydrogen titanate. The hydroxyapatite plates appear to be nucleated on the nanofibers, and revealed an improved crystallinity demonstrated by an improved Ca/P ratio of 1.53. In example E24, extending alkaline treatment time to 24 hours further improved crystallinity of surface of treated Ti alloy with an improved Ca/P ratio of 1.7. These results demonstrate the benefits of NaOH treatment for forming a bioactive surface comprising nanofibrous network or a composite of nanofibrous networks and hydroxyapatite crystals that are useful for enhancing bone regeneration around a medical device treated with the PEO step 125 and NaOH treatment 135.

Figure 16A:
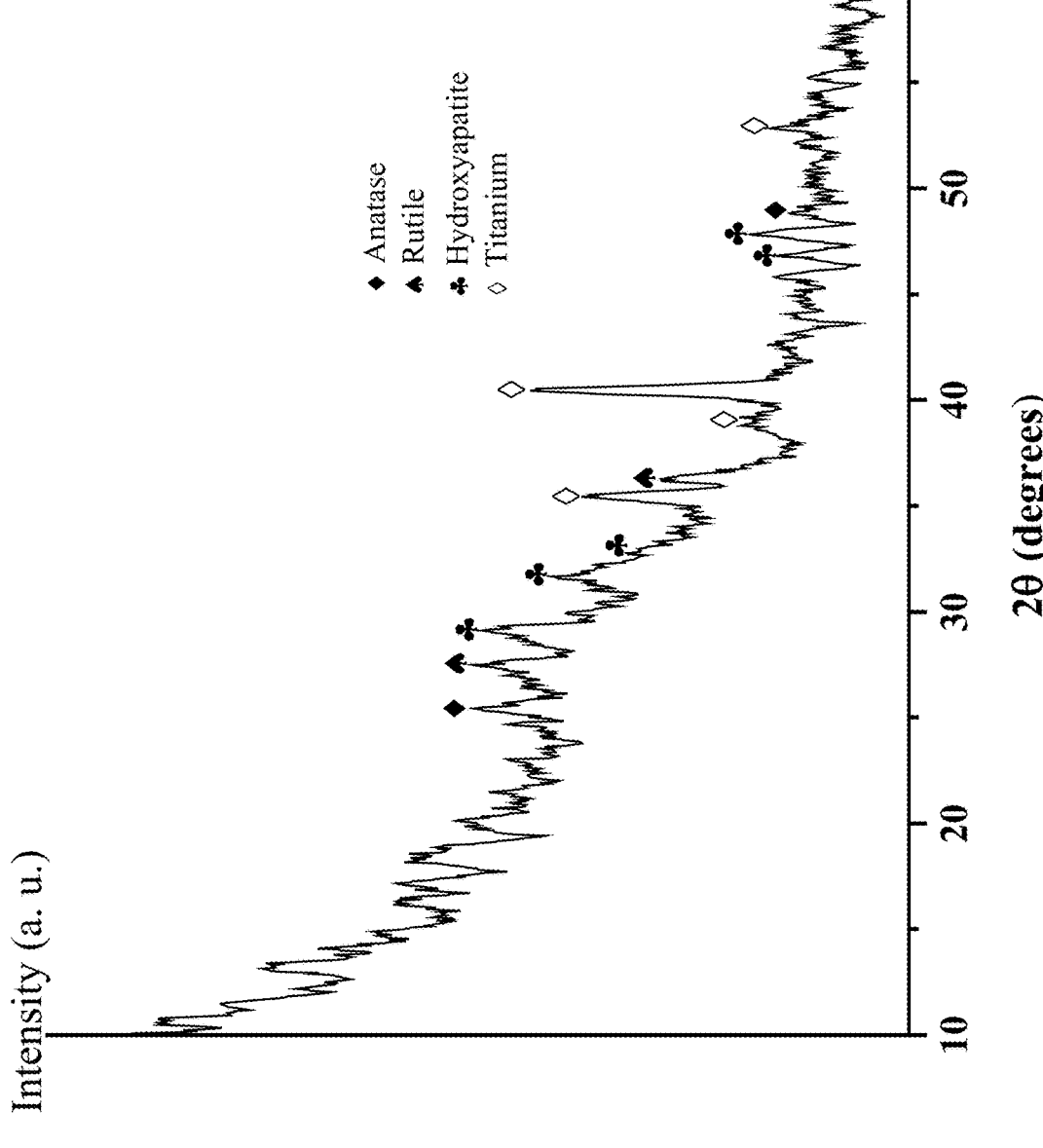
FIG. 16A and FIG. 16B are X-ray Diffraction patterns of the surface of a dense medical device after PEO treatment and after PEO treatment and alkaline treatment, respectively, in accordance with embodiments described herein.
Figure 16B:
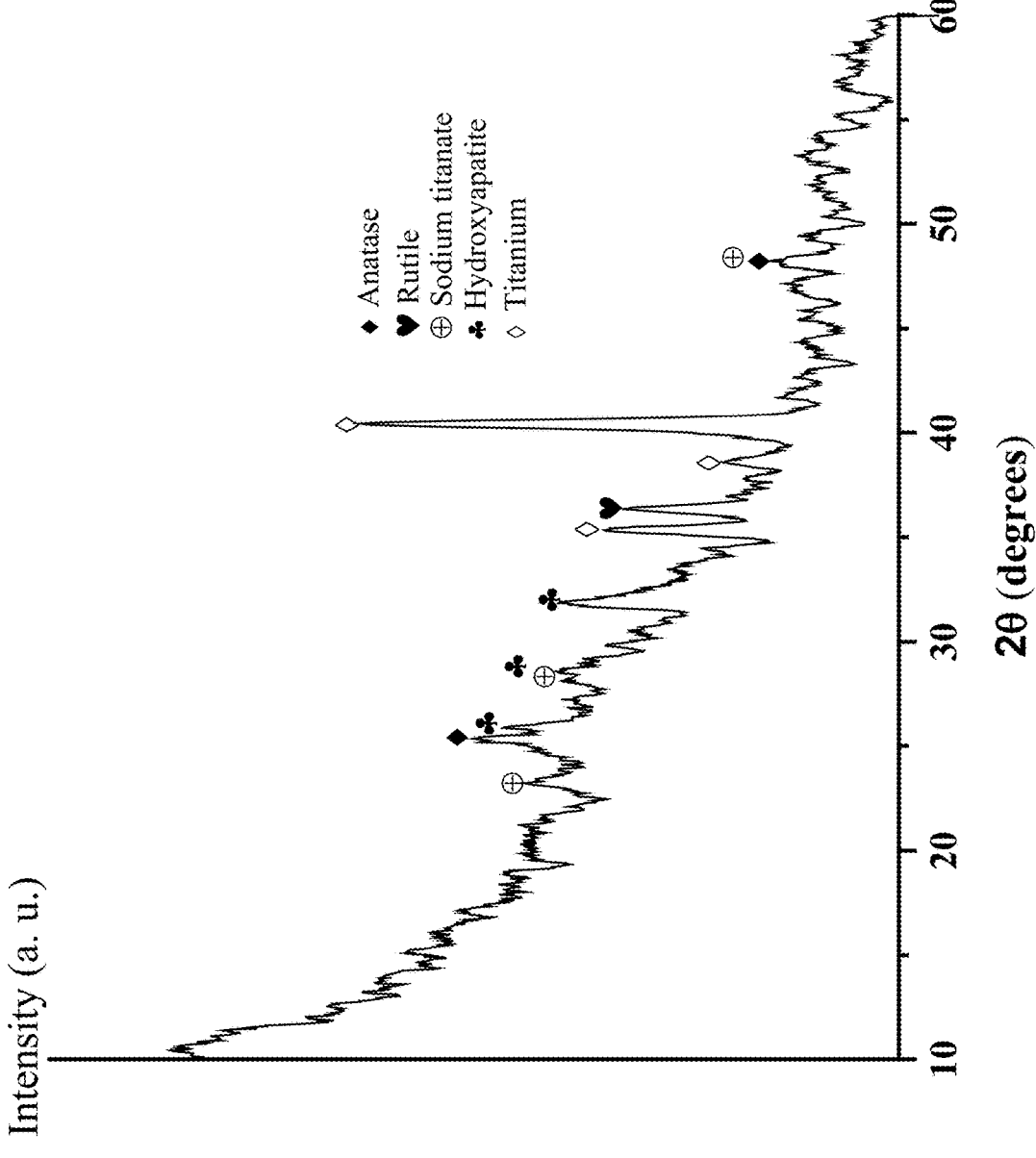

X-ray diffraction (XRD) was performed on a PEO treated Ti alloy coupon and on a Ti alloy coupon treated with both PEO and a NaOH solution. The XRD was performed in thin film mode using a Panalytical Empyrean diffractometer operated at 45 kV and 40 mA. The XRD pattern for the coupon treated with PEO revealed the major intensity peaks for anatase, rutile, hydroxyapatite, and titanium, as shown in FIG. 16A. The XRD pattern for the coupon treated with both PEO and NaOH revealed the major intensity peaks of anatase, rutile, hydroxyapatite, titanium, and additional peaks of sodium titanate as shown in FIG. 16B. The XRD data for both the PEO treated and the PEO/NaOH treated dense Ti alloy coupons show hydroxyapatite. But in PEO treated, the hydroxyapatite seems to be incorporated in the oxide layer and cannot be seen clearly using SEM. After the NaOH treatment of the oxidized Ti alloy for 12 hours or more, the nanofibrous network and hydroxyapatite plates can be observed using SEM, indicating the NaOH treatment causes the hydroxyapatite to diffuse to the surface and crystallize. Based on the SEM microstrutures of the nanofibrous network, the compositional data by EDS, and the XRD data, the nanofibrous network structure was found to be composed of a composite of calcium and sodium titanate. Both titanates can co-exist via an ionic exchange of sodium by calcium, or vice versa, per equations 2 and 3. An improved Ca/P ratio, and the presence of the bioactive phases of hydroxyapatite, calcium titanate, and sodium titanate are expected to enhance the bioactivity of the titanium metal or titanium alloy implant treated by the PEO step 125 and the NaOH step 135.

Figure 11A:
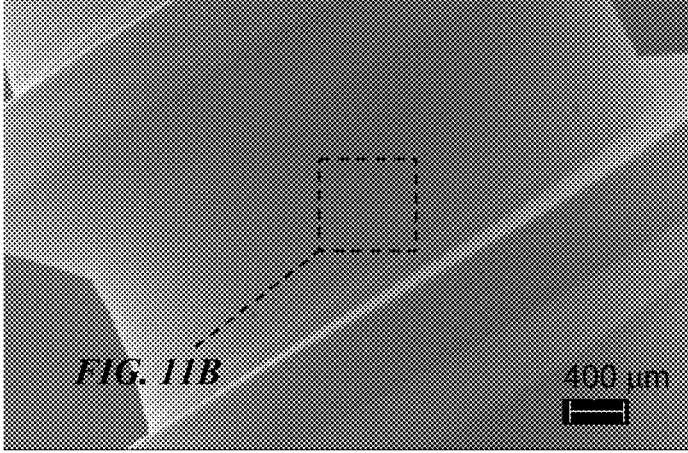
FIG. 11A, FIG. 11B, and FIG. 11C are SEM images of the surfaces of a dense pedicle screw medical device in Example 2.2 processed according to one or more steps of the method of FIG. 1, in accordance with embodiments described herein.
Figures 11B, 11C, 12A:
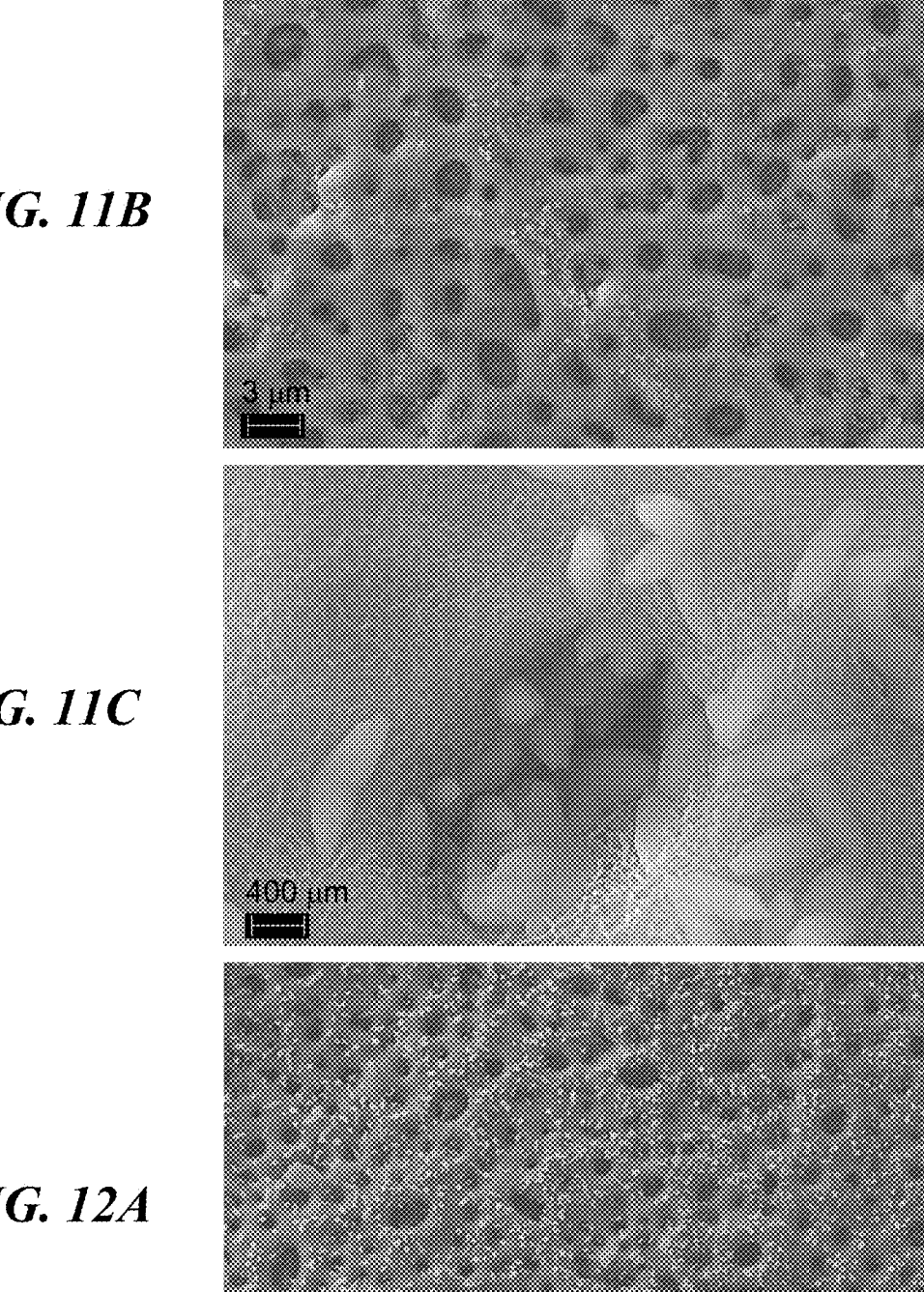
FIG. 12A, FIG. 12B, FIG. 12C, FIG. 12D, FIG. 12E, and FIG. 12F are SEM images of the surface of a porous 3D printed medical device processed according to one or more steps of the method of FIG. 1, in Example 3.1, in accordance with embodiments described herein.

Example 2.2. Dense Ti-6Al-4V pedicle screws (without a porous coating) from an implant manufacturer were used as test specimens to determine conditions for improving the bioactivity of the surfaces. The PEO treatment conditions included an electrolyte concentration of 0.13M CaAc, 0.13M Na-EDTA, 0.06M NaP, and 0.35M KOH maintained at a temperature of 16-20° C., a unipolar pulse mode with a voltage of 200 volts, a pulse frequency of 650 Hz, a duty cycle of 10%, a treatment time of 8 minutes. The alkaline treatment conditions included a NaOH solution comprising 0.5M NaOH for 12 hours, at 60° C. The SEM images for the resulting surface are shown in FIGS. 11A, 11B, and 11C. FIG. 11A shows an image of a pedicle screw at 25×. The boxed surface in FIG. 11A is magnified to 3000× magnification to reveal the surface of treated pedicle screw in FIG. 11B. FIG. 11C shows the image magnified at 25000×. FIG. 11B shows a microporous surface overlaid with crystalline particles formed spatially. The high-resolution SEM image in FIG. 11C shows the extensive deposits of hydroxyapatite plates inside a pore on the surface as well as outside the micropore. Under the PEO and NaOH treatment conditions utilized for the dense implants, hydroxyapatite plates were incorporated extensively on the surface and within the pores of the microporous surface layer, and a network of nanofibers was formed that uniformly covered the surface.

Implantable devices with a partially porous coated region having a relatively high surface area and a partially dense region (non-porous) having a relatively low surface area can be treated separately in the method 100. High currents are needed to generate a uniform oxide layer on the porous portion, but those currents can damage or cause surface melting to the non-porous portion. In such embodiments, the non-porous portions of the device can be masked from the treatments and treated separately with preferred conditions at lower voltages than used for porous coated portions.

Example 3.1. 3D printed Ti-6Al-4V alloy coupons manufactured by the selective laser melting method and obtained from an implant manufacturer were used as test specimens to determine conditions for improving the bioactivity of the surface. Specifically, 3D printed Ti-6Al-4V coupons having a diameter of about 25.4 mm, a thickness of about 6.35 mm, and a porous Ti-6Al-4V coating that is about 1 mm thick. The 3D printed coupons with a stochastic lattice structure were manufactured by selective laser melting method. The mean porosity of the 3D printed coating was about 60%, and the mean pore size was about 600 μm with pore sizes in the range of 300 to 900 μm.

FIG. 2C is an SEM image (25× magnification) showing the surface of a porous coated 3D printed coupon as received from a manufacturer. The porous surface contains partially sintered round particles, including residual powder from the manufacturing process, on the surface and around the edges of the pores. According to step 110 of the method 100, the 3D printed coupon was degreased with subsequent treatments of propanol and water using ultrasonication, for 1 hour each, at 40-60° C. Residual or loose powder entrapped inside the 3D printed coupon was removed from the coupon after ultrasonication. High magnification SEM images revealed additional, partially sintered particles within the porous lattice structure, and it was determined using EDS that there were high levels of oxygen (8-14%) on the surface of the device, indicating oxide scales remain present after the degreasing step.

The treatments and results for the 3D printed coupons are provided in Table 5. Examples CE8 and E25-E27 in Table 5 were subjected to a PEO treatment. The conditions for the PEO treatment comprise a voltage in the range of 200 to 320 volts and a treatment time of 10 minutes. The electrolyte composition was 0.06M CaAc, 0.06M 2Na-EDTA, 0.03M NaP, and 0.2M KOH. The pulse frequency was 650 Hz, and the duty cycle was 20%. The initial currents at the start of the PEO treatment were at 7A for CE8 and 5A for each E25-E27. For each example, the current gradually decreased to reach a final current of 0.6A after 5 minutes and remained at 0.6A at the end of the PEO treatment (t=10 minutes). The decrease in current is consistent with the formation of an oxide layer on the surface of the 3D printed coupons. The elemental composition of the surface was determined by EDS at five random locations and mean value of bioactive elements and range of Ca/P ratios were determined.

TABLE 5

| | Surface activation treatment 6M HNO$_3$, 0.75M HF, 40° C., 20 | PEO treatment f 650 Hz, Duty 20%, time 10 minutes Mean voltage, V$_m$, | NaOH treatment 0.5M, 60° C., | Ca | P | Na | |
|---|---|---|---|---|---|---|---|
| No. | minutes | (volts) | 12 h | at. % | at. % | at. % | Ca/P |
| CE8 | Not treated | Treated at 260 V | Treated | 6.6 | 4.3 | 3.0 | 1.5-1.6 |
| E25 | Treated | Treated at 260 V | Not treated | 7.2 | 6.4 | 0.5 | 1.08-1.15 |
| E26 | Treated | Treated at 320 V | Not treated | 8.2 | 7.0 | 0.7 | 1.10-1.17 |
| E27 | Treated | Treated at 260 V | Treated | 7.6 | 4.4 | 2.8 | 1.71-1.74 |

Experiments for the acid activation, PEO treatment, and alkaline treatment steps and results.

Elemental composition

M = molarity; V$_m$ = mean voltage; f = pulse frequency; Duty = duty cycle.

Figures 12B, 12C, 12D:
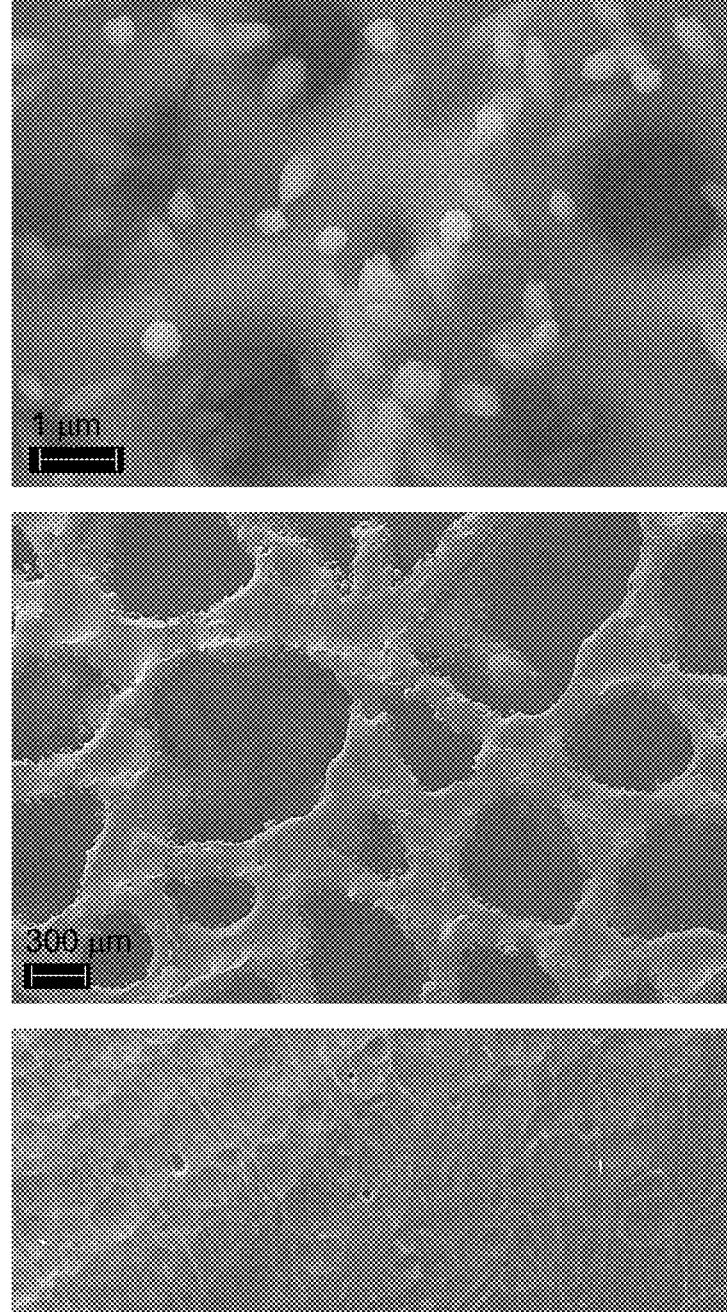

FIG. 12A and FIG. 12B are SEM images of the 3D printed coupon in CE8 after the degreasing step, PEO treatment, and an alkaline treatment—without a prior acid activation treatment. The SEM image in FIG. 12A (2000×) shows a wide spatial distribution of particles on the microporous surface of the oxide layer. FIG. 12B (10,000×) is a further magnification of the surface in FIG. 12A that shows plate shaped and round particles on the surface of a nanofibrous network formed on the surface of microporous oxide layer after alkaline treatment. The elemental composition was determined by EDS. The PEO and NaOH treated 3D printed devices revealed a Ca/P ratio between 1.5 to 1.6 and a sodium concentration of 3 at. %, as shown in Table 5.

Treatment of the 3D printed device with an acid solution was examined to determine if activation prior to the PEO treatment would improve the surface properties of the 3D printed device. The surface activation step 115 was carried out on the device. FIG. 12C is an SEM image (27×) showing the porous surface after the acid treatment step (and prior to further treatments), with the loosely bound particles around the edges of the pores removed from the surfaces. It was determined using EDS that all oxygen was removed from the surface of the 3D printed coupon by the acid treatment. Additionally, the acid activation treatment created a fine surface microstructure, as shown in FIG. 12D, which is high magnification of the surface in FIG. 12C. This kind of clean and activated surface can be beneficial for protein adsorption and cell growth.

Figure 12E:
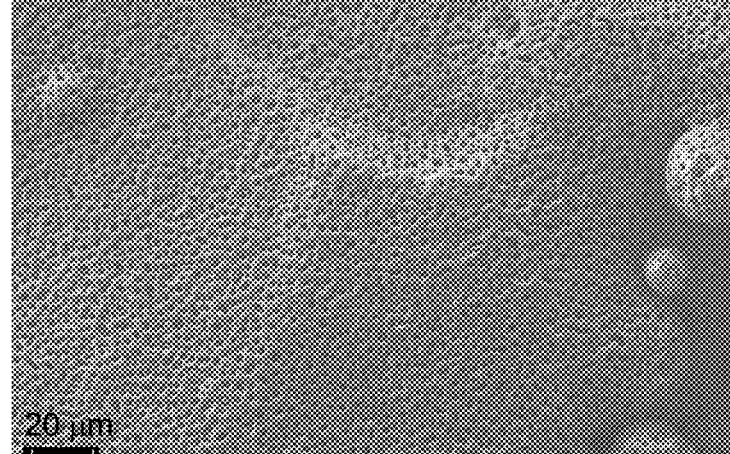

FIG. 12E is SEM image (500×) of the 3D printed coupon in E25 after the acid treatment and the PEO treatment. The surface in the image comprises uniformity in both the distribution and general size (diameter) of the micropores. Under these conditions, EDS revealed a Ca/P ratio between 1.10-1.14 and a sodium concentration of 0.5 at. %.

After the PEO treatment, the mean hardness of the surface of the coupons was measured for each of examples E25 (260V) and E26 (320V). As a reference, the 3D printed Ti-6Al-4V coupon as received from the manufacturer has a mean hardness of 380 HV. After the PEO treatments for E25 and E26, the treated coupons showed a 2- to 3-fold increase in mean hardness of 1070 HV in E25 (treated at 260V) and 620 HV in E26 (treated at 320V). The PEO treatment at 260 volts also resulted in minimal cracks in the oxide layer, compared to the PEO treatment at 320V, which resulted in several big cracks on the surface resulting in a lower mean hardness of 620 HV.

Alkaline treatment for the 3D printed coupons after the acid activation and PEO treatment was examined to see whether the combination of steps in method 100 improves the surface properties of the 3D printed device. Using SEM imaging, it was determined that the number of plate particles per unit area was almost three times for a PEO treatment using 650 Hz and NaOH solution treatment for 12 h than for a PEO treatment using 500 Hz and a NaOH solution treatment for 12 h. These results are consistent with the results for the treated ABS CpTi coupons. These results confirm that pulse frequency affects the microstructure of the PEO treated and subsequent NaOH treated Ti based devices.

Figure 12F:
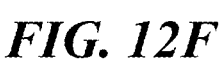
Figure 12F:
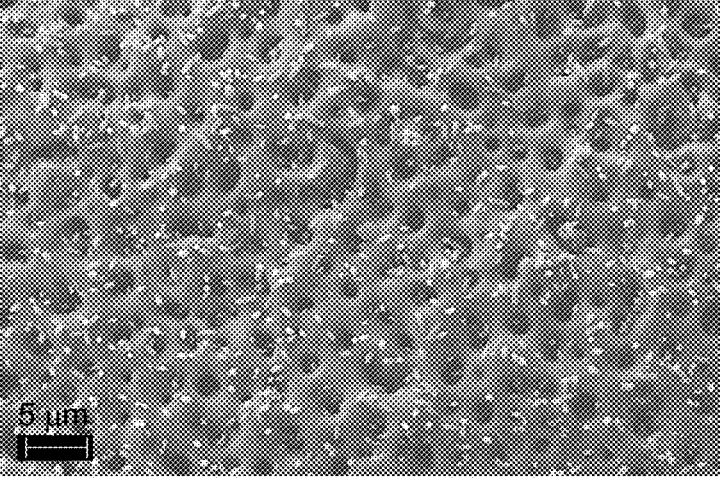

FIG. 12F is an SEM image of example E27, which was subjected to an acid activation step, PEO treatment at 650 Hz, and an alkaline treatment. By comparison, the process without the acid treatment resulted in more particles on the surface of the 3D printed device, as shown in FIG. 12A. However, despite producing less particles, the process that used the acid treatment resulted in more desirable surface composition, including Ca/P ratio in the range of 1.71-1.74, and higher content of Ca (at. %) of 7.1-8.2; and P (at. %) of 4.1-4.8 compared to Ca/P ratio in the range of 1.5-1.6, relatively lower content of Ca (at. %) of 6.3-6.9, and P (at. %) of 4.2-4.3. Increasing the electrolyte concentration to 0.13M CaAc, 0.13M Na-EDTA, 0.06M NaP, and 0.35M KOH for the PEO treatment, followed by 24 hours of alkaline treatment, was performed on 3D printed devices after the initial acid activation step to investigate the effect of higher electrolyte concentration and longer NaOH treatment. The results showed the number of plate particles increased per unit area and a Ca/P ratio of 2.05.

Figure 13A:
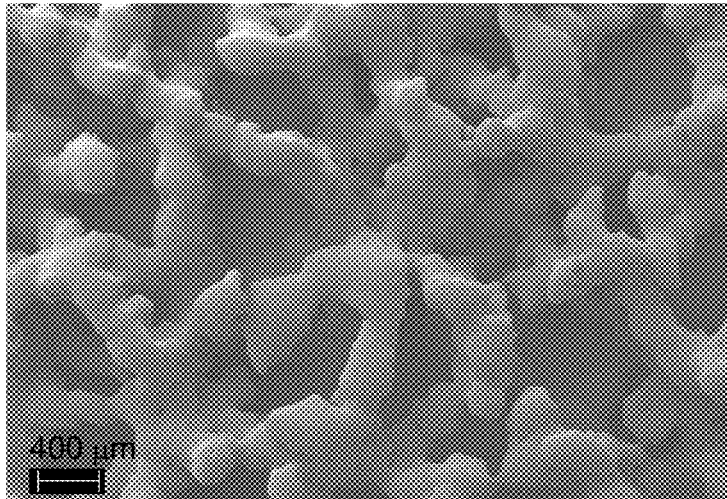
FIG. 13A and FIG. 13B are SEM images of the surface of a porous 3D printed medical device processed according to one or more steps of the method of FIG. 1, in Example 3.2, in accordance with embodiments described herein.
Figure 13B:
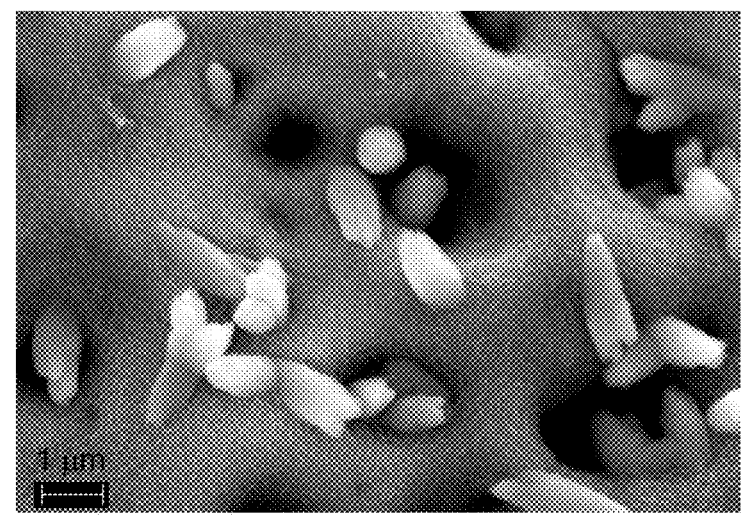

Example 3.2. 3D printed Ti-6Al-4V alloy coupons with 1 mm thick, porous coating was manufactured by the electron beam melting method and obtained from an implant manufacturer and were used as test specimens. The lattice structure of the coating is that of a trabecular structure applied on the surface of a Ti alloy medical device to mimic the structure of bone. The mean porosity of the 3D printed Ti alloy coating is about 60% and the mean pore size is about 500 μm. FIG. 2D is an SEM image of the surface of a 3D printed Ti-6Al-4V coupon as received from the manufacturer. In the image, the porous surface contains numerous partially melted round particles left behind from the manufacturing process. The as-received coupon was subjected to the steps of the method 100, including the degreasing step 110, the acid activation step 115, the PEO treatment step 125, and the alkaline activation step 135. The coupon was degreased with subsequent treatments of propanol and water using ultrasonication, for 1 hour each, at 40-60° C. The acid solution shown in Table 5 in Example 3.1 for the surface activation treatment was also used in this example. As shown in the SEM image in FIG. 13A (24×), the surface of the acid treated 3D printed coupon is clean and free of any of the particles remaining from the manufacturing process. The PEO treatment parameters included an electrolyte comprising 0.06M CaAc, 0.06M Na-EDTA, and 0.03M NaP, a voltage of 260V, a frequency of 650 Hz, a 20% duty cycle, and an end time of 10 minutes. For each example, the current gradually decreased to reach a final current of 0.6A after 3 minutes and remained at 0.6A at the end of the PEO treatment (t=10 minutes). The decrease in current is consistent with the formation of an oxide layer on the surface of the 3D printed coupons. After the PEO treatment, elemental composition data for the surface of the 3D printed coupon was obtained by energy dispersive spectroscopy (EDS). The elemental composition of the surface was determined at five random locations and mean value of bioactive elements and range of Ca/P ratios were determined. In example E28, the EDS data shows 5.9 at. % Ca, 5.7 at. % P and 0.4 at. % Na, in addition to C, Ti, O. The Ca/P ratios of the surface after the PEO treatment were in the range of 1.02-1.07. After the subsequent alkaline activation treatment, the surface of the 3D printed coupon included mostly plate shaped and some round particles on the surface of a nanofibrous network formed on the surface of the microporous oxide layer, as shown in FIG. 13B (10,000×). In example E29, The PEO and NaOH solution treated 3D printed devices revealed a Ca/P ratio between 1.53-1.64, as shown in Table 6.

Comparing PEO and subsequent alkaline treatments of bead sintered and 3D printed devices, the bioactive surface comprising a composite nanofibrous network of sodium and/or calcium titanate with embedded hydroxyapatite particles (having a mixed plate or round shape), or a hydroxyapatite film, in a longer hour NaOH treatment, was formed on the surface of the treated ABS CpTi; whereas a composite microstructure comprising a nanofibrous network of sodium and/or calcium titanate with an overlay of hydroxyapatite particles (with mostly plate-like shape) was formed on the 3D printed devices without forming a hydroxyapatite film. In the dense Ti alloy, the sintered bead CpTi, and the 3D printed implants of Ti alloy, the hydroxyapatite was formed, and the Ca/P ratio matched that of hydroxyapatite in human bone. Even though similar Ca/P ratios were obtained for the oxide layer formed on the ABS CpTi and 3D printed devices, the hydroxyapatite particle size, shape, and distribution over the surface of the microporous oxide layer are significantly different for the two kinds of devices after alkaline treatment. The difference can be due to the inherently different material properties of the medical devices made of CpTi metal and Ti-6A1-4V alloy, regardless of the method of manufacturing the porous CpTi coating by sintering or the porous Ti alloy coated by selective laser melting or electron beam melting.

TABLE 6

Experiments for the acid activation, PEO and alkaline treatment steps and results.

| No. | Surface activation treatment 6M HNO₃, 0.75M HF, 40° C., 20 minutes | PEO treatment f 650 Hz, Duty 20%, time 10 minutes Mean voltage, $V_m$, (volts) | NaOH treatment 0.5M, 60° C., 12 h | Elemental composition | | | |
|-----|------------|-------------|------------|------|------|------|------|
| | | | | Ca at. % | P at. % | Na at. % | Ca/P |
| E28 | Treated | Treated at 260 V | Not treated | 5.9 | 5.7 | 0.4 | 1.02-1.07 |
| E29 | Treated | Treated at 260 V | treated | 5.8 | 3.6 | 2.9 | 1.53-1.64 |

M = molarity; $V_m$ = mean voltage; f = pulse frequency; Duty = duty cycle.

The Ca/P ratios obtained after the acid activation, PEO, and alkaline activation steps for the 3D printed Ti-6Al-4V alloy coupons manufactured by the electron beam melting method, shown in Table 6, are consistent with the Ca/P ratios obtained for the 3D printed Ti-6Al-4V alloy coupons made by the selective laser melting method summarized in Table 5, indicating the same treatment steps can be used for both types of 3D printed implantable devices.

Example 4.1. ABS CpTi coupons were subjected to povidone iodine treatments after acid activation and PEO treatment steps to determine whether the surface of the coupons can be modified with antibacterial properties. The treatment step 140 is designed to impregnate povidone iodine on and into the surface of the porous coated device. The conditions and results of several experiments are shown in Table 7 below, with reference to the figures.

TABLE 7

Experiments for potential use in the treatment step 140.

Figure 14:
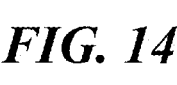
FIG. 14 is an SEM image of the surface of a porous coated medical device after an iodine treatment in Example 4, in accordance with embodiments described herein.
Figure 14:
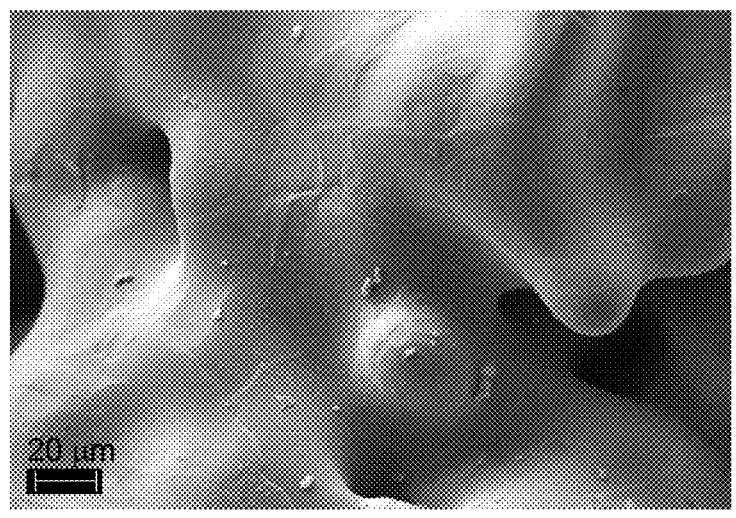
Figure 15A:
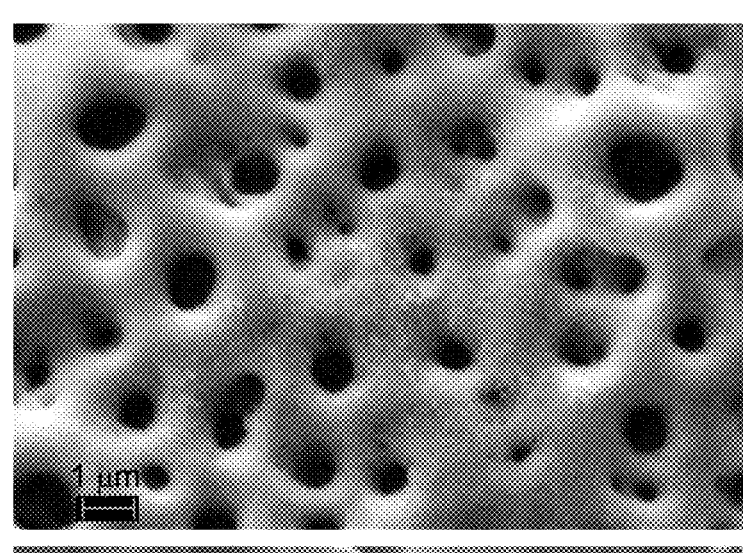
FIG. 15A, FIG. 15B, and FIG. 15C are SEM images of the surface of a porous coated medical device after PEO treatment and a subsequent iodine treatment in Example 4.1, in accordance with embodiments described herein.

| No. | Conditions | Results |
|-----|-----------|---------|
| CE9 | ABS coupon was soaked in a 10 w/v % povidone-iodine solution for 6 hours at room temperature, followed by rinsing with DI water. | Iodine deposits were not observed. |
| CE10 | ABS coupon was added to a 0.04 w/v % iodine solution prepared in deionized water and added to an electrodeposition chamber and the treatment was performed at 150 V for 15 minutes, followed by rinsing with DI water. | Iodine deposits are shown on the surface. FIG. 14 (510X) |
| E30 | After a PEO treatment, an ABS coupon was added to a 0.04 w/v % iodine solution prepared in deionized water and added to an electrodeposition chamber and | Iodine deposits are shown on the surface and in some pores. FIG. 15A (8000X) |

TABLE 7-continued

Experiments for potential use in the treatment step 140.

Figure 15B:
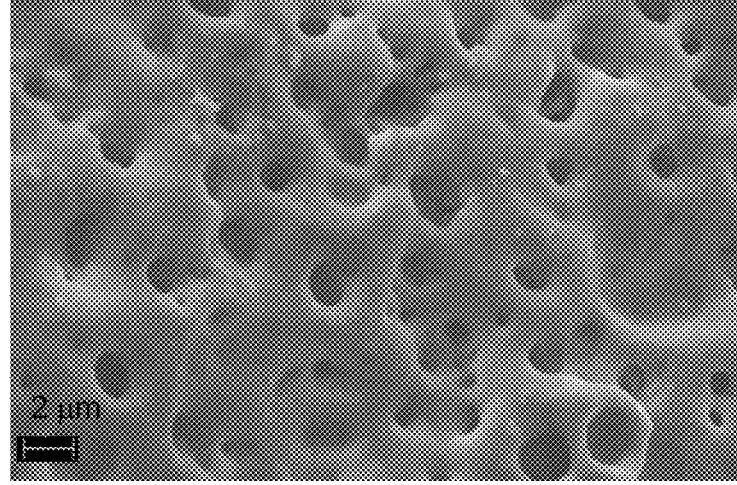
Figure 15C:
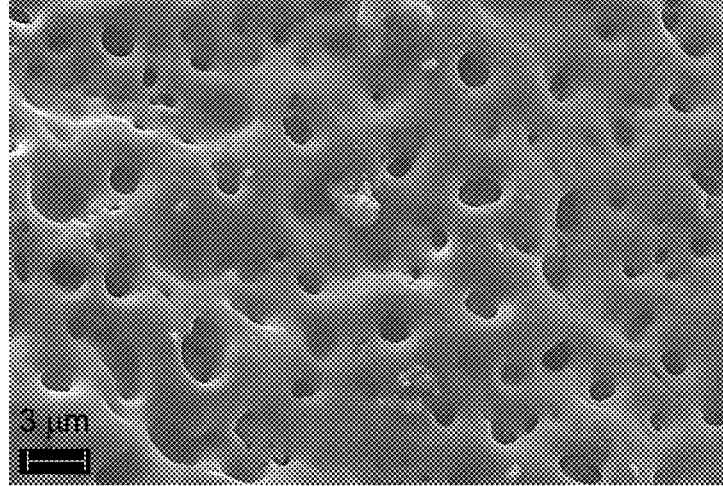

| No. | Conditions | Results |
|---|---|---|
| | the treatment was performed at 150 V for 15 minutes, followed by rinsing with DI water. | |
| E31 | After a PEO treatment, an ABS coupon was added to a 10 w/v % povidone-iodine solution for 6 hours at 40° C., followed by rinsing with DI water. | Iodine deposits are shown on the surface and in some pores. FIG. 15B (3730X), FIG. 15C (3000X) |

Entry No. CE9 in Table 7 shows that soaking an ABS coupon with a CpTi porous coated coupon in a 10 w/v % povidone-iodine solution, without any other surface treatments, does not result in the immobilization or impregnation of PI deposits on the surface of the coating. SEM images confirmed a lack of iodine on the surface.

The SEM image in FIG. 14 (510x) shows the surfaces of a porous coated ABS CpTi coupon for example CE10 in Table 7 after the povidone iodine treatment. The SEM images show agglomerates of the povidone iodine can be deposited throughout the surface of the ABS coupon using electrodeposition method. In CE10, a solution of iodine was added to the deposition chamber and, after washing, it was observed that clumps of iodine were incorporated into the porous coated ABS CpTi coupon. The ABS coupons treated in CE10 were not subjected to any pre-treatment steps (e.g., activating step 115, or PEO treatment step 125). In CE10, the deposited povidone iodine on the surface of the ABS coupons was non-uniform.

The example E30 included the treatment of a porous coated ABS CpTi coupon with a PEO treatment according to step 125 followed by an povidone iodine treatment according to step 140. In E30, the povidone iodine was deposited via electrodeposition after the PEO treatment. FIG. 15A (8000x) is an SEM image showing a uniform deposition of iodine on the oxidized porous coated substrate.

The example E31 included the treatment of a porous coated ABS CpTi coupon with a PEO treatment according to step 125 followed by an iodine treatment according to step 140. In E31, the treated porous coated coupon was submerged in a 10 w/v % povidone-iodine bath at 40° C. after the PEO treatment. FIG. 15B (3730x) and FIG. 15C (3000x) are SEM images of widespread iodine deposited on the surface of the oxidized porous coating.

The data obtained from the series of experiments in Table 7 shows that a porous coated ABS CpTi coupon can receive povidone iodine deposits under certain conditions. And unexpectedly, the iodine can be uniformly deposited on a PEO-treated porous coated coupon having bioactive phases by submerging the coupon in an iodine bath at mild temperatures (e.g., temperatures as low as 25-60° C.) without requiring any specialized equipment. Without being bound to a particular scientific theory, it is believed that abundant Ti—OH groups are present on the oxide layer that can facilitate the immobilization of $I^{3-}$ in povidone iodine on the oxide surface more uniformly. Increasing basicity (i.e., Ti—OH groups) of metal oxides by the NaOH treatment of the PEO treated oxide layer generally can enhance the strength of interaction with iodine. The iodine treated composite bioactive surface of the nanofibrous network and hydroxyapatite also shows iodine adsorption at temperatures ranging from room temperature to 60° C. By applying soaking method, the povidone iodine can be immobilized in the interior of the complex porous orthopedic medical devices, which can ensure protection against infection over a long period of time after surgery.

Example 4.2. ABS CpTi coupons that were subjected to iodine treatments after acid activation, PEO treatment, and alkaline treatment steps were next examined to determine whether the surface of the coupons would be cytotoxic to patients during use. Examples E32-E34 were subjected to an acid activation, a PEO treatment according to step 125, followed by an alkaline treatment with 0.5M NaOH solution at 60° C. for 12 hours, followed by the iodine treatment according to step 140. In examples E32-E34, the coupon was submerged in a povidone-iodine bath at 40° C. for 24 hours, but the concentration of the povidone-iodine was varied. In E32, the coupon was submerged in 0.5 w/v % povidone-iodine. In E33, the coupon was submerged in 1 w/v % povidone-iodine. In E34, the coupon was submerged in 3.5 w/v % povidone-iodine. In each of E32-E34, the iodine treated coupon was washed inside an orbital shaker at 40° C. for 3 minutes and then dried inside oven at 65° C. for 2 hours. Next, the iodine treated coupons in E32-E34, and the PEO and alkaline solution treated coupon used as a control, were submerged in a complete cell culture media (alpha-MEM, 10% FBS containing 4 mM glutamine, 1% antibiotic) for 24 hours inside an incubator maintained at 37° C. with a 5% $CO_2$ atmosphere. The hMSCs and L929 fibroblasts were used for evaluating the cytotoxicity by an extraction method in which extracts of media obtained by soaking the iodine treated coupons were poured onto cells seeded onto 12 well plates and incubated for 24 hours, and the remaining protocol was followed as per ISO 10993-5 (2009) protocol. The results demonstrated minimal cytotoxicity of both cell lines in presence of extracts of iodine-soaked coupons. Almost no cytotoxicity was found for the control sample, i.e., a PEO and NaOH treated coupon without iodine treatment. The combination of acid activation step 115, PEO step 125, alkaline step 135 and antibacterial step 140 are applied to obtain a titanium based medical device with bioactive and antibacterial surface for enhancing bone regeneration and preventing infections.

One or more of the surface treatments described herein can be used to modify various three-dimensional porous coated or porous devices comprised of titanium metal or titanium alloy to provide improved bioactivity and antibacterial activity. For example, in some embodiments, the device may be an acetabular cup of an artificial hip joint, wherein the porous structure on the acetabular cup comprises titanium powder particles, titanium metal or titanium alloy beads or wires. In some embodiments, a device prepared according to the methods described herein may be used for various surgical procedures, including total shoulder arthroplasty (glenoid base plate, humeral head/stem), reverse total shoulder arthroplasty, elbow arthroplasty, radial head arthroplasty, proximal femur replacement, total hip arthroplasty, total knee arthroplasty, unicompartmental knee arthroplasty, proximal tibial arthroplasty, total ankle arthro-plasty, etc. In some embodiments, the porous structure of the coating can have various shapes and can be formed by various methods, including, e.g., conventional plasma spray-ing, sintering, arc vapor deposition, advanced additive manufacturing, or 3D printing.

In some embodiments, for example, the three-dimen-sional porous coated device is a knee tibia base plate of a titanium alloy having a porous coating of pure titanium metal or titanium alloy thereon. In some embodiments, porous coatings made of tantalum metal or a tantalum alloy are subjected to one or more of the surface treatments described herein and can be applied to porous or non-porous implants made of tantalum metal or alloys.

As one of skill would appreciate that the methods dis-closed herein may be carried out with or without one or more of the specific steps discussed in this disclosure. In various embodiments, one or more steps of the method 100 may be omitted. In some embodiments, the method comprises, consists of, or consists essentially of the PEO treatment step 125 and the activating step 135. In some embodiments, the method comprises, consists of, or consists essentially of the acid solution activation step 115, the PEO treatment step 125, and the basic solution activating step 135. In some embodiments, the method comprises, consists of, or consists essentially of the degreasing step 110, the activation step 115, the washing step 120, the PEO treatment step 125, and the washing step 130. In some embodiments, the method comprises, consists of, or consists essentially of the degreas-ing step 110, the activation step 115, the washing step 120, the PEO treatment step 125, the washing step 130, the iodine treatment step 140, and the washing step 145. In some embodiments, the method comprises, consists of, or consists essentially of the degreasing step 110, the activation step 115, the washing step 120, the PEO treatment step 125, and the washing step 130, the activating step 135, and the washing step 145. In some embodiments, the method com-prises, consists of, or consists essentially of the degreasing step 110, the activation step 115, the washing step 120, the PEO treatment step 125, the washing step 130, the activating step 135, the iodine treatment step 140, and the washing step 145.

The foregoing embodiments are provided to aid in the understanding of the present disclosure, the true scope of which is set forth in the appended claims. One of skill in the art would appreciate that modifications can be made in the embodiments set forth without departing from the spirit of the disclosure.

Exemplary embodiments and examples of the systems and methods are described above in detail. The systems and methods are not limited to the specific embodiments described herein, but rather, components of the systems and/or steps of the method may be utilized independently and separately from other components and/or steps described herein. For example, the system may also be used in combination with other systems and methods, and is not limited to practice with only a system as described herein. Rather, the exemplary embodiment can be implemented and utilized in connection with many other systems.

A recitation of ranges of values herein are merely intended to serve as a shorthand method of referring indi-vidually to each separate value falling within the range, unless otherwise indicated herein, and each separate value is incorporated into the specification as if it were individually recited herein. As will be understood by one skilled in the art, ranges disclosed herein encompass any and all possible subranges and combinations of subranges thereof. Any listed range can be easily recognized as sufficiently describing the same range being broken down into at least equal halves, thirds, quarters, fifths, tenths, etc. For example, a range of 2% to 3% includes 2.3% to 2.8%, 2.4% to 2.9%, etc. As a non-limiting example, each range discussed herein can be readily broken down into a lower third, middle third and upper third, etc. As will also be understood by one skilled in the art, language such as "up to," "at least," "greater than," "less than," and the like include the number recited and refer to ranges which can be subsequently broken down into subranges as discussed above. Finally, as will be understood by one skilled in the art, a range includes each endpoint and individual member. For example, a range of 4% to 10% includes the subranges 5% to 9%, 6% to 8%, etc., and each endpoint (e.g., 4%, 5%, 6%, 8%, 9%, 10%) can be recited as an individual limitation.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context.

As used herein, the use of examples, or exemplary lan-guage (e.g., "such as"), is intended to illuminate the embodi-ments and does not pose a limitation on the scope of the claims unless otherwise stated. No language in the specifi-cation should be construed as indicating any non-claimed element as essential.

As used herein, the terms "about" and "substantially" will be understood by persons of ordinary skill in the art and will vary to some extent depending upon the context in which it is used. If there are uses of the term which are not clear to persons of ordinary skill in the art, given the context in which it is used, "about" and "substantially" will mean up to plus or minus 10% of the particular term.

This written description uses examples to disclose the present embodiments, including the best mode, and to enable any person skilled in the art to practice the present embodiments, including carrying out the steps of the method. The patentable scope of the present embodiments is defined by the claims, and may include other examples that occur to those skilled in the art. Such other examples are intended to be within the scope of the claims if they have elements that do not differ from the literal language of the claims, or if they include equivalent elements with insub-stantial differences from the literal language of the claims.

I claim:

1. A method of producing a bioactive surface on a medical device configured for cementless implantation, the method comprising the following sequential steps:

providing a medical device comprising a surface and formed of commercially pure titanium metal or a titanium alloy, wherein the surface is porous or porous coated;

treating the medical device with an acidic solution con-sisting of nitric acid at a concentration in the range of 3 M to 10 M and hydrofluoric acid at a concentration in the range of 0.1 M to 1 M, at a temperature between 20° C. and 60° C., to form an activated surface on the medical device, wherein an extent of etching relative to a total surface area is 15% or less;

treating the activated surface using a plasma electrolytic oxidation process in an electrolyte solution comprising calcium and phosphate salts, at a temperature between 15° C. and 50° C., to form an oxidized surface on the medical device comprising a microporous oxide layer having bioactive elements, compounds, or phases, the microporous oxide layer at least comprising hydroxyapatite wherein an extent of uniformity of the microporous oxide layer relative to total surface area treated is at least 85%; and chemically treating the resulting oxidized surface of the medical device with an alkaline solution comprising a hydroxide at a concentration in the range of 0.01 M to 5.0 M, at a temperature between 20° C. and 90° C. to form a bioactive surface on the medical device, the bioactive surface comprising a structure selected from the group consisting of: a nanofibrous network, a composite of a nanofibrous network and nano-to-micro sized calcium phosphate particles, and a composite of the nanofibrous network, nano-to-micro sized calcium phosphate particles and a film comprising hydroxyapatite, wherein the particles or film are formed on the surface of the nanofibrous network.

2. The method of claim 1, wherein the medical device is treated with the acidic solution consisting of the nitric acid at a molar concentration in the range of 4 M to 9 M, and the hydrofluoric acid at a molar concentration in the range of 0.1 M to 1 M, wherein the extent of etching relative to total surface area is 15% or less.

3. The method of claim 1, wherein the medical device is comprised of the titanium alloy, and wherein the surface of the medical device is porous coated by sintering, plasma spraying, or 3D printing of one or more compositions comprising titanium alloy powder compositions.

4. The method of claim 3, wherein the medical device is a porous, 3D-printed medical device, further comprising, prior to treating the porous 3D-printed medical device with the acidic solution, the following sequential steps:

submerging the porous, 3D-printed medical device in a detergent solution;

subjecting the submerged medical device to ultrasonication at a temperature in the range of 40° C. to 60° C. for a duration of about 1 to 2 hours to remove impurities, and entrapped residual powders from the surface and within the submerged medical device; and further ultrasonicating the resulting medical device in deionized water to remove residual organic compounds from the surface and within the medical device.

5. The method of claim 1, wherein the medical device is obtained by 3D printing one or more titanium alloy powder compositions.

6. The method of claim 1, wherein the alkaline solution has the hydroxide in a concentration range of 0.1 M to 1.0 M.

7. The method of claim 1, wherein the hydroxide is sodium hydroxide or potassium hydroxide.

8. The method of claim 1, wherein the oxidized surface further comprises calcium and phosphorus in a calcium to phosphorus atomic percentage ratio in a range from 0.5 to 1.22.

9. The method of claim 1, wherein the bioactive surface further comprises calcium and phosphorous in a calcium to phosphorous atomic percentage ratio in a range from 1.14 to 2.21.

10. The method of claim 1, wherein the bioactive surface further comprises at least one compound or combination of compounds selected from the group consisting of: calcium titanate, sodium titanate, sodium hydrogen titanate, a titanate having a bioactive or antibacterial element, calcium phosphate, and calcium phosphate having a bioactive or antibacterial element.

11. The method of claim 1, wherein the plasma electrolytic oxidation process comprises: a mean voltage in the range of 150 V to 800 V; a pulse frequency in the range of 5 Hz to 1500 Hz and a duty cycle in the range of 3% to 30%.

12. The method of claim 11, wherein the mean voltage is in a range of 200 V to 500 V, and the pulse frequency is in a range of 400 Hz to 1000 Hz.

13. The method of claim 1, further comprising, after treating the medical device with the acidic solution, washing the activated surface in water for a duration of 5 to 60 minutes at a temperature in the range of 40° C. to 60° C., to remove any residual acidic solution and impurities from the surface and within the porous surface of the medical device.

14. The method of claim 1, further comprising, after treating the medical device using the plasma electrolytic oxidation process, washing the medical device in water for a duration of 5 to 60 minutes, to remove physically adsorbed residual salts from the oxidized surface and from within the porous surface of the medical device.

15. The method of claim 1, further comprising, after chemically treating the oxidized surface with the alkaline solution, washing the medical device to remove physically adsorbed ions from the porous, bioactive surface and from within the porous, bioactive surface of the medical device.

16. The method of claim 1, further comprising treating the medical device with an iodine-containing solution to obtain an antibacterial surface, wherein iodine is incorporated into the microporous oxide layer or bioactive surface by (i) electrodeposition, or (ii) submersion in the iodine-containing solution at a temperature between 25° C. and 60° C.

17. The method of claim 16, wherein the microporous oxide layer or bioactive surface comprises the iodine incorporated by (i) electrodeposition, or (ii) submerging the medical device in the iodine-containing solution.

18. A method of producing a bioactive surface on a medical device configured for cementless implantation, the medical device comprising a porous commercially pure titanium metal or titanium alloy coating on PEEK or PEKK polymer, the method comprising the following sequential steps:

treating the medical device with an acidic solution consisting of nitric acid at a concentration in the range of 3 M to 10 M, and hydrofluoric acid at a concentration in the range of 0.1 M to 1 M, at a temperature between 20° C. and 60° C., to form an activated surface on the medical device, wherein an extent of etching relative to a total surface area is 15% or less;

treating the activated surface using a plasma electrolytic oxidation process in an electrolyte solution comprising calcium and phosphate salts, at a temperature between 15° C. and 50° C., to form an oxidized surface on the medical device comprising a microporous oxide layer having bioactive elements, compounds, or phases, the microporous oxide layer at least comprising hydroxyapatite, and wherein an extent of uniformity of the microporous oxide layer relative to total surface area treated is at least 85%; and chemically treating the resulting oxidized surface of the medical device with an alkaline solution comprising a hydroxide at a concentration in the range of 0.01 M to 5.0 M, at a temperature between 20° C. and 90° C., to form a bioactive surface on the medical device, the bioactive surface comprising a structure selected from the group consisting of: a nanofibrous network, a composite of a nanofibrous network and calcium phosphate particles, and a composite of the nanofibrous network, calcium phosphate particles and a film comprising hydroxyapatite, wherein the particles or film are formed on the surface of the nanofibrous network;

wherein the bioactive surface further comprises calcium and phosphorus in a calcium to phosphorous atomic percentage ratio of about 1.67 and sodium in atomic percentage range of 0.5 to 10.

19. A method of producing an antibacterial and bioactive surface on a medical device configured for cementless implantation, the method comprising the following sequential steps:

providing a medical device comprising a surface and formed of commercially pure titanium metal or a titanium alloy, wherein the surface is dense;

treating the medical device with an acidic solution consisting of nitric acid at a concentration in the range of 5 M to 10 M, hydrofluoric acid at a concentration in the range of 0.1 M to 2 M, at a temperature between 40° C. and 60° C., to form an activated surface on the medical device, wherein an extent of etching relative to a total surface area is 15% or less;

washing the activated surface on the medical device in water for 5-30 minutes at a temperature in the range of 40° C. to 60° C., to remove residual acidic solution from the surface;

treating the washed activated surface using a plasma electrolytic oxidation process in an electrolyte solution comprising calcium and phosphate salts, at a temperature between 15° C. and 50° C., to form an oxidized surface on the medical device comprising a microporous oxide layer having bioactive elements, compounds, or phases, the microporous oxide layer at least comprising hydroxyapatite, and wherein an extent of uniformity of the microporous oxide layer relative to total surface area treated is at least 85%;

washing the oxidized medical device in water for 5 to 60 minutes, to remove salts from the electrolyte solution that are physically adsorbed onto the medical device; and chemically treating the resulting oxidized surface of the medical device with an alkaline solution comprising a hydroxide at a concentration in the range of 0.01 M to 5.0 M, at a temperature between 20° C. and 90° C., to form a bioactive surface on the medical device, the bioactive surface comprising a structure selected from the group consisting of: a nanofibrous network, a composite of a nanofibrous network and calcium phosphate particles, and a composite of the nanofibrous network, calcium phosphate particles and a film comprising hydroxyapatite, wherein the particles or film are formed on the surface of the nanofibrous network;

washing the resulting medical device in water to remove physically adsorbed ions from the surface of the medical device;

treating the resulting medical device with an iodine-containing solution to obtain the antibacterial and bioactive surface, wherein iodine is incorporated into the microporous oxide layer or bioactive surface by (i)

electrodeposition, or (ii) submersion in the iodine-containing solution at a temperature between 25° C. to 60° C.;

washing the resulting medical device with water to remove residual iodine from the surface of the medical device; and drying the medical device.

20. A method of producing a bioactive surface on a medical device configured for cementless implantation, the medical device comprising a surface and comprised of a sintered bead porous coating made of commercially pure titanium metal or a titanium alloy, the method comprising the following sequential steps:

treating the medical device with an acidic solution consisting of nitric acid at a concentration in the range of 3 M to 10 M, hydrofluoric acid at a concentration in the range of 0.1 M to 1 M, at a temperature between 20° C. and 60° C., to form an activated surface on the medical device, wherein an extent of etching relative to a total surface area is 15% or less;

treating the activated surface using a plasma electrolytic oxidation process in an electrolyte solution comprising calcium and phosphate salts, at a temperature between 15° C. and 50° C., to form an oxidized surface on the medical device comprising a microporous oxide layer having bioactive elements, compounds, or phases, the microporous oxide layer at least comprising hydroxyapatite, and wherein an extent of uniformity of the microporous oxide layer relative to total surface area treated is at least 85%; and chemically treating the resulting oxidized surface of the medical device with an alkaline solution comprising a hydroxide at a concentration in the range of 0.01 M to 5.0 M, at a temperature between 20° C. and 90° C., to form a bioactive surface on the medical device, the bioactive surface comprising a structure selected from the group consisting of: a nanofibrous network, a composite of a nanofibrous network and calcium phosphate particles, and a composite of the nanofibrous network, calcium phosphate particles and a film comprising hydroxyapatite, wherein the particles or film are formed on the surface of the nanofibrous network;

wherein the bioactive surface further comprises calcium and phosphorus in a calcium to phosphorous atomic percentage ratio from 1.50 to 1.74.

21. The method of claim 20, further comprising an iodine treatment step comprising incorporating povidone iodine into the microporous oxide layer or bioactive surface of the medical device by (i) electrodeposition, or (ii) submersion in a povidone iodine-containing solution at a temperature in the range of 25° to 60° C., to obtain an antibacterial surface, wherein povidone iodine is retained within the micro-porous oxide layer or bioactive surface.

* * * * *